US007241879B2

(12) United States Patent
Chien et al.

(10) Patent No.: US 7,241,879 B2

(45) Date of Patent: Jul. 10, 2007

(54) IMMUNOASSAYS FOR ANTI-HCV ANTIBODIES

(75) Inventors: David Y. Chien, Alamo, CA (US); Phillip Arcangel, Oakland, CA (US); Laura Tandeske, San Leandro, CA (US); Carlos George-Nascimento, Walnut Creek, CA (US); Doris Coit, Petaluma, CA (US); Angelica Medina-Selby, San Francisco, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 373 days.

(21) Appl. No.: 10/899,715

(22) Filed: Jul. 26, 2004

(65) Prior Publication Data

US 2004/0265801 A1 Dec. 30, 2004

Related U.S. Application Data

(60) Continuation of application No. 10/637,323, filed on Aug. 8, 2003, now Pat. No. 6,797,809, which is a division of application No. 09/881,654, filed on Jun. 14, 2001, now Pat. No. 6,632,601.

(60) Provisional application No. 60/280,867, filed on Apr. 2, 2001, provisional application No. 60/280,811, filed on Apr. 2, 2001, provisional application No. 60/212,082, filed on Jun. 15, 2000.

(51) Int. Cl.
*C07H 21/04* (2006.01)

(52) U.S. Cl. .................... 536/23.4; 435/69.7; 435/328; 530/350

(58) Field of Classification Search ................ 530/350; 435/41, 69.7, 328; 536/23.4
See application file for complete search history.

(56) References Cited

U.S. PATENT DOCUMENTS

| | | | |
|---|---|---|---|
| 5,350,671 | A | 9/1994 | Houghton et al. |
| 5,683,864 | A | 11/1997 | Houghton et al. |
| 5,712,087 | A | 1/1998 | Houghton et al. |
| 5,843,752 | A | 12/1998 | Dasmahapatra et al. |
| 5,871,904 | A | 2/1999 | Kashiwakuma et al. |
| 5,990,276 | A | 11/1999 | Zhang et al. |
| 6,171,782 | B1 | 1/2001 | Houghton et al. |
| 6,428,792 | B1 | 8/2002 | Valenzuela et al. |
| 6,514,731 | B1 | 2/2003 | Valenzuela et al. |
| 6,630,298 | B2 | 10/2003 | Chien et al. |
| 2003/0044774 | A1 | 3/2003 | Valenzuela et al. |

FOREIGN PATENT DOCUMENTS

| | | |
|---|---|---|
| EP | 318216 | 5/1989 |
| EP | 388232 | 9/1990 |
| EP | 0450931 B1 | 10/1991 |
| EP | 0472207 A2 | 2/1992 |
| EP | 0 870 830 A2 | 10/1998 |
| GB | 2 212 511 B | 7/1989 |
| GB | 2 257 784 B | 1/1993 |
| PT | 97 247 | 7/1997 |
| WO | WO 93/00365 | 1/1993 |
| WO | WO 94/01778 | 1/1994 |
| WO | WO 94 25601 | 11/1994 |
| WO | WO 97 12043 | 4/1997 |
| WO | WO 97/44469 | 11/1997 |

OTHER PUBLICATIONS

Beld et al., "Evaluation of automated RNA-extraction technology and a qualitative HCV assay for sensitivity and detection of HCV RNA in pool-screening systems," *Transfusion* 40:575-579, 2000.

Chen et al., "Human and murine antibody recognition is focused on the ATPase/helicase domain, but not the protease domain of the hepatitis C virus non-structural 3 protein," *Hepatology* 28:219-224, 1998.

Chien et al., "Diagnosis of Hepatitis C Virus (HCV) Infection Using an Immunodominant Chimeric Polyprotein to Capture Circulating Antibodies: Reevaluation of the Role of HCV in Liver Disease," *Proc. Natl. Acad. Sci. U.S.A.* 89:10011-10015 (1992).

Chien et al., "Use of Recombinant HCV Antigen in the Serodiagnosis of Hepatitis C Virus Infection: Significant Improvement in HCV Antibody Detection as Compared with the First Generation HCV C100-3 ELISA and the Synthetic Peptide EIA Tests," *Joruna1 of Gastroenterology Hepatology* 8:S33-39 (1993).

Chien et al., "Distinct subtypes of hepatitis C virus defined by antibodies directed to the putative core, NS4, and NS5 region polypeptides," *Virol. Hepatitis and Liver Disease*:320-324, 1994.

Choo et al., "Isolation of a cDNA Clone Derived from a Blood-Borne Non-A, Non-B Viral Hepatits Genome," *Science* 244:359-362 (1989).

Choo et al., "Hepatitis C Virus: The Major Causative Agent of Viral Non-A, Non-B Hepatitis," *British Medical Bulletin* 46(2):423-441 (1990).

Cruse et al., Illustrated Dictionary of Immunology, CRC Press, Boca Raton FL, 1995, p. 76.

Ebeling et al., "Recombinant Immunoblot Assay for Hepatitis C Virus Antibody as Predictor of Infectivity," *Lancet* 335:982-983 (1990).

Houghton et al., "Molecular Biology of the Hepatitis C Viruses: Implications for Diagnos, Development and Control of Viral Disease," *Hepatology* 14:381-388 (1991).

Kotwal et al., "Detection of acute hepatitis C virus infection by ELISA using a synthetic peptide comprising a structural epitope," *Proc. Natl. Acad. Sci. USA* 89:4486-4489, 1992.

(Continued)

*Primary Examiner*—Shanon Foley
*Assistant Examiner*—Emily M. Le
(74) *Attorney, Agent, or Firm*—Marcella Lillis; Roberta L. Robins; Alisa A. Harbin

(57) ABSTRACT

HCV immunoassays comprising an NS3/4a conformational epitope and a multiple epitope fusion antigen are provided, as well as immunoassay solid supports for use with the immunoassays.

19 Claims, 20 Drawing Sheets

OTHER PUBLICATIONS

Kuo et al., "An Assay for Circulating Antibodies to a Major Etiologic Virus of Human Non-A, Non-B Hepatitis," *Science* 244:362-364 (1989).

Pereboeva et al., "Hepatitis C Epitopes From Phage-Displayed cDNA Libraries and Improved Diagnosis with a Chimeric Antigen," *J. Medical Virology* 60:144-151, 2000.

van der Poel et al., "Infectivity of Blood Seropositive for Hepatitis C Virus Antibodies," *Lancet* 335:558-560 (1990).

Van der Poel et al., "Confirmation of hepatitis C virus infection by new four-antigen recombinant immunoblot assay," *Lancet* 337:317-319, 1991.

Yao et al., "Molecular views of viral polyprotein processing revealed by the crystal structure of the hepatitis C virus bifunctional protease-helicase," Structure 7(11):1353-1363, 1999.

```
                                     1                                       10
                                     M   A   P   I   T   A   Y   A   Q   Q
                                    ATG GCG CCC ATC ACG GCG TAC GCC CAG CAG

                                                     20
 T   R   G   L   L   G   C   I   I   T   S   L   T   G   R
ACA AGG GGC CTC CTA GGG TGC ATA ATC ACC AGC CTA ACT GGC CGG

                 30                                      40
 D   K   N   Q   V   E   G   E   V   Q   I   V   S   T   A
GAC AAA AAC CAA GTG GAG GGT GAG GTC CAG ATT GTG TCA ACT GCT

                                     50
 A   Q   T   F   L   A   T   C   I   N   G   V   C   W   T
GCC CAA ACC TTC CTG GCA ACG TGC ATC AAT GGG GTG TGC TGG ACT

                 60                                      70
 V   Y   H   G   A   G   T   R   T   I   A   S   P   K   G
GTC TAC CAC GGG GCC GGA ACG AGG ACC ATC GCG TCA CCC AAG GGT

                                     80
 P   V   I   Q   M   Y   T   N   V   D   Q   D   L   V   G
CCT GTC ATC CAG ATG TAT ACC AAT GTA GAC CAA GAC CTT GTG GGC

                 90                                     100
 W   P   A   P   Q   G   S   R   S   L   T   P   C   T   C
TGG CCC GCT CCG CAA GGT AGC CGA TCA TTG ACA CCC TGC ACT TGC

                                    110
 G   S   S   D   L   Y   L   V   T   R   H   A   D   V   I
GGC TCC TCG GAC CTT TAC CTG GTC ACG AGG CAC GCC GAT GTC ATT

                120                                     130
 P   V   R   R   R   G   D   S   R   G   S   L   L   S   P
CCC GTG CGC CGG CGG GGT GAT AGC AGG GGC AGC CTG CTG TCG CCC

                                    140
 R   P   I   S   Y   L   K   G   S   S   G   G   P   L   L
CGG CCC ATT TCC TAC TTG AAA GGC TCC TCG GGG GGT CCG CTG TTG

                150                                     160
 C   P   A   G   H   A   V   G   I   F   R   A   A   V   C
TGC CCC GCG GGG CAC GCC GTG GGC ATA TTT AGG GCC GCG GTG TGC

                                    170
 T   R   G   V   A   K   A   V   D   F   I   P   V   E   N
ACC CGT GGA GTG GCT AAG GCG GTG GAC TTT ATC CCT GTG GAG AAC

                180                                     190
 L   E   T   T   M   R   S   P   V   F   T   D   N   S   S
CTA GAG ACA ACC ATG AGG TCC CCG GTG TTC ACG GAT AAC TCC TCT
```

*FIG. 3A*

```
                                        200
 P   P   V   V   P   Q   S   F   Q   V   A   H   L   H   A
CCA CCA GTA GTG CCC CAG AGC TTC CAG GTG GCT CAC CTC CAT GCT

                210                                     220
 P   T   G   S   G   K   S   T   K   V   P   A   A   Y   A
CCC ACA GGC AGC GGC AAA AGC ACC AAG GTC CCG GCT GCA TAT GCA

                                        230
 A   Q   G   Y   K   V   L   V   L   N   P   S   V   A   A
GCT CAG GGC TAT AAG GTG CTA GTA CTC AAC CCC TCT GTT GCT GCA

                240                                     250
 T   L   G   F   G   A   Y   M   S   K   A   H   G   I   D
ACA CTG GGC TTT GGT GCT TAC ATG TCC AAG GCT CAT GGG ATC GAT

                                        260
 P   N   I   R   T   G   V   R   T   I   T   T   G   S   P
CCT AAC ATC AGG ACC GGG GTG AGA ACA ATT ACC ACT GGC AGC CCC

                270                                     280
 I   T   Y   S   T   Y   G   K   F   L   A   D   G   G   C
ATC ACG TAC TCC ACC TAC GGC AAG TTC CTT GCC GAC GGC GGG TGC

                                        290
 S   G   G   A   Y   D   I   I   I   C   D   E   C   H   S
TCG GGG GGC GCT TAT GAC ATA ATA ATT TGT GAC GAG TGC CAC TCC

                300                                     310
 T   D   A   T   S   I   L   G   I   G   T   V   L   D   Q
ACG GAT GCC ACA TCC ATC TTG GGC ATT GGC ACT GTC CTT GAC CAA

                                        320
 A   E   T   A   G   A   R   L   V   V   L   A   T   A   T
GCA GAG ACT GCG GGG GCG AGA CTG GTT GTG CTC GCC ACC GCC ACC

                330                                     340
 P   P   G   S   V   T   V   P   H   P   N   I   E   E   V
CCT CCG GGC TCC GTC ACT GTG CCC CAT CCC AAC ATC GAG GAG GTT

                                        350
 A   L   S   T   T   G   E   I   P   F   Y   G   K   A   I
GCT CTG TCC ACC ACC GGA GAG ATC CCT TTT TAC GGC AAG GCT ATC

                360                                     370
 P   L   E   V   I   K   G   G   R   H   L   I   F   C   H
CCC CTC GAA GTA ATC AAG GGG GGG AGA CAT CTC ATC TTC TGT CAT

                                        380
 S   K   K   K   C   D   E   L   A   A   K   L   V   A   L
TCA AAG AAG AAG TGC GAC GAA CTC GCC GCA AAG CTG GTC GCA TTG
```

*FIG. 3B*

```
                390                                         400
 G   I   N   A   V   A   Y   Y   R   G   L   D   V   S   V
GGC ATC AAT GCC GTG GCC TAC TAC CGC GGT CTT GAC GTG TCC GTC

                                    410
 I   P   P   I   G   D   V   V   V   V   A   T   D   A   L
ATC CCG CCC ATC GGC GAT GTT GTC GTC GTG GCA ACC GAT GCC CTC

                420                                         430
 M   T   G   Y   T   G   D   F   D   S   V   I   D   C   N
ATG ACC GGC TAT ACC GGC GAC TTC GAC TCG GTG ATA GAC TGC AAT

                                    440
 T   C   V   T   Q   T   V   D   F   S   L   D   P   T   F
ACG TGT GTC ACC CAG ACA GTC GAT TTC AGC CTT GAC CCT ACC TTC

                450                                         460
 T   I   E   T   I   T   L   P   Q   D   A   V   S   R   T
ACC ATT GAG ACA ATC ACG CTC CCC CAA GAT GCT GTC TCC CGC ACT

                                    470
 Q   R   R   G   R   T   G   R   G   K   P   G   I   Y   R
CAA CGT CGG GGC AGG ACT GGC AGG GGG AAG CCA GGC ATC TAC AGA

                480                                         490
 F   V   A   P   G   E   R   P   S   G   M   F   D   S   S
TTT GTG GCA CCG GGG GAG CGC CCC TCC GGC ATG TTC GAC TCG TCC

                                    500
 V   L   C   E   C   Y   D   A   G   C   A   W   Y   E   L
GTC CTC TGT GAG TGC TAT GAC GCA GGC TGT GCT TGG TAT GAG CTC

                510                                         520
 T   P   A   E   T   T   V   R   L   R   A   Y   M   N   T
ACG CCC GCC GAG ACT ACA GTT AGG CTA CGA GCG TAC ATG AAC ACC

                                    530
 P   G   L   P   V   C   Q   D   H   L   E   F   W   E   G
CCG GGG CTT CCC GTG TGC CAG GAC CAT CTT GAA TTT TGG GAG GGC

                540                                         550
 V   F   T   G   L   T   H   I   D   A   H   F   L   S   Q
GTC TTT ACA GGC CTC ACT CAT ATA GAT GCC CAC TTT CTA TCC CAG

                                    560
 T   K   Q   S   G   E   N   L   P   Y   L   V   A   Y   Q
ACA AAG CAG AGT GGG GAG AAC CTT CCT TAC CTG GTA GCG TAC CAA

                570                                         580
 A   T   V   C   A   R   A   Q   A   P   P   P   S   W   D
GCC ACC GTG TGC GCT AGG GCT CAA GCC CCT CCC CCA TCG TGG GAC
```

*FIG. 3C*

```
                                            590
 Q   M   W   K   C   L   I   R   L   K   P   T   L   H   G
CAG ATG TGG AAG TGT TTG ATT CGC CTC AAG CCC ACC CTC CAT GGG

                    600                                 610
 P   T   P   L   L   Y   R   L   G   A   V   Q   N   E   I
CCA ACA CCC CTG CTA TAC AGA CTG GGC GCT GTT CAG AAT GAA ATC

                                            620
 T   L   T   H   P   V   T   K   Y   I   M   T   C   M   S
ACC CTG ACG CAC CCA GTC ACC AAA TAC ATC ATG ACA TGC ATG TCG

                    630                                 640
 A   D   L   E   V   V   T   S   T   W   V   L   V   G   G
GCC GAC CTG GAG GTC GTC ACG AGC ACC TGG GTG CTC GTT GGC GGC

                                            650
 V   L   A   A   L   A   A   Y   C   L   S   T   G   C   V
GTC CTG GCT GCT TTG GCC GCG TAT TGC CTG TCA ACA GGC TGC GTG

                    660                                 670
 V   I   V   G   R   V   V   L   S   G   K   P   A   I   I
GTC ATA GTG GGC AGG GTC GTC TTG TCC GGG AAG CCG GCA ATC ATA

                                            680
 P   D   R   E   V   L   Y   R   E   F   D   E   M   E   E
CCT GAC AGG GAA GTC CTC TAC CGA GAG TTC GAT GAG ATG GAA GAG

686
 C
TGC
```

*FIG. 3D*

```
 1                                         10
 M   A   T   K   A   V   C   V   L   K   G   D   G   P   V
ATG GCT ACA AAG GCT GTT TGT GTT TTG AAG GGT GAC GGC CCA GTT

                 20                                      30
 Q   G   I   I   N   F   E   Q   K   E   S   N   G   P   V
CAA GGT ATT ATT AAC TTC GAG CAG AAG GAA AGT AAT GGA CCA GTG

                                         40
 K   V   W   G   S   I   K   G   L   T   E   G   L   H   G
AAG GTG TGG GGA AGC ATT AAA GGA CTG ACT GAA GGC CTG CAT GGA

                 50                                      60
 F   H   V   H   E   F   G   D   N   T   A   G   C   T   S
TTC CAT GTT CAT GAG TTT GGA GAT AAT ACA GCA GGC TGT ACC AGT

                                         70
 A   G   P   H   F   N   P   L   S   R   K   H   G   G   P
GCA GGT CCT CAC TTT AAT CCT CTA TCC AGA AAA CAC GGT GGG CCA

                 80                                      90
 K   D   E   E   R   H   V   G   D   L   G   N   V   T   A
AAG GAT GAA GAG AGG CAT GTT GGA GAC TTG GGC AAT GTG ACT GCT

                                        100
 D   K   D   G   V   A   D   V   S   I   E   D   S   V   I
GAC AAA GAT GGT GTG GCC GAT GTG TCT ATT GAA GAT TCT GTG ATC

                110                                     120
 S   L   S   G   D   H   C   I   I   G   R   T   L   V   V
TCA CTC TCA GGA GAC CAT TGC ATC ATT GGC CGC ACA CTG GTG GTC

                                        130
 H   E   K   A   D   D   L   G   K   G   G   N   E   E   S
CAT GAA AAA GCA GAT GAC TTG GGC AAA GGT GGA AAT GAA GAA AGT

                140                                     150
 T   K   T   G   N   A   G   S   R   L   A   C   G   V   I
ACA AAG ACA GGA AAC GCT GGA AGT CGT TTG GCT TGT GGT GTA ATT

                                        160
 G   I   A   Q   N   L   N   S   G   C   N   C   S   I   Y
GGG ATC GCC CAG AAT TTG AAT TCT GGT TGC AAT TGC TCT ATC TAT

                170                                     180
 P   G   H   I   T   G   H   R   M   A   W   K   L   G   S
CCC GGC CAT ATA ACG GGT CAC CGC ATG GCA TGG AAG CTT GGT TCC

                                        190
 A   A   R   T   T   S   G   F   V   S   L   F   A   P   G
GCC GCC AGA ACT ACC TCG GGC TTT GTC TCC TTG TTC GCC CCA GGT
```

*FIG. 5A*

```
                200                                             210
A   K   Q   N   E   T   H   V   T   G   G   A   A   A   R
GCC AAA CAA AAC GAA ACT CAC GTC ACG GGA GGC GCA GCC GCC CGA

                                    220
T   T   S   G   L   T   S   L   F   S   P   G   A   S   Q
ACT ACG TCT GGG TTG ACC TCT TTG TTC TCC CCA GGT GCC AGC CAA

                230                                             240
N   I   Q   L   I   V   D   F   I   P   V   E   N   L   E
AAC ATT CAA TTG ATT GTC GAC TTT ATC CCT GTG GAG AAC CTA GAG

                                    250
T   T   M   R   S   P   V   F   T   D   N   S   S   P   P
ACA ACC ATG CGA TCT CCG GTG TTC ACG GAT AAC TCC TCT CCA CCA

                260                                             270
V   V   P   Q   S   F   Q   V   A   H   L   H   A   P   T
GTA GTG CCC CAG AGC TTC CAG GTG GCT CAC CTC CAT GCT CCC ACA

                                    280
G   S   G   K   S   T   K   V   P   A   A   Y   A   A   Q
GGC AGC GGC AAA AGC ACC AAG GTC CCG GCT GCA TAT GCA GCT CAG

                290                                             300
G   Y   K   V   L   V   L   N   P   S   V   A   A   T   L
GGC TAT AAG GTG CTA GTA CTC AAC CCC TCT GTT GCT GCA ACA CTG

                                    310
G   F   G   A   Y   M   S   K   A   H   G   I   D   P   N
GGC TTT GGT GCT TAC ATG TCC AAG GCT CAT GGG ATC GAT CCT AAC

                320                                             330
I   R   T   G   V   R   T   I   T   T   G   S   P   I   T
ATC AGG ACC GGG GTG AGA ACA ATT ACC ACT GGC AGC CCC ATC ACG

                                    340
Y   S   T   Y   G   K   F   L   A   D   G   G   C   S   G
TAC TCC ACC TAC GGC AAG TTC CTT GCC GAC GGC GGG TGC TCG GGG

                350                                             360
G   A   Y   D   I   I   I   C   D   E   C   H   S   T   D
GGC GCT TAT GAC ATA ATA ATT TGT GAC GAG TGC CAC TCC ACG GAT

                                    370
A   T   S   I   L   G   I   G   T   V   L   D   Q   A   E
GCC ACA TCC ATC TTG GGC ATT GGC ACT GTC CTT GAC CAA GCA GAG

                380                                             390
T   A   G   A   R   L   V   V   L   A   T   A   T   P   P
ACT GCG GGG GCG AGA CTG GTT GTG CTC GCC ACC GCC ACC CCT CCG

                                    400
G   S   V   T   V   P   H   P   N   I   E   E   V   A   L
GGC TCC GTC ACT GTG CCC CAT CCC AAC ATC GAG GAG GTT GCT CTG

                410                                             420
```

*FIG. 5B*

```
S   T   T   G   E   I   P   F   Y   G   K   A   I   P   L
TCC ACC ACC GGA GAG ATC CCT TTT TAC GGC AAG GCT ATC CCC CTC

                                    430
E   V   I   K   G   G   R   H   L   I   F   C   H   S   K
GAA GTA ATC AAG GGG GGG AGA CAT CTC ATC TTC TGT CAT TCA AAG

                440                                     450
K   K   C   D   E   L   A   A   K   L   V   A   L   G   I
AAG AAG TGC GAC GAA CTC GCC GCA AAG CTG GTC GCA TTG GGC ATC

                                    460
N   A   V   A   Y   Y   R   G   L   D   V   S   V   I   P
AAT GCC GTG GCC TAC TAC CGC GGT CTT GAC GTG TCC GTC ATC CCG

                470                                     480
T   S   G   D   V   V   V   V   A   T   D   A   L   M   T
ACC AGC GGC GAT GTT GTC GTC GTG GCA ACC GAT GCC CTC ATG ACC

                                    490
G   Y   T   G   D   F   D   S   V   I   D   C   N   T   C
GGC TAT ACC GGC GAC TTC GAC TCG GTG ATA GAC TGC AAT ACG TGT

                500                                     510
V   T   Q   T   V   D   F   S   L   D   P   T   F   T   I
GTC ACC CAG ACA GTC GAT TTC AGC CTT GAC CCT ACC TTC ACC ATT

                                    520
E   T   I   T   L   P   Q   D   A   V   S   R   T   Q   R
GAG ACA ATC ACG CTC CCC CAA GAT GCT GTC TCC CGC ACT CAA CGT

                530                                     540
R   G   R   T   G   R   G   K   P   G   I   Y   R   F   V
CGG GGC AGG ACT GGC AGG GGG AAG CCA GGC ATC TAC AGA TTT GTG

                                    550
A   P   G   E   R   P   S   G   M   F   D   S   S   V   L
GCA CCG GGG GAG CGC CCC TCC GGC ATG TTC GAC TCG TCC GTC CTC

                560                                     570
C   E   C   Y   D   A   G   C   A   W   Y   E   L   T   P
TGT GAG TGC TAT GAC GCA GGC TGT GCT TGG TAT GAG CTC ACG CCC

                                    580
A   E   T   T   V   R   L   R   A   Y   M   N   T   P   G
GCC GAG ACT ACA GTT AGG CTA CGA GCG TAC ATG AAC ACC CCG GGG

                590                                     600
L   P   V   C   Q   D   H   L   E   F   W   E   G   V   F
CTT CCC GTG TGC CAG GAC CAT CTT GAA TTT TGG GAG GGC GTC TTT

                                    610
T   G   L   T   H   I   D   A   H   F   L   S   Q   T   K
ACA GGC CTC ACT CAT ATA GAT GCC CAC TTT CTA TCC CAG ACA AAG

                620                                     630
Q   S   G   E   N   L   P   Y   L   V   A   Y   Q   A   T
```

FIG. 5C

```
CAG AGT GGG GAG AAC CTT CCT TAC CTG GTA GCG TAC CAA GCC ACC

                                  640
 V   C   A   R   A   Q   A   P   P   P   S   W   D   Q   M
GTG TGC GCT AGG GCT CAA GCC CCT CCC CCA TCG TGG GAC CAG ATG

                650                                     660
 W   K   C   L   I   R   L   K   P   T   L   H   G   P   T
TGG AAG TGT TTG ATT CGC CTC AAG CCC ACC CTC CAT GGG CCA ACA

                                  670
 P   L   L   Y   R   L   G   A   V   Q   N   E   I   T   L
CCC CTG CTA TAC AGA CTG GGC GCT GTT CAG AAT GAA ATC ACC CTG

                680                                     690
 T   H   P   V   T   K   Y   I   M   T   C   M   S   A   D
ACG CAC CCA GTC ACC AAA TAC ATC ATG ACA TGC ATG TCG GCC GAC

                                  700
 L   E   V   V   T   S   A   C   S   G   K   P   A   I   I
CTG GAG GTC GTC ACG AGC GCA TGC TCC GGG AAG CCG GCA ATC ATA

                710                                     720
 P   D   R   E   V   L   Y   R   E   F   D   E   M   E   E
CCT GAC AGG GAA GTC CTC TAC CGA GAG TTC GAT GAG ATG GAA GAG

                                  730
 C   S   Q   H   L   P   Y   I   E   Q   G   M   M   L   A
TGC TCT CAG CAC TTA CCG TAC ATC GAG CAA GGG ATG ATG CTC GCC

                740                                     750
 E   Q   F   K   Q   K   A   L   G   L   S   R   G   G   K
GAG CAG TTC AAG CAG AAG GCC CTC GGC CTC TCG CGA GGG GGC AAG

                                  760
 P   A   I   V   P   D   K   E   V   L   Y   Q   Q   Y   D
CCG GCA ATC GTT CCA GAC AAA GAG GTG TTG TAT CAA CAA TAC GAT

                770                                     780
 E   M   E   E   C   S   Q   A   A   P   Y   I   E   Q   A
GAG ATG GAA GAG TGC TCA CAA GCT GCC CCA TAT ATC GAA CAA GCT

                                  790
 Q   V   I   A   H   Q   F   K   E   K   V   L   G   L   I
CAG GTA ATA GCT CAC CAG TTC AAG GAA AAA GTC CTT GGA TTG ATC

                800                                     810
 D   N   D   Q   V   V   V   T   P   D   K   E   I   L   Y
GAT AAT GAT CAA GTG GTT GTG ACT CCT GAC AAA GAA ATC TTA TAT

                                  820
 E   A   F   D   E   M   E   E   C   A   S   K   A   A   L
GAG GCC TTT GAT GAG ATG GAA GAA TGC GCC TCC AAA GCC GCC CTC

                830                                     840
 I   E   E   G   Q   R   M   A   E   M   L   K   S   K   I
ATT GAG GAA GGG CAG CGG ATG GCG GAG ATG CTC AAG TCT AAG ATA
```

*FIG. 5D*

```
                                        850
Q   G   L   L   G   I   L   R   R   H   V   G   P   G   E
CAA GGC CTC CTC GGG ATA CTG CGC CGG CAC GTT GGT CCT GGC GAG

                860                                     870
G   A   V   Q   W   M   N   R   L   I   A   F   A   S   R
GGG GCA GTG CAG TGG ATG AAC CGG CTG ATA GCC TTC GCC TCC AGA

                                        880
G   N   H   V   S   P   T   H   Y   V   P   S   R   S   R
GGG AAC CAT GTT TCC CCC ACG CAC TAC GTT CCG TCT AGA TCC CGG

                890                                     900
R   F   A   Q   A   L   P   V   W   A   R   P   D   Y   N
AGA TTC GCC CAG GCC CTG CCC GTT TGG GCG CGG CCG GAC TAT AAC

                                        910
P   P   L   V   E   T   W   K   K   P   D   Y   E   P   P
CCC CCG CTA GTG GAG ACG TGG AAA AAG CCC GAC TAC GAA CCA CCT

                920                                     930
V   V   H   G   R   S   S   R   R   F   A   Q   A   L   P
GTG GTC CAC GGC AGA TCT TCT CGG AGA TTC GCC CAG GCC CTG CCC

                                        940
V   W   A   R   P   D   Y   N   P   P   L   V   E   T   W
GTT TGG GCG CGG CCG GAC TAT AAC CCC CCG CTA GTG GAG ACG TGG

                950                                     960
K   K   P   D   Y   E   P   P   V   V   H   G   R   K   T
AAA AAG CCC GAC TAC GAA CCA CCT GTG GTC CAT GGC AGA AAG ACC

                                        970
K   R   N   T   N   R   R   P   Q   D   V   K   F   P   G
AAA CGT AAC ACC AAC CGG CGG CCG CAG GAC GTC AAG TTC CCG GGT

                980                                     990
G   G   Q   I   V   G   R   R   G   P   P   I   P   K   A
GGC GGT CAG ATC GTT GGT CGC AGG GGC CCT CCT ATC CCC AAG GCT

                                        1000
R   R   P   E   G   R   T   W   A   Q   P   G   Y   P   W
CGT CGG CCC GAG GGC AGG ACC TGG GCT CAG CCC GGT TAC CCT TGG

                1010                                    1020
P   L   Y   G   N   K   D   R   R   S   T   G   K   S   W
CCC CTC TAT GGC AAT AAG GAC AGA CGG TCT ACA GGT AAG TCC TGG

                                        1030
G   K   P   G   Y   P   W   P   R   K   T   K   R   N   T
GGT AAG CCA GGG TAC CCT TGG CCA AGA AAG ACC AAA CGT AAC ACC

                1040                                    1050
N   R   R   P   Q   D   V   K   F   P   G   G   G   Q   I
AAC CGA CGG CCG CAG GAC GTC AAG TTC CCG GGT GGC GGT CAG ATC
```

*FIG. 5E*

```
                                             1060
 V   G   R   R   G   P   P   I   P   K   A   R   R   P   E
GTT GGT CGC AGG GGC CCT CCT ATC CCC AAG GCT CGT CGG CCC GAG

                    1070                                      1080
 G   R   T   W   A   Q   P   G   Y   P   W   P   L   Y   G
GGC AGG ACC TGG GCT CAG CCC GGT TAC CCT TGG CCC CTC TAT GGC

                                             1090
 N   K   D   R   R   S   T   G   K   S   W   G   K   P   G
AAT AAG GAC AGA CGG TCT ACC GGT AAG TCC TGG GGT AAG CCA GGG

                1099
 Y   P   W   P
TAT CCT TGG CCC
```

FIG. 5F

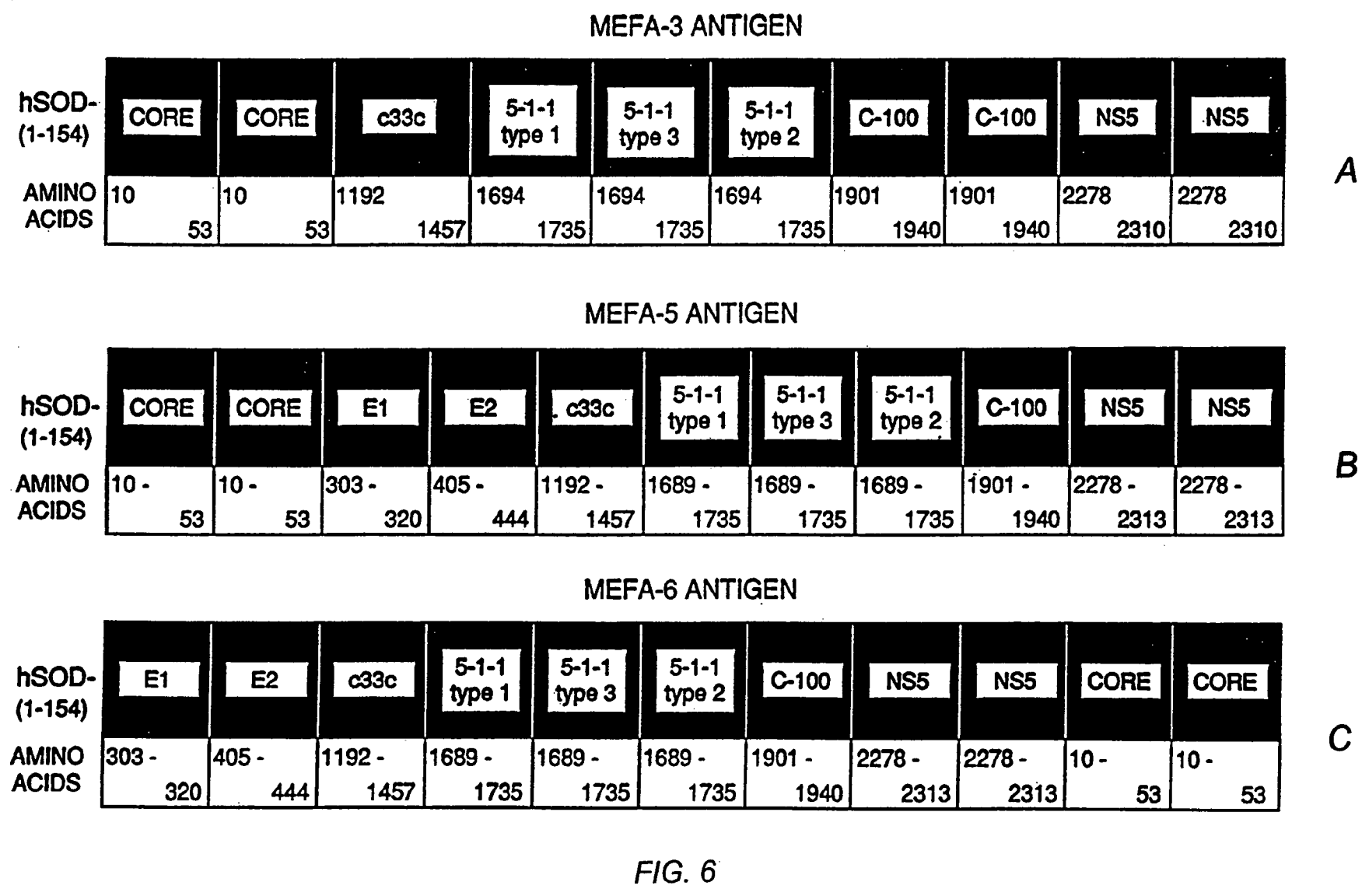

MEFA-3 ANTIGEN

A

| hSOD-(1-154) | CORE | CORE | c33c | 5-1-1 type 1 | 5-1-1 type 3 | 5-1-1 type 2 | C-100 | C-100 | NS5 | NS5 |
|---|---|---|---|---|---|---|---|---|---|---|
| AMINO ACIDS | 10 53 | 10 53 | 1192 1457 | 1694 1735 | 1694 1735 | 1694 1735 | 1901 1940 | 1901 1940 | 2278 2310 | 2278 2310 |

MEFA-5 ANTIGEN

B

| hSOD-(1-154) | CORE | CORE | E1 | E2 | c33c | 5-1-1 type 1 | 5-1-1 type 3 | 5-1-1 type 2 | C-100 | NS5 | NS5 |
|---|---|---|---|---|---|---|---|---|---|---|---|
| AMINO ACIDS | 10 - 53 | 10 - 53 | 303 - 320 | 405 - 444 | 1192 - 1457 | 1689 - 1735 | 1689 - 1735 | 1689 - 1735 | 1901 - 1940 | 2278 - 2313 | 2278 - 2313 |

MEFA-6 ANTIGEN

C

| hSOD-(1-154) | E1 | E2 | c33c | 5-1-1 type 1 | 5-1-1 type 3 | 5-1-1 type 2 | C-100 | NS5 | NS5 | CORE | CORE |
|---|---|---|---|---|---|---|---|---|---|---|---|
| AMINO ACIDS | 303 - 320 | 405 - 444 | 1192 - 1457 | 1689 - 1735 | 1689 - 1735 | 1689 - 1735 | 1901 - 1940 | 2278 - 2313 | 2278 - 2313 | 10 - 53 | 10 - 53 |

*FIG. 6*

SEQUENCE LISTING

```
<160> NUMBER OF SEQ ID NOS: 7

<210> SEQ ID NO 1
<211> LENGTH: 2058
<212> TYPE: DNA
<213> ORGANISM: Artificial Sequence
<220> FEATURE:
<223> OTHER INFORMATION: Description of Artificial Sequence:
      representative NS3/4a conformational antigen
<220> FEATURE:
<221> NAME/KEY: CDS
<222> LOCATION: (1)..(2058)

<400> SEQUENCE: 1

atg gcg ccc atc acg gcg tac gcc cag cag aca agg ggc ctc cta ggg       48
Met Ala Pro Ile Thr Ala Tyr Ala Gln Gln Thr Arg Gly Leu Leu Gly
  1               5                  10                  15

tgc ata atc acc agc cta act ggc cgg gac aaa aac caa gtg gag ggt       96
Cys Ile Ile Thr Ser Leu Thr Gly Arg Asp Lys Asn Gln Val Glu Gly
             20                  25                  30

gag gtc cag att gtg tca act gct gcc caa acc ttc ctg gca acg tgc      144
Glu Val Gln Ile Val Ser Thr Ala Ala Gln Thr Phe Leu Ala Thr Cys
         35                  40                  45

atc aat ggg gtg tgc tgg act gtc tac cac ggg gcc gga acg agg acc      192
Ile Asn Gly Val Cys Trp Thr Val Tyr His Gly Ala Gly Thr Arg Thr
     50                  55                  60

atc gcg tca ccc aag ggt cct gtc atc cag atg tat acc aat gta gac      240
Ile Ala Ser Pro Lys Gly Pro Val Ile Gln Met Tyr Thr Asn Val Asp
 65                  70                  75                  80

caa gac ctt gtg ggc tgg ccc gct ccg caa ggt agc cga tca ttg aca      288
Gln Asp Leu Val Gly Trp Pro Ala Pro Gln Gly Ser Arg Ser Leu Thr
                 85                  90                  95

ccc tgc act tgc ggc tcc tcg gac ctt tac ctg gtc acg agg cac gcc      336
Pro Cys Thr Cys Gly Ser Ser Asp Leu Tyr Leu Val Thr Arg His Ala
            100                 105                 110
```

-continued

```
gat gtc att ccc gtg cgc cgg cgg ggt gat agc agg ggc agc ctg ctg      384
Asp Val Ile Pro Val Arg Arg Arg Gly Asp Ser Arg Gly Ser Leu Leu
        115                 120                 125

tcg ccc cgg ccc att tcc tac ttg aaa ggc tcc tcg ggg ggt ccg ctg      432
Ser Pro Arg Pro Ile Ser Tyr Leu Lys Gly Ser Ser Gly Gly Pro Leu
    130                 135                 140

ttg tgc ccc gcg ggg cac gcc gtg ggc ata ttt agg gcc gcg gtg tgc      480
Leu Cys Pro Ala Gly His Ala Val Gly Ile Phe Arg Ala Ala Val Cys
145                 150                 155                 160

acc cgt gga gtg gct aag gcg gtg gac ttt atc cct gtg gag aac cta      528
Thr Arg Gly Val Ala Lys Ala Val Asp Phe Ile Pro Val Glu Asn Leu
                165                 170                 175

gag aca acc atg agg tcc ccg gtg ttc acg gat aac tcc tct cca cca      576
Glu Thr Thr Met Arg Ser Pro Val Phe Thr Asp Asn Ser Ser Pro Pro
            180                 185                 190

gta gtg ccc cag agc ttc cag gtg gct cac ctc cat gct ccc aca ggc      624
Val Val Pro Gln Ser Phe Gln Val Ala His Leu His Ala Pro Thr Gly
        195                 200                 205

agc ggc aaa agc acc aag gtc ccg gct gca tat gca gct cag ggc tat      672
Ser Gly Lys Ser Thr Lys Val Pro Ala Ala Tyr Ala Ala Gln Gly Tyr
    210                 215                 220

aag gtg cta gta ctc aac ccc tct gtt gct gca aca ctg ggc ttt ggt      720
Lys Val Leu Val Leu Asn Pro Ser Val Ala Ala Thr Leu Gly Phe Gly
225                 230                 235                 240

gct tac atg tcc aag gct cat ggg atc gat cct aac atc agg acc ggg      768
Ala Tyr Met Ser Lys Ala His Gly Ile Asp Pro Asn Ile Arg Thr Gly
                245                 250                 255

gtg aga aca att acc act ggc agc ccc atc acg tac tcc acc tac ggc      816
Val Arg Thr Ile Thr Thr Gly Ser Pro Ile Thr Tyr Ser Thr Tyr Gly
            260                 265                 270

aag ttc ctt gcc gac ggc ggg tgc tcg ggg ggc gct tat gac ata ata      864
Lys Phe Leu Ala Asp Gly Gly Cys Ser Gly Gly Ala Tyr Asp Ile Ile
        275                 280                 285

att tgt gac gag tgc cac tcc acg gat gcc aca tcc atc ttg ggc att      912
Ile Cys Asp Glu Cys His Ser Thr Asp Ala Thr Ser Ile Leu Gly Ile
    290                 295                 300

ggc act gtc ctt gac caa gca gag act gcg ggg gcg aga ctg gtt gtg      960
Gly Thr Val Leu Asp Gln Ala Glu Thr Ala Gly Ala Arg Leu Val Val
305                 310                 315                 320

ctc gcc acc gcc acc cct ccg ggc tcc gtc act gtg ccc cat ccc aac     1008
Leu Ala Thr Ala Thr Pro Pro Gly Ser Val Thr Val Pro His Pro Asn
                325                 330                 335

atc gag gag gtt gct ctg tcc acc acc gga gag atc cct ttt tac ggc     1056
Ile Glu Glu Val Ala Leu Ser Thr Thr Gly Glu Ile Pro Phe Tyr Gly
            340                 345                 350

aag gct atc ccc ctc gaa gta atc aag ggg ggg aga cat ctc atc ttc     1104
Lys Ala Ile Pro Leu Glu Val Ile Lys Gly Gly Arg His Leu Ile Phe
        355                 360                 365

tgt cat tca aag aag aag tgc gac gaa ctc gcc gca aag ctg gtc gca     1152
Cys His Ser Lys Lys Lys Cys Asp Glu Leu Ala Ala Lys Leu Val Ala
    370                 375                 380

ttg ggc atc aat gcc gtg gcc tac tac cgc ggt ctt gac gtg tcc gtc     1200
Leu Gly Ile Asn Ala Val Ala Tyr Tyr Arg Gly Leu Asp Val Ser Val
385                 390                 395                 400

atc ccg ccc atc ggc gat gtt gtc gtc gtg gca acc gat gcc ctc atg     1248
Ile Pro Pro Ile Gly Asp Val Val Val Val Ala Thr Asp Ala Leu Met
                405                 410                 415

acc ggc tat acg ggc gac ttc gac tcg gtg ata gac tgc aat acg tgt     1296
Thr Gly Tyr Thr Gly Asp Phe Asp Ser Val Ile Asp Cys Asn Thr Cys
            420                 425                 430
```

-continued

```
gtc acc cag aca gtc gat ttc agc ctt gac cct acc ttc acc att gag     1344
Val Thr Gln Thr Val Asp Phe Ser Leu Asp Pro Thr Phe Thr Ile Glu
        435                 440                 445

aca atc acg ctc ccc caa gat gct gtc tcc cgc act caa cgt cgg ggc     1392
Thr Ile Thr Leu Pro Gln Asp Ala Val Ser Arg Thr Gln Arg Arg Gly
    450                 455                 460

agg act ggc agg ggg aag cca ggc atc tac aga ttt gtg gca ccg ggg     1440
Arg Thr Gly Arg Gly Lys Pro Gly Ile Tyr Arg Phe Val Ala Pro Gly
465                 470                 475                 480

gag cgc ccc tcc ggc atg ttc gac tcg tcc gtc ctc tgt gag tgc tat     1488
Glu Arg Pro Ser Gly Met Phe Asp Ser Ser Val Leu Cys Glu Cys Tyr
                485                 490                 495

gac gca ggc tgt gct tgg tat gag ctc acg ccc gcc gag act aca gtt     1536
Asp Ala Gly Cys Ala Trp Tyr Glu Leu Thr Pro Ala Glu Thr Thr Val
            500                 505                 510

agg cta cga gcg tac atg aac acc ccg ggg ctt ccc gtg tgc cag gac     1584
Arg Leu Arg Ala Tyr Met Asn Thr Pro Gly Leu Pro Val Cys Gln Asp
        515                 520                 525

cat ctt gaa ttt tgg gag ggc gtc ttt aca ggc ctc act cat ata gat     1632
His Leu Glu Phe Trp Glu Gly Val Phe Thr Gly Leu Thr His Ile Asp
    530                 535                 540

gcc cac ttt cta tcc cag aca aag cag agt ggg gag aac ctt cct tac     1680
Ala His Phe Leu Ser Gln Thr Lys Gln Ser Gly Glu Asn Leu Pro Tyr
545                 550                 555                 560

ctg gta gcg tac caa gcc acc gtg tgc gct agg gct caa gcc cct ccc     1728
Leu Val Ala Tyr Gln Ala Thr Val Cys Ala Arg Ala Gln Ala Pro Pro
                565                 570                 575

cca tcg tgg gac cag atg tgg aag tgt ttg att cgc ctc aag ccc acc     1776
Pro Ser Trp Asp Gln Met Trp Lys Cys Leu Ile Arg Leu Lys Pro Thr
            580                 585                 590

ctc cat ggg cca aca ccc ctg cta tac aga ctg ggc gct gtt cag aat     1824
Leu His Gly Pro Thr Pro Leu Leu Tyr Arg Leu Gly Ala Val Gln Asn
        595                 600                 605

gaa atc acc ctg acg cac cca gtc acc aaa tac atc atg aca tgc atg     1872
Glu Ile Thr Leu Thr His Pro Val Thr Lys Tyr Ile Met Thr Cys Met
    610                 615                 620

tcg gcc gac ctg gag gtc gtc acg agc acc tgg gtg ctc gtt ggc ggc     1920
Ser Ala Asp Leu Glu Val Val Thr Ser Thr Trp Val Leu Val Gly Gly
625                 630                 635                 640

gtc ctg gct gct ttg gcc gcg tat tgc ctg tca aca ggc tgc gtg gtc     1968
Val Leu Ala Ala Leu Ala Ala Tyr Cys Leu Ser Thr Gly Cys Val Val
                645                 650                 655

ata gtg ggc agg gtc gtc ttg tcc ggg aag ccg gca atc ata cct gac     2016
Ile Val Gly Arg Val Val Leu Ser Gly Lys Pro Ala Ile Ile Pro Asp
            660                 665                 670

agg gaa gtc ctc tac cga gag ttc gat gag atg gaa gag tgc             2058
Arg Glu Val Leu Tyr Arg Glu Phe Asp Glu Met Glu Glu Cys
        675                 680                 685
```

```
<210> SEQ ID NO 2
<211> LENGTH: 686
<212> TYPE: PRT
<213> ORGANISM: Artificial Sequence
<220> FEATURE:
<223> OTHER INFORMATION: Description of Artificial Sequence:
      representative NS3/4a conformational antigen
```

-continued

<400> SEQUENCE: 2

```
Met Ala Pro Ile Thr Ala Tyr Ala Gln Gln Thr Arg Gly Leu Leu Gly
  1               5                  10                  15

Cys Ile Ile Thr Ser Leu Thr Gly Arg Asp Lys Asn Gln Val Glu Gly
             20                  25                  30

Glu Val Gln Ile Val Ser Thr Ala Ala Gln Thr Phe Leu Ala Thr Cys
         35                  40                  45

Ile Asn Gly Val Cys Trp Thr Val Tyr His Gly Ala Gly Thr Arg Thr
     50                  55                  60

Ile Ala Ser Pro Lys Gly Pro Val Ile Gln Met Tyr Thr Asn Val Asp
 65                  70                  75                  80

Gln Asp Leu Val Gly Trp Pro Ala Pro Gln Gly Ser Arg Ser Leu Thr
                 85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Ser Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Asn Leu
                165                 170                 175

Glu Thr Thr Met Arg Ser Pro Val Phe Thr Asp Asn Ser Ser Pro Pro
            180                 185                 190

Val Val Pro Gln Ser Phe Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Leu Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Val Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Val Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Ile Asn Ala Val Ala Tyr Tyr Arg Gly Leu Asp Val Ser Val
385                 390                 395                 400

Ile Pro Pro Ile Gly Asp Val Val Val Val Ala Thr Asp Ala Leu Met
                405                 410                 415
```

-continued

```
Thr Gly Tyr Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Ile Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Val Val Leu Ser Gly Lys Pro Ala Ile Ile Pro Asp
            660                 665                 670

Arg Glu Val Leu Tyr Arg Glu Phe Asp Glu Met Glu Glu Cys
        675                 680                 685


<210> SEQ ID NO 3
<211> LENGTH: 3297
<212> TYPE: DNA
<213> ORGANISM: Artificial Sequence
<220> FEATURE:
<223> OTHER INFORMATION: Description of Artificial Sequence:  MEFA 7.1
<220> FEATURE:
<221> NAME/KEY: CDS
<222> LOCATION: (1)..(3297)

<400> SEQUENCE: 3

atg gct aca aag gct gtt tgt gtt ttg aag ggt gac ggc cca gtt caa       48
Met Ala Thr Lys Ala Val Cys Val Leu Lys Gly Asp Gly Pro Val Gln
  1               5                  10                  15

ggt att att aac ttc gag cag aag gaa agt aat gga cca gtg aag gtg       96
Gly Ile Ile Asn Phe Glu Gln Lys Glu Ser Asn Gly Pro Val Lys Val
             20                  25                  30

tgg gga agc att aaa gga ctg act gaa ggc ctg cat gga ttc cat gtt      144
Trp Gly Ser Ile Lys Gly Leu Thr Glu Gly Leu His Gly Phe His Val
         35                  40                  45

cat gag ttt gga gat aat aca gca ggc tgt acc agt gca ggt cct cac      192
His Glu Phe Gly Asp Asn Thr Ala Gly Cys Thr Ser Ala Gly Pro His
     50                  55                  60
```

-continued

```
ttt aat cct cta tcc aga aaa cac ggt ggg cca aag gat gaa gag agg      240
Phe Asn Pro Leu Ser Arg Lys His Gly Gly Pro Lys Asp Glu Glu Arg
 65                 70                  75                  80

cat gtt gga gac ttg ggc aat gtg act gct gac aaa gat ggt gtg gcc      288
His Val Gly Asp Leu Gly Asn Val Thr Ala Asp Lys Asp Gly Val Ala
                85                  90                  95

gat gtg tct att gaa gat tct gtg atc tca ctc tca gga gac cat tgc      336
Asp Val Ser Ile Glu Asp Ser Val Ile Ser Leu Ser Gly Asp His Cys
            100                 105                 110

atc att ggc cgc aca ctg gtg gtc cat gaa aaa gca gat gac ttg ggc      384
Ile Ile Gly Arg Thr Leu Val Val His Glu Lys Ala Asp Asp Leu Gly
        115                 120                 125

aaa ggt gga aat gaa gaa agt aca aag aca gga aac gct gga agt cgt      432
Lys Gly Gly Asn Glu Glu Ser Thr Lys Thr Gly Asn Ala Gly Ser Arg
    130                 135                 140

ttg gct tgt ggt gta att ggg atc gcc cag aat ttg aat tct ggt tgc      480
Leu Ala Cys Gly Val Ile Gly Ile Ala Gln Asn Leu Asn Ser Gly Cys
145                 150                 155                 160

aat tgc tct atc tat ccc ggc cat ata acg ggt cac cgc atg gca tgg      528
Asn Cys Ser Ile Tyr Pro Gly His Ile Thr Gly His Arg Met Ala Trp
                165                 170                 175

aag ctt ggt tcc gcc gcc aga act acc tcg ggc ttt gtc tcc ttg ttc      576
Lys Leu Gly Ser Ala Ala Arg Thr Thr Ser Gly Phe Val Ser Leu Phe
            180                 185                 190

gcc cca ggt gcc aaa caa aac gaa act cac gtc acg gga ggc gca gcc      624
Ala Pro Gly Ala Lys Gln Asn Glu Thr His Val Thr Gly Gly Ala Ala
        195                 200                 205

gcc cga act acg tct ggg ttg acc tct ttg ttc tcc cca ggt gcc agc      672
Ala Arg Thr Thr Ser Gly Leu Thr Ser Leu Phe Ser Pro Gly Ala Ser
    210                 215                 220

caa aac att caa ttg att gtc gac ttt atc cct gtg gag aac cta gag      720
Gln Asn Ile Gln Leu Ile Val Asp Phe Ile Pro Val Glu Asn Leu Glu
225                 230                 235                 240

aca acc atg cga tct ccg gtg ttc acg gat aac tcc tct cca cca gta      768
Thr Thr Met Arg Ser Pro Val Phe Thr Asp Asn Ser Ser Pro Pro Val
                245                 250                 255

gtg ccc cag agc ttc cag gtg gct cac ctc cat gct ccc aca ggc agc      816
Val Pro Gln Ser Phe Gln Val Ala His Leu His Ala Pro Thr Gly Ser
            260                 265                 270

ggc aaa agc acc aag gtc ccg gct gca tat gca gct cag ggc tat aag      864
Gly Lys Ser Thr Lys Val Pro Ala Ala Tyr Ala Ala Gln Gly Tyr Lys
        275                 280                 285

gtg cta gta ctc aac ccc tct gtt gct gca aca ctg ggc ttt ggt gct      912
Val Leu Val Leu Asn Pro Ser Val Ala Ala Thr Leu Gly Phe Gly Ala
    290                 295                 300

tac atg tcc aag gct cat ggg atc gat cct aac atc agg acc ggg gtg      960
Tyr Met Ser Lys Ala His Gly Ile Asp Pro Asn Ile Arg Thr Gly Val
305                 310                 315                 320

aga aca att acc act ggc agc ccc atc acg tac tcc acc tac ggc aag     1008
Arg Thr Ile Thr Thr Gly Ser Pro Ile Thr Tyr Ser Thr Tyr Gly Lys
                325                 330                 335

ttc ctt gcc gac ggc ggg tgc tcg ggg ggc gct tat gac ata ata att     1056
Phe Leu Ala Asp Gly Gly Cys Ser Gly Gly Ala Tyr Asp Ile Ile Ile
            340                 345                 350

tgt gac gag tgc cac tcc acg gat gcc aca tcc atc ttg ggc att ggc     1104
Cys Asp Glu Cys His Ser Thr Asp Ala Thr Ser Ile Leu Gly Ile Gly
        355                 360                 365

act gtc ctt gac caa gca gag act gcg ggg gcg aga ctg gtt gtg ctc     1152
Thr Val Leu Asp Gln Ala Glu Thr Ala Gly Ala Arg Leu Val Val Leu
    370                 375                 380
```

-continued

```
gcc acc gcc acc cct ccg ggc tcc gtc act gtg ccc cat ccc aac atc      1200
Ala Thr Ala Thr Pro Pro Gly Ser Val Thr Val Pro His Pro Asn Ile
385                 390                 395                 400

gag gag gtt gct ctg tcc acc acc gga gag atc cct ttt tac ggc aag      1248
Glu Glu Val Ala Leu Ser Thr Thr Gly Glu Ile Pro Phe Tyr Gly Lys
                405                 410                 415

gct atc ccc ctc gaa gta atc aag ggg ggg aga cat ctc atc ttc tgt      1296
Ala Ile Pro Leu Glu Val Ile Lys Gly Gly Arg His Leu Ile Phe Cys
            420                 425                 430

cat tca aag aag aag tgc gac gaa ctc gcc gca aag ctg gtc gca ttg      1344
His Ser Lys Lys Lys Cys Asp Glu Leu Ala Ala Lys Leu Val Ala Leu
        435                 440                 445

ggc atc aat gcc gtg gcc tac tac cgc ggt ctt gac gtg tcc gtc atc      1392
Gly Ile Asn Ala Val Ala Tyr Tyr Arg Gly Leu Asp Val Ser Val Ile
    450                 455                 460

ccg acc agc ggc gat gtt gtc gtc gtg gca acc gat gcc ctc atg acc      1440
Pro Thr Ser Gly Asp Val Val Val Val Ala Thr Asp Ala Leu Met Thr
465                 470                 475                 480

ggc tat acc ggc gac ttc gac tcg gtg ata gac tgc aat acg tgt gtc      1488
Gly Tyr Thr Gly Asp Phe Asp Ser Val Ile Asp Cys Asn Thr Cys Val
                485                 490                 495

acc cag aca gtc gat ttc agc ctt gac cct acc ttc acc att gag aca      1536
Thr Gln Thr Val Asp Phe Ser Leu Asp Pro Thr Phe Thr Ile Glu Thr
            500                 505                 510

atc acg ctc ccc caa gat gct gtc tcc cgc act caa cgt cgg ggc agg      1584
Ile Thr Leu Pro Gln Asp Ala Val Ser Arg Thr Gln Arg Arg Gly Arg
        515                 520                 525

act ggc agg ggg aag cca ggc atc tac aga ttt gtg gca ccg ggg gag      1632
Thr Gly Arg Gly Lys Pro Gly Ile Tyr Arg Phe Val Ala Pro Gly Glu
    530                 535                 540

cgc ccc tcc ggc atg ttc gac tcg tcc gtc ctc tgt gag tgc tat gac      1680
Arg Pro Ser Gly Met Phe Asp Ser Ser Val Leu Cys Glu Cys Tyr Asp
545                 550                 555                 560

gca ggc tgt gct tgg tat gag ctc acg ccc gcc gag act aca gtt agg      1728
Ala Gly Cys Ala Trp Tyr Glu Leu Thr Pro Ala Glu Thr Thr Val Arg
                565                 570                 575

cta cga gcg tac atg aac acc ccg ggg ctt ccc gtg tgc cag gac cat      1776
Leu Arg Ala Tyr Met Asn Thr Pro Gly Leu Pro Val Cys Gln Asp His
            580                 585                 590

ctt gaa ttt tgg gag ggc gtc ttt aca ggc ctc act cat ata gat gcc      1824
Leu Glu Phe Trp Glu Gly Val Phe Thr Gly Leu Thr His Ile Asp Ala
        595                 600                 605

cac ttt cta tcc cag aca aag cag agt ggg gag aac ctt cct tac ctg      1872
His Phe Leu Ser Gln Thr Lys Gln Ser Gly Glu Asn Leu Pro Tyr Leu
    610                 615                 620

gta gcg tac caa gcc acc gtg tgc gct agg gct caa gcc cct ccc cca      1920
Val Ala Tyr Gln Ala Thr Val Cys Ala Arg Ala Gln Ala Pro Pro Pro
625                 630                 635                 640

tcg tgg gac cag atg tgg aag tgt ttg att cgc ctc aag ccc acc ctc      1968
Ser Trp Asp Gln Met Trp Lys Cys Leu Ile Arg Leu Lys Pro Thr Leu
                645                 650                 655

cat ggg cca aca ccc ctg cta tac aga ctg ggc gct gtt cag aat gaa      2016
His Gly Pro Thr Pro Leu Leu Tyr Arg Leu Gly Ala Val Gln Asn Glu
            660                 665                 670

atc acc ctg acg cac cca gtc acc aaa tac atc atg aca tgc atg tcg      2064
Ile Thr Leu Thr His Pro Val Thr Lys Tyr Ile Met Thr Cys Met Ser
        675                 680                 685

gcc gac ctg gag gtc gtc acg agc gca tgc tcc ggg aag ccg gca atc      2112
Ala Asp Leu Glu Val Val Thr Ser Ala Cys Ser Gly Lys Pro Ala Ile
    690                 695                 700
```

-continued

```
ata cct gac agg gaa gtc ctc tac cga gag ttc gat gag atg gaa gag      2160
Ile Pro Asp Arg Glu Val Leu Tyr Arg Glu Phe Asp Glu Met Glu Glu
705                 710                 715                 720

tgc tct cag cac tta ccg tac atc gag caa ggg atg atg ctc gcc gag      2208
Cys Ser Gln His Leu Pro Tyr Ile Glu Gln Gly Met Met Leu Ala Glu
                725                 730                 735

cag ttc aag cag aag gcc ctc ggc ctc tcg cga ggg ggc aag ccg gca      2256
Gln Phe Lys Gln Lys Ala Leu Gly Leu Ser Arg Gly Gly Lys Pro Ala
            740                 745                 750

atc gtt cca gac aaa gag gtg ttg tat caa caa tac gat gag atg gaa      2304
Ile Val Pro Asp Lys Glu Val Leu Tyr Gln Gln Tyr Asp Glu Met Glu
        755                 760                 765

gag tgc tca caa gct gcc cca tat atc gaa caa gct cag gta ata gct      2352
Glu Cys Ser Gln Ala Ala Pro Tyr Ile Glu Gln Ala Gln Val Ile Ala
    770                 775                 780

cac cag ttc aag gaa aaa gtc ctt gga ttg atc gat aat gat caa gtg      2400
His Gln Phe Lys Glu Lys Val Leu Gly Leu Ile Asp Asn Asp Gln Val
785                 790                 795                 800

gtt gtg act cct gac aaa gaa atc tta tat gag gcc ttt gat gag atg      2448
Val Val Thr Pro Asp Lys Glu Ile Leu Tyr Glu Ala Phe Asp Glu Met
                805                 810                 815

gaa gaa tgc gcc tcc aaa gcc gcc ctc att gag gaa ggg cag cgg atg      2496
Glu Glu Cys Ala Ser Lys Ala Ala Leu Ile Glu Glu Gly Gln Arg Met
            820                 825                 830

gcg gag atg ctc aag tct aag ata caa ggc ctc ctc ggg ata ctg cgc      2544
Ala Glu Met Leu Lys Ser Lys Ile Gln Gly Leu Leu Gly Ile Leu Arg
        835                 840                 845

cgg cac gtt ggt cct ggc gag ggg gca gtg cag tgg atg aac cgg ctg      2592
Arg His Val Gly Pro Gly Glu Gly Ala Val Gln Trp Met Asn Arg Leu
    850                 855                 860

ata gcc ttc gcc tcc aga ggg aac cat gtt tcc ccc acg cac tac gtt      2640
Ile Ala Phe Ala Ser Arg Gly Asn His Val Ser Pro Thr His Tyr Val
865                 870                 875                 880

ccg tct aga tcc cgg aga ttc gcc cag gcc ctg ccc gtt tgg gcg cgg      2688
Pro Ser Arg Ser Arg Arg Phe Ala Gln Ala Leu Pro Val Trp Ala Arg
                885                 890                 895

ccg gac tat aac ccc ccg cta gtg gag acg tgg aaa aag ccc gac tac      2736
Pro Asp Tyr Asn Pro Pro Leu Val Glu Thr Trp Lys Lys Pro Asp Tyr
            900                 905                 910

gaa cca cct gtg gtc cac ggc aga tct tct cgg aga ttc gcc cag gcc      2784
Glu Pro Pro Val Val His Gly Arg Ser Ser Arg Arg Phe Ala Gln Ala
        915                 920                 925

ctg ccc gtt tgg gcg cgg ccg gac tat aac ccc ccg cta gtg gag acg      2832
Leu Pro Val Trp Ala Arg Pro Asp Tyr Asn Pro Pro Leu Val Glu Thr
    930                 935                 940

tgg aaa aag ccc gac tac gaa cca cct gtg gtc cat ggc aga aag acc      2880
Trp Lys Lys Pro Asp Tyr Glu Pro Pro Val Val His Gly Arg Lys Thr
945                 950                 955                 960

aaa cgt aac acc aac cgg cgg ccg cag gac gtc aag ttc ccg ggt ggc      2928
Lys Arg Asn Thr Asn Arg Arg Pro Gln Asp Val Lys Phe Pro Gly Gly
                965                 970                 975

ggt cag atc gtt ggt cgc agg ggc cct cct atc ccc aag gct cgt cgg      2976
Gly Gln Ile Val Gly Arg Arg Gly Pro Pro Ile Pro Lys Ala Arg Arg
            980                 985                 990

ccc gag ggc agg acc tgg gct cag ccc ggt tac cct tgg ccc ctc tat      3024
Pro Glu Gly Arg Thr Trp Ala Gln Pro Gly Tyr Pro Trp Pro Leu Tyr
        995                 1000                1005

ggc aat aag gac aga cgg tct aca ggt aag tcc tgg ggt aag cca ggg      3072
Gly Asn Lys Asp Arg Arg Ser Thr Gly Lys Ser Trp Gly Lys Pro Gly
    1010                1015                1020
```

-continued

```
tac cct tgg cca aga aag acc aaa cgt aac acc aac cga cgg ccg cag     3120
Tyr Pro Trp Pro Arg Lys Thr Lys Arg Asn Thr Asn Arg Arg Pro Gln
1025                1030                1035                1040

gac gtc aag ttc ccg ggt ggc ggt cag atc gtt ggt cgc agg ggc cct     3168
Asp Val Lys Phe Pro Gly Gly Gly Gln Ile Val Gly Arg Arg Gly Pro
                1045                1050                1055

cct atc ccc aag gct cgt cgg ccc gag ggc agg acc tgg gct cag ccc     3216
Pro Ile Pro Lys Ala Arg Arg Pro Glu Gly Arg Thr Trp Ala Gln Pro
            1060                1065                1070

ggt tac cct tgg ccc ctc tat ggc aat aag gac aga cgg tct acc ggt     3264
Gly Tyr Pro Trp Pro Leu Tyr Gly Asn Lys Asp Arg Arg Ser Thr Gly
        1075                1080                1085

aag tcc tgg ggt aag cca ggg tat cct tgg ccc                         3297
Lys Ser Trp Gly Lys Pro Gly Tyr Pro Trp Pro
    1090                1095


<210> SEQ ID NO 4
<211> LENGTH: 1099
<212> TYPE: PRT
<213> ORGANISM: Artificial Sequence
<220> FEATURE:
<223> OTHER INFORMATION: Description of Artificial Sequence:  MEFA 7.1

<400> SEQUENCE: 4

Met Ala Thr Lys Ala Val Cys Val Leu Lys Gly Asp Gly Pro Val Gln
  1               5                  10                  15

Gly Ile Ile Asn Phe Glu Gln Lys Glu Ser Asn Gly Pro Val Lys Val
             20                  25                  30

Trp Gly Ser Ile Lys Gly Leu Thr Glu Gly Leu His Gly Phe His Val
         35                  40                  45

His Glu Phe Gly Asp Asn Thr Ala Gly Cys Thr Ser Ala Gly Pro His
     50                  55                  60

Phe Asn Pro Leu Ser Arg Lys His Gly Gly Pro Lys Asp Glu Glu Arg
 65                  70                  75                  80

His Val Gly Asp Leu Gly Asn Val Thr Ala Asp Lys Asp Gly Val Ala
                 85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln Asn Leu Asn Ser Gly Cys
145                 150                 155                 160

Asn Cys Ser Ile Tyr Pro Gly His Ile Thr Gly His Arg Met Ala Trp
                165                 170                 175

Lys Leu Gly Ser Ala Ala Arg Thr Thr Ser Gly Phe Val Ser Leu Phe
            180                 185                 190

Ala Pro Gly Ala Lys Gln Asn Glu Thr His Val Thr Gly Gly Ala Ala
        195                 200                 205

Ala Arg Thr Thr Ser Gly Leu Thr Ser Leu Phe Ser Pro Gly Ala Ser
    210                 215                 220

Gln Asn Ile Gln Leu Ile Val Asp Phe Ile Pro Val Glu Asn Leu Glu
225                 230                 235                 240

Thr Thr Met Arg Ser Pro Val Phe Thr Asp Asn Ser Ser Pro Pro Val
                245                 250                 255
```

-continued

```
Val Pro Gln Ser Phe Gln Val Ala His Leu His Ala Pro Thr Gly Ser
            260                 265                 270

Gly Lys Ser Thr Lys Val Pro Ala Ala Tyr Ala Ala Gln Gly Tyr Lys
        275                 280                 285

Val Leu Val Leu Asn Pro Ser Val Ala Ala Thr Leu Gly Phe Gly Ala
    290                 295                 300

Tyr Met Ser Lys Ala His Gly Ile Asp Pro Asn Ile Arg Thr Gly Val
305                 310                 315                 320

Arg Thr Ile Thr Thr Gly Ser Pro Ile Thr Tyr Ser Thr Tyr Gly Lys
                325                 330                 335

Phe Leu Ala Asp Gly Gly Cys Ser Gly Gly Ala Tyr Asp Ile Ile Ile
            340                 345                 350

Cys Asp Glu Cys His Ser Thr Asp Ala Thr Ser Ile Leu Gly Ile Gly
        355                 360                 365

Thr Val Leu Asp Gln Ala Glu Thr Ala Gly Ala Arg Leu Val Val Leu
    370                 375                 380

Ala Thr Ala Thr Pro Pro Gly Ser Val Thr Val Pro His Pro Asn Ile
385                 390                 395                 400

Glu Glu Val Ala Leu Ser Thr Thr Gly Glu Ile Pro Phe Tyr Gly Lys
                405                 410                 415

Ala Ile Pro Leu Glu Val Ile Lys Gly Gly Arg His Leu Ile Phe Cys
            420                 425                 430

His Ser Lys Lys Lys Cys Asp Glu Leu Ala Ala Lys Leu Val Ala Leu
        435                 440                 445

Gly Ile Asn Ala Val Ala Tyr Tyr Arg Gly Leu Asp Val Ser Val Ile
    450                 455                 460

Pro Thr Ser Gly Asp Val Val Val Val Ala Thr Asp Ala Leu Met Thr
465                 470                 475                 480

Gly Tyr Thr Gly Asp Phe Asp Ser Val Ile Asp Cys Asn Thr Cys Val
                485                 490                 495

Thr Gln Thr Val Asp Phe Ser Leu Asp Pro Thr Phe Thr Ile Glu Thr
            500                 505                 510

Ile Thr Leu Pro Gln Asp Ala Val Ser Arg Thr Gln Arg Arg Gly Arg
        515                 520                 525

Thr Gly Arg Gly Lys Pro Gly Ile Tyr Arg Phe Val Ala Pro Gly Glu
    530                 535                 540

Arg Pro Ser Gly Met Phe Asp Ser Ser Val Leu Cys Glu Cys Tyr Asp
545                 550                 555                 560

Ala Gly Cys Ala Trp Tyr Glu Leu Thr Pro Ala Glu Thr Thr Val Arg
                565                 570                 575

Leu Arg Ala Tyr Met Asn Thr Pro Gly Leu Pro Val Cys Gln Asp His
            580                 585                 590

Leu Glu Phe Trp Glu Gly Val Phe Thr Gly Leu Thr His Ile Asp Ala
        595                 600                 605

His Phe Leu Ser Gln Thr Lys Gln Ser Gly Glu Asn Leu Pro Tyr Leu
    610                 615                 620

Val Ala Tyr Gln Ala Thr Val Cys Ala Arg Ala Gln Ala Pro Pro Pro
625                 630                 635                 640

Ser Trp Asp Gln Met Trp Lys Cys Leu Ile Arg Leu Lys Pro Thr Leu
                645                 650                 655

His Gly Pro Thr Pro Leu Leu Tyr Arg Leu Gly Ala Val Gln Asn Glu
            660                 665                 670
```

-continued

```
Ile Thr Leu Thr His Pro Val Thr Lys Tyr Ile Met Thr Cys Met Ser
        675                 680                 685

Ala Asp Leu Glu Val Val Thr Ser Ala Cys Ser Gly Lys Pro Ala Ile
    690                 695                 700

Ile Pro Asp Arg Glu Val Leu Tyr Arg Glu Phe Asp Glu Met Glu Glu
705                 710                 715                 720

Cys Ser Gln His Leu Pro Tyr Ile Glu Gln Gly Met Met Leu Ala Glu
                725                 730                 735

Gln Phe Lys Gln Lys Ala Leu Gly Leu Ser Arg Gly Gly Lys Pro Ala
            740                 745                 750

Ile Val Pro Asp Lys Glu Val Leu Tyr Gln Gln Tyr Asp Glu Met Glu
        755                 760                 765

Glu Cys Ser Gln Ala Ala Pro Tyr Ile Glu Gln Ala Gln Val Ile Ala
    770                 775                 780

His Gln Phe Lys Glu Lys Val Leu Gly Leu Ile Asp Asn Asp Gln Val
785                 790                 795                 800

Val Val Thr Pro Asp Lys Glu Ile Leu Tyr Glu Ala Phe Asp Glu Met
                805                 810                 815

Glu Glu Cys Ala Ser Lys Ala Ala Leu Ile Glu Glu Gly Gln Arg Met
            820                 825                 830

Ala Glu Met Leu Lys Ser Lys Ile Gln Gly Leu Leu Gly Ile Leu Arg
        835                 840                 845

Arg His Val Gly Pro Gly Glu Gly Ala Val Gln Trp Met Asn Arg Leu
    850                 855                 860

Ile Ala Phe Ala Ser Arg Gly Asn His Val Ser Pro Thr His Tyr Val
865                 870                 875                 880

Pro Ser Arg Ser Arg Arg Phe Ala Gln Ala Leu Pro Val Trp Ala Arg
                885                 890                 895

Pro Asp Tyr Asn Pro Pro Leu Val Glu Thr Trp Lys Lys Pro Asp Tyr
            900                 905                 910

Glu Pro Pro Val Val His Gly Arg Ser Ser Arg Arg Phe Ala Gln Ala
        915                 920                 925

Leu Pro Val Trp Ala Arg Pro Asp Tyr Asn Pro Pro Leu Val Glu Thr
    930                 935                 940

Trp Lys Lys Pro Asp Tyr Glu Pro Pro Val Val His Gly Arg Lys Thr
945                 950                 955                 960

Lys Arg Asn Thr Asn Arg Arg Pro Gln Asp Val Lys Phe Pro Gly Gly
                965                 970                 975

Gly Gln Ile Val Gly Arg Arg Gly Pro Pro Ile Pro Lys Ala Arg Arg
            980                 985                 990

Pro Glu Gly Arg Thr Trp Ala Gln Pro Gly Tyr Pro Trp Pro Leu Tyr
        995                 1000                1005

Gly Asn Lys Asp Arg Arg Ser Thr Gly Lys Ser Trp Gly Lys Pro Gly
    1010                1015                1020

Tyr Pro Trp Pro Arg Lys Thr Lys Arg Asn Thr Asn Arg Arg Pro Gln
1025                1030                1035                1040

Asp Val Lys Phe Pro Gly Gly Gly Gln Ile Val Gly Arg Arg Gly Pro
                1045                1050                1055

Pro Ile Pro Lys Ala Arg Arg Pro Glu Gly Arg Thr Trp Ala Gln Pro
            1060                1065                1070
```

-continued

```
Gly Tyr Pro Trp Pro Leu Tyr Gly Asn Lys Asp Arg Arg Ser Thr Gly
        1075                1080                1085

Lys Ser Trp Gly Lys Pro Gly Tyr Pro Trp Pro
    1090                1095


<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 5

Gly Ser Ala Ala Arg Thr Thr Ser Gly Phe Val Ser Leu Phe Ala Pro
  1               5                  10                  15

Gly Ala Lys Gln Asn
             20


<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence:  ligated
      DNA piece

<400> SEQUENCE: 6

acaaaacaaa                                                            10


<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence:  NS4A
      peptide

<400> SEQUENCE: 7

Lys Lys Gly Ser Val Val Ile Val Gly Arg Ile Val Leu Ser Gly Lys
  1               5                  10                  15

Pro Ala Ile Ile Pro Lys Lys
             20
```

IMMUNOASSAYS FOR ANTI-HCV ANTIBODIES

CROSS-REFERENCE TO RELATED APPLICATIONS

This application is a continuation application of U.S. patent application Ser. No. 10/637,323, filed Aug. 8, 2003, now U.S. Pat. No. 6,797,809, which is a divisional of U.S. patent application Ser. No. 09/881,654, filed Jun. 14, 2001, now U.S. Pat. No. 6,632,601, from which applications priority is claimed pursuant to 35 USC §120 and which applications are related to provisional patent application Ser. Nos. 60/212,082, filed Jun. 15, 2000; 60/280,811, filed Apr. 2, 2001; and 60/280,867, filed Apr. 2, 2001, from which applications priority is claimed under 35 USC §119(e)(1) and which applications are incorporated herein by reference in their entireties.

TECHNICAL FIELD

The present invention pertains generally to viral diagnostics. In particular, the invention relates to immunoassays using multiple HCV antigens, for accurately diagnosing hepatitis C virus infection.

BACKGROUND OF THE INVENTION

Hepatitis C Virus (HCV) is the principal cause of parenteral non-A, non-B hepatitis (NANBH) which is transmitted largely through body blood transfusion and body fluid exchange. The virus is present in 0.4 to 2.0% of the general population in the United States. Chronic hepatitis develops in about 50% of infections and of these, approximately 20% of infected individuals develop liver cirrhosis which sometimes leads to hepatocellular carcinoma. Accordingly, the study and control of the disease is of medical importance.

HCV was first identified and characterized as a cause of NANBH by Houghten et al. The viral genomic sequence of HCV is known, as are methods for obtaining the sequence. See, e.g., International Publication Nos. WO 89/04669; WO 90/11089; and WO 90/14436. HCV has a 9.5 kb positive-sense, single-stranded RNA genome and is a member of the Flaviridae family of viruses. At least six distinct, but related genotypes of HCV, based on phylogenetic analyses, have been identified (Simmonds et al., *J. Gen. Virol.* (1993) 74:2391–2399). The virus encodes a single polyprotein having more than 3000 amino acid residues (Choo et al., *Science* (1989) 244:359–362; Choo et al., *Proc. Natl. Acad. Sci. USA* (1991) 88:2451–2455; Han et al., *Proc. Natl. Acad. Sci. USA* (1991) 88:1711–1715). The polyprotein is processed co- and post-translationally into both structural and non-structural (NS) proteins.

In particular, as shown in FIG. 1, several proteins are encoded by the HCV genome. The order and nomenclature of the cleavage products of the HCV polyprotein is as follows: $NH_2$-C-E1-E2-P7-NS2-NS3-NS4a-NS4b-NS5a-NS5b-COOH. Initial cleavage of the polyprotein is catalyzed by host proteases which liberate three structural proteins, the N-terminal nucleocapsid protein (termed "core") and two envelope glycoproteins, "E1" (also known as E) and "E2" (also known as E2/NS1), as well as nonstructural (NS) proteins that contain the viral enzymes. The NS regions are termed NS2, NS3, NS4, NS4a, NS4b, NS5a and NS5b. NS2 is an integral membrane protein with proteolytic activity. NS2, either alone or in combination with NS3, cleaves the NS2-NS3 sissle bond which in turn generates the NS3 N-terminus and releases a large polyprotein that includes both serine protease and RNA helicase activities. The NS3 protease serves to process the remaining polyprotein. Completion of polyprotein maturation is initiated by autocatalytic cleavage at the NS3-NS4a junction, catalyzed by the NS3 serine protease. Subsequent NS3-mediated cleavages of the HCV polyprotein appear to involve recognition of polyprotein cleavage junctions by an NS3 molecule of another polypeptide. In these reactions, NS3 liberates an NS3 cofactor (NS4a), NS4b and NS5a (NS5A has a phosphorylation function), and an RNA-dependent RNA polymerase (NS5b).

A number of general and specific polypeptides useful as immunological and diagnostic reagents for HCV, derived from the HCV polyprotein, have been described. See, e.g., Houghton et al., European Publication Nos. 318,216 and 388,232; Choo et al., *Science* (1989) 244:359–362; Kuo et al., *Science* (1989) 244:362–364; Houghton et al., *Hepatology* (1991) 14:381–388; Chien et al., *Proc. Natl. Acad. Sci. USA* (1992) 89:10011–10015; Chien et al., *J. Gastroent. Hepatol.* (1993) 8:S33–39; Chien et al., International Publication No. WO 93/00365; Chien, D. Y., International Publication No. WO 94/01778. These publications provide an extensive background on HCV generally, as well as on the manufacture and uses of HCV polypeptide immunological reagents. For brevity, therefore, the disclosure of these publications is incorporated herein by reference.

Sensitive, specific methods for screening and identifying carriers of HCV and HCV-contaminated blood or blood products would provide an important advance in medicine. Post-transfusion hepatitis (PTH) occurs in approximately 10% of transfused patients, and HCV has accounted for up to 90% of these cases. Patient care as well as the prevention and transmission of HCV by blood and blood products or by close personal contact require reliable diagnostic and prognostic tools. Accordingly, several assays have been developed for the serodiagnosis of HCV infection. See, e.g., Choo et al., *Science* (1989) 244:359–362; Kuo et al., *Science* (1989) 244:362–364; Choo et al., *Br. Med. Bull.* (1990) 46:423–441; Ebeling et al., *Lancet* (1990) 335:982–983; van der Poel et al., *Lancet* (1990) 335:558–560; van der Poel et al., *Lancet* (1991) 337:317–319; Chien, D. Y., International Publication No. WO 94/01778; Valenzuela et al., International Publication No. WO 97/44469; and Kashiwakuma et al., U.S. Pat. No. 5,871,904.

A significant problem encountered with some serum-based assays is that there is a significant gap between infection and detection of the virus, often exceeding 80 days. This assay gap may create great risk for blood transfusion recipients. To overcome this problem, nucleic acid-based tests (NAT) that detect viral RNA directly, and HCV core antigen tests that assay viral antigen instead of antibody response, have been developed. See, e.g., Kashiwakuma et al., U.S. Pat. No. 5,871,904.

However, there remains a need for sensitive, accurate diagnostic and prognostic tools in order to provide adequate patient care as well as to prevent transmission of HCV by blood and blood products or by close personal contact.

SUMMARY OF THE INVENTION

The present invention is based in part, on the finding that the use of NS3/4a conformational epitopes, in combination with multiple epitope fusion antigens, provides a sensitive and reliable method for detecting early HCV seroconversion. The assays described herein can also detect HCV infection caused by any of the six known genotypes of HCV. The use of multiple epitope fusion proteins also has the added advantages of decreasing masking problems, improving sensitivity in detecting antibodies by allowing a greater number of epitopes on a unit area of substrate, and improving selectivity.

Accordingly, in one embodiment, the subject invention is directed to an immunoassay solid support consisting essentially of at least one HCV NS3/4a conformational epitope and a multiple epitope fusion antigen, bound thereto, wherein said NS3/4a epitope and/or said multiple epitope fusion antigen react specifically with anti-HCV antibodies present in a biological sample from an HCV-infected individual.

The NS3/4a epitope may comprise the amino acid sequence depicted in FIGS. 3A–3D, or an amino acid sequence with at least 80% sequence identity thereto, or 90% sequence identity thereto, or at least 98% sequence identity thereto, or any integer in between, so long as the sequence has protease activity. In certain embodiments, the NS3/4a conformational epitope consists of the amino acid sequence depicted in FIGS. 3A–3D.

In additional embodiments, the multiple epitope fusion antigen comprises the amino acid sequence depicted in FIGS. 5A–5F, or an amino acid sequence with at least 80% sequence identity thereto, or 90% sequence identity thereto, or at least 98% sequence identity thereto, or any integer in between, so long as the sequence reacts specifically with anti-HCV antibodies present in a biological sample from an HCV-infected individual. In certain embodiments, the multiple epitope fusion antigen consists of the amino acid sequence depicted in FIGS. 5A–5F.

In yet another embodiment, the subject invention is directed to an immunoassay solid support consisting essentially of at least one HCV NS3/4a conformational epitope and a multiple epitope fusion antigen, bound thereto, wherein said NS3/4a conformational epitope comprises the amino acid sequence depicted in FIGS. 3A–3D, or an amino acid sequence with at least 80% sequence identity thereto which has protease activity, and said multiple epitope fusion antigen comprises the amino acid sequence depicted in FIGS. 5A–5F, or an amino acid sequence with at least 80% sequence identity, thereto which reacts specifically with anti-HCV antibodies present in a biological sample from an HCV-infected individual. In certain embodiments, the NS3/4a conformational epitope and the multiple epitope fusion antigen have at least 90%, 98% (or any integer between) sequence identity to the amino acid sequences of FIGS. 3A–3D and FIGS. 5A–5F, respectively, so long as the NS3/4a sequence has protease activity, and the multiple epitope fusion antigen reacts specifically with anti-HCV antibodies present in a biological sample from an HCV-infected individual. In certain embodiments, the NS3/4a conformational epitope consists of the amino acid sequence depicted in FIGS. 3A–3D, and the multiple epitope fusion antigen consists of the amino acid sequence depicted in FIGS. 5A–5F.

In another embodiment, the invention is directed to an immunoassay solid support consisting essentially of at least one HCV NS3/4a conformational epitope and a multiple epitope fusion antigen, bound thereto, wherein said NS3/4a conformational epitope consists of the amino acid sequence depicted in FIGS. 3A–3D, and said multiple epitope fusion antigen consists of the amino acid sequence depicted in FIGS. 5A–5F.

In still a further embodiment, the invention is directed to a method of detecting hepatitis C virus (HCV) infection in a biological sample, said method comprising:

(a) providing an immunoassay solid support as described above;

(b) combining a biological sample with said solid support under conditions which allow HCV antibodies, when present in the biological sample, to bind to said NS3/4a epitope and/or said multiple epitope fusion antigen to form a first immune complex;

(c) adding to the solid support from step (b) under complex forming conditions a detectably labeled antibody, wherein said labeled antibody is reactive with said immune complex;

(d) detecting second immune complexes formed between the detectably labeled antibody and the first immune complex, if any, as an indication of HCV infection in the biological sample.

In still a further embodiment, the invention is directed to a method of detecting hepatitis C virus (HCV) infection in a biological sample, said method comprising:

(a) providing an immunoassay solid support consisting essentially of at least one HCV NS3/4a conformational epitope and a multiple epitope fusion antigen, bound thereto, wherein said NS3/4a conformational epitope consists of the amino acid sequence depicted in FIGS. 3A–3D, and said multiple epitope fusion antigen consists of the amino acid sequence depicted in FIGS. 5A–5F;

(b) combining a biological sample with said solid support under conditions which allow HCV antibodies, when present in the biological sample, to bind to said NS3/4a epitope and/or said multiple epitope fusion antigen to form a first immune complex;

(c) adding to the solid support from step (b) under complex forming conditions a detectably labeled antibody, wherein said labeled antibody is reactive with said immune complex;

(d) detecting second immune complexes formed between the detectably labeled antibody and the first immune complex, if any, as an indication of HCV infection in the biological sample.

In another embodiment, the invention is directed to an immunodiagnostic test kit comprising an immunoassay solid support as described above, and instructions for conducting the immunodiagnostic test.

In another embodiment, the subject invention is directed to a method of producing an immunoassay solid support, comprising:

(a) providing a solid support; and (b) binding to the solid support at least one HCV NS3/4a conformational epitope and a multiple epitope fusion antigen, wherein said NS3/4a epitope and/or said multiple epitope fusion antigen react specifically with anti-HCV antibodies present in a biological sample from an HCV-infected individual.

In certain embodiments, the conformational epitope comprises the amino acid sequence depicted in FIGS. 3A–3D, or an amino acid sequence with at least 80% sequence identity thereto, or 90% sequence identity thereto, or at least 98% sequence identity thereto, or any integer in between, so long as the sequence has protease activity; and the multiple epitope fusion antigen comprises the amino acid sequence depicted in FIGS. 5A–5F, or an amino acid sequence with at least 80% sequence identity thereto, or 90% sequence identity thereto, or at least 98% sequence identity thereto, or any integer in between, so long as the sequence reacts specifically with anti-HCV antibodies present in a biological sample from an HCV-infected individual.

In still further embodiments, the NS3/4a conformational epitope consists of the amino acid sequence depicted in FIGS. 3A–3D and the multiple epitope fusion antigen consists of the amino acid sequence depicted in FIGS. 5A–5F.

In another embodiment, the invention is directed to a method of producing an immunoassay solid support, comprising:

(a) providing a solid support; and (b) binding to the solid support at least one HCV NS3/4a conformational epitope and a multiple epitope fusion antigen, wherein said NS3/4a conformational epitope consists of the amino acid sequence depicted in FIGS. 3A–3D, and said multiple epitope fusion antigen consists of the amino acid sequence depicted in FIGS. 5A–5F.

In still a further embodiment, the subject invention is directed to a multiple epitope fusion antigen comprising the amino acid sequence depicted in FIGS. 5A–5F, or an amino acid sequence with at least 80% sequence identity thereto, or 90% sequence identity thereto, or an amino acid sequence with at least 98% sequence identity thereto, or any integer in between, which sequence reacts specifically with anti-HCV antibodies present in a biological sample from an HCV-infected individual.

In certain embodiments, the multiple epitope fusion antigen consists of the amino acid sequence depicted in FIGS. 5A–5F.

In other embodiments, the invention is directed to a polynucleotide comprising a coding sequence for the multiple epitope fusion antigen, a recombinant vector comprising the polynucleotide and control elements operably linked to said polynucleotide whereby the coding sequence can be transcribed and translated in a host cell, a host cell transformed with the recombinant vector, and a method of producing a recombinant multiple epitope fusion antigen comprising providing a population of host cells as above and culturing said population of cells under conditions whereby the multiple epitope fusion antigen encoded by the coding sequence present in said recombinant vector is expressed.

These and other aspects of the present invention will become evident upon reference to the following detailed description and attached drawings. In addition, various references are set forth herein which describe in more detail certain procedures or compositions, and are therefore incorporated by reference in their entirety.

BRIEF DESCRIPTION OF THE DRAWINGS

FIGS. 3A through 3D depict the DNA (SEC ID NO:1) and corresponding amino acid (SEC ID NO:2) sequence of a representative NS3/4a conformational antigen for use in the present assays. The amino acids at positions 403 and 404 of FIGS. 3A through 3D represent substitutions of Pro for Thr, and Ile for Ser, of the native amino acid sequence of HCV-1.

FIGS. 5A–5F depict the DNA (SEC ID NO:3) and corresponding amino acid (SEC ID NO:4) sequence of MEFA 7.1.

FIGS. 6A–6C show representative MEFAs for use with the subject immunoassays. FIG. 6A is a diagrammatic representation of MEFA 3. FIG. 6B is a diagrammatic representation of MEFA 5. FIG. 6C is a diagrammatic representation of MEFA 6.

DETAILED DESCRIPTION OF THE INVENTION

Figure 1:
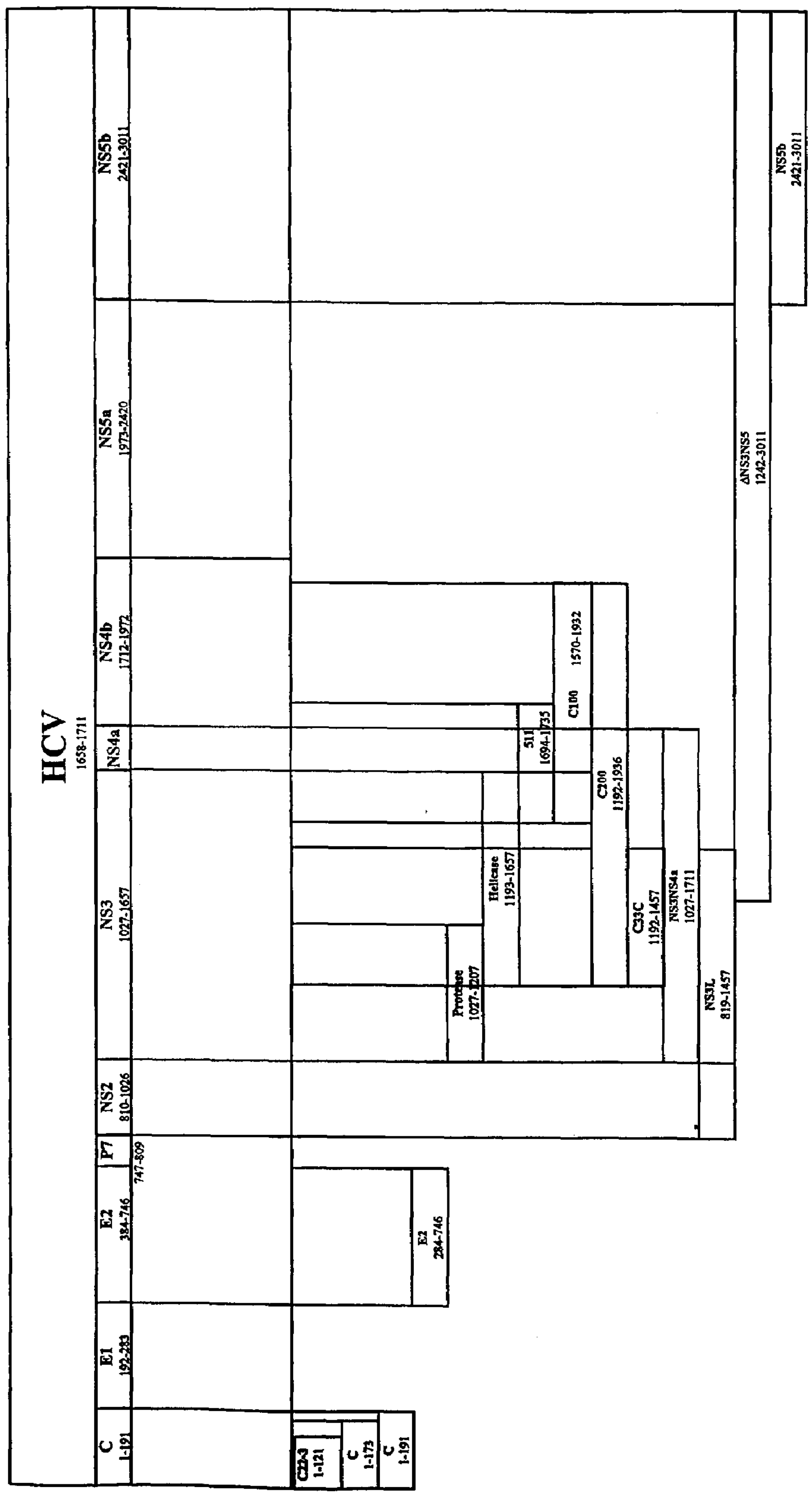
FIG. 1 is a diagrammatic representation of the HCV genome, depicting the various regions of the polyprotein from which the present assay reagents (proteins and antibodies) are derived.

The practice of the present invention will employ, unless otherwise indicated, conventional methods of chemistry, biochemistry, recombinant DNA techniques and immunology, within the skill of the art. Such techniques are explained fully in the literature. See, e.g., *Fundamental Virology,* 2nd Edition, vol. I & II (B. N. Fields and D. M. Knipe, eds.); *Handbook of Experimental Immunology*, Vols. I–IV (D. M. Weir and C. C. Blackwell eds., Blackwell Scientific Publications); T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entirety.

It must be noted that, as used in this specification and the appended claims, the singular forms. "a", "an" and "the" include plural referents unless the content clearly dictates otherwise. Thus, for example, reference to "an antigen" includes a mixture of two or more antigens, and the like.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

I. Definitions

In describing the present invention, the following terms will be employed, and are intended to be defined as indicated below.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

An HCV polypeptide is a polypeptide, as defined above, derived from the HCV polyprotein. The polypeptide need not be physically derived from HCV, but may be synthetically or recombinantly produced. Moreover, the polypeptide may be derived from any of the various HCV strains and isolates, such as, but not limited to, any of the isolates from strains 1, 2, 3, 4, 5 or 6 of HCV. A number of conserved and variable regions are known between these strains and, in general, the amino acid sequences of epitopes derived from these regions will have a high degree of sequence homology, e.g., amino acid sequence homology of more than 30%, preferably more than 40%, when the two sequences are aligned. Thus, for example, the term "NS3/4a" polypeptide refers to native NS3/4a from any of the various HCV strains, as well as NS3/4a analogs, muteins and immunogenic fragments, as defined further below. The complete genotypes of many of these strains are known. See, e.g., U.S. Pat. No. 6,150,087 and GenBank Accession Nos. AJ238800 and AJ238799.

The terms "analog" and "mutein" refer to biologically active derivatives of the reference molecule, or fragments of such derivatives, that retain desired activity, such as immunoreactivity in the assays described herein. In general, the term "analog" refers to compounds having a native polypeptide sequence and structure with one or more amino acid additions, substitutions (generally conservative in nature) and/or deletions, relative to the native molecule, so long as the modifications do not destroy immunogenic activity. The term "mutein" refers to peptides having one or more peptide mimics ("peptoids"), such as those described in International Publication No. WO 91/04282. Preferably, the analog or mutein has at least the same immunoactivity as the native molecule. Methods for making polypeptide analogs and muteins are known in the art and are described further below.

Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5–10 conservative or non-conservative amino acid substitutions, or even up to about 15–25 conservative or non-conservative amino acid substitutions, or any integer between 5–25, so long as the desired function of the molecule remains intact. One of skill in the art may readily determine regions of the molecule of interest that can tolerate change by reference to Hopp/Woods and Kyte-Doolittle plots, well known in the art.

By "fragment" is intended a polypeptide consisting of only a part of the intact full-length polypeptide sequence and structure. The fragment can include a C-terminal deletion and/or an N-terminal deletion of the native polypeptide. An "immunogenic fragment" of a particular HCV protein will generally include at least about 5–10 contiguous amino acid residues of the full-length molecule, preferably at least about 15–25 contiguous amino acid residues of the full-length molecule, and most preferably at least about 20–50 or more contiguous amino acid residues of the full-length molecule, that define an epitope, or any integer between 5 amino acids and the full-length sequence, provided that the fragment in question retains immunoreactivity in the assays described herein. For example, preferred immunogenic fragments, include but are not limited to fragments of HCV core that comprise, e.g., amino acids 10–45, 10–53, 67–88, and 120–130 of the polyprotein, epitope 5-1-1 (in the NS4a/NS4b region of the viral genome) as well as defined epitopes derived from any of the regions of the polyprotein shown in FIG. 1, such as but not limited to the E1, E2, NS3 (e.g., polypeptide c33c from the NS3 region), NS4 (e.g., polypeptide c100 from the NS3/NS4 regions), NS3/4a and NS5 regions of the HCV polyprotein, as well as any of the other various epitopes identified from the HCV polyprotein. See, e.g., Chien et al., *Proc. Natl. Acad. Sci. USA* (1992) 89:10011–10015; Chien et al., *J. Gastroent. Hepatol.* (1993) 8:S33–39; Chien et al., International Publication No. WO 93/00365; Chien, D. Y., International Publication No. WO 94/01778; U.S. Pat. Nos. 6,150,087 and 6,121,020, all of which are incorporated by reference herein in their entireties.

The term "epitope" as used herein refers to a sequence of at least about 3 to 5, preferably about 5 to 10 or 15, and not more than about 1,000 amino acids (or any integer therebetween), which define a sequence that by itself or as part of a larger sequence, binds to an antibody generated in response to such sequence. There is no critical upper limit to the length of the fragment, which may comprise nearly the full-length of the protein sequence, or even a fusion protein comprising two or more epitopes from the HCV polyprotein. An epitope for use in the subject invention is not limited to a polypeptide having the exact sequence of the portion of the parent protein from which it is derived. Indeed, viral genomes are in a state of constant flux and contain several variable domains which exhibit relatively high degrees of variability between isolates. Thus the term "epitope" encompasses sequences identical to the native sequence, as well as modifications to the native sequence, such as deletions, additions and substitutions (generally conservative in nature).

Regions of a given polypeptide that include an epitope can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998–4002; Geysen et al. (1985) *Proc. Natl. Acad. Sci. USA* 82:178–182; Geysen et al. (1986) *Molec. Immunol.* 23:709–715, all incorporated herein by reference in their entireties. Using such techniques, a number of epitopes of HCV have been identified. See, e.g., Chien et al., *Viral Hepatitis and Liver Disease* (1994) pp. 320–324, and further below. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci USA* (1981) 78:3824–3828 for determining antigenicity profiles, and the Kyte-Doolittle technique, Kyte et al., *J. Mol. Biol.* (1982) 157:105–132 for hydropathy plots.

As used herein, the term "conformational epitope" refers to a portion of a full-length protein, or an analog or mutein thereof, having structural features native to the amino acid sequence encoding the epitope within the full-length natural protein. Native structural features include, but are not limited to, glycosylation and three dimensional structure. The length of the epitope defining sequence can be subject to wide variations as these epitopes are believed to be formed by the three-dimensional shape of the antigen (e.g., folding). Thus, amino acids defining the epitope can be relatively few in number, but widely dispersed along the length of the molecule, being brought into correct epitope conformation via folding. The portions of the antigen between the residues defining the epitope may not be critical to the conformational structure of the epitope. For example, deletion or substitution of these intervening sequences may not affect the conformational epitope provided sequences critical to epitope conformation are maintained (e.g., cysteines involved in disulfide bonding, glycosylation sites, etc.).

Conformational epitopes present in the NS3/4a region are readily identified using methods discussed above. Moreover, the presence or absence of a conformational epitope in a given polypeptide can be readily determined through screening the antigen of interest with an antibody (polyclonal serum or monoclonal to the conformational epitope) and comparing its reactivity to that of a denatured version of the antigen which retains only linear epitopes (if any). In such screening using polyclonal antibodies, it may be advantageous to absorb the polyclonal serum first with the denatured antigen and see if it retains antibodies to the antigen of interest. Additionally, in the case of NS3/4a, a molecule which preserves the native conformation will also have protease and, optionally, helicase enzymatic activities. Such activities can be detected using enzymatic assays, as described further below.

Preferably, a conformational epitope is produced recombinantly and is expressed in a cell from which it is extractable under conditions which preserve its desired structural features, e.g. without denaturation of the epitope. Such cells include bacteria, yeast, insect, and mammalian cells. Expression and isolation of recombinant conformational epitopes from the HCV polyprotein are described in e.g., International Publication Nos. WO 96/04301, WO 94/01778, WO 95/33053, WO 92/08734, which applications are herein incorporated by reference in their entirety. Alternatively, it is possible to express the antigens and further renature the protein after recovery. It is also understood that chemical synthesis may also provide conformational antigen mimitopes that cross-react with the "native" antigen's conformational epitope.

The term "multiple epitope fusion antigen" or "MEFA" as used herein intends a polypeptide in which multiple HCV antigens are part of a single, continuous chain of amino acids, which chain does not occur in nature. The HCV antigens may be connected directly to each other by peptide bonds or may be separated by intervening amino acid sequences. The fusion antigens may also contain sequences exogenous to the HCV polyprotein. Moreover, the HCV sequences present may be from multiple genotypes and/or isolates of HCV. Examples of particular MEFAs for use in the present immunoassays are detailed in, e.g., International Publication No. WO 97/44469, incorporated herein by reference in its entirety, and are described further below.

An "antibody" intends a molecule that, through chemical or physical means, specifically binds to a polypeptide of interest. Thus, for example, an HCV core antibody is a molecule that specifically binds to the HCV core protein. The term "antibody" as used herein includes antibodies obtained from both polyclonal and monoclonal preparations, as well as, the following: hybrid (chimeric) antibody molecules (see, for example, Winter et al. (1991) *Nature* 349: 293–299; and U.S. Pat. No. 4,816,567); $F(ab')_2$ and F(ab) fragments; Fv molecules (non-covalent heterodimers, see, for example, Inbar et al. (1972) *Proc Natl Acad Sci USA* 69:2659–2662; and Ehrlich et al. (1980) *Biochem* 19:4091–4096); single-chain Fv molecules (sFv) (see, for example, Huston et al. (1988) *Proc Natl Acad Sci USA* 85:5879–5883); dimeric and trimeric antibody fragment constructs; minibodies (see, e.g., Pack et al. (1992) *Biochem* 31:1579–1584; Cumber et al. (1992) *J. Immunology* 149B: 120–126); humanized antibody molecules (see, for example, Riechmann et al. (1988) *Nature* 332:323–327; Verhoeyan et al. (1988) *Science* 239:1534–1536; and U.K. Patent Publication No. GB 2,276,169, published 21 Sep. 1994); and, any functional fragments obtained from such molecules, wherein such fragments retain immunological binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. Thus, the term encompasses antibodies obtained from murine hybridomas, as well as human monoclonal antibodies obtained using human rather than murine hybridomas. See, e.g., Cote, et al. *Monclonal Antibodies and Cancer Therapy,* Alan R. Liss, 1985, p. 77.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

By "equivalent antigenic determinant" is meant an antigenic determinant from different sub-species or strains of HCV, such as from strains 1, 2, or 3 of HCV. More specifically, epitopes are known, such as 5-1-1, and such epitopes vary between the strains 1, 2, and 3. Thus, the epitope 5-1-1 from the three different strains are equivalent antigenic determinants and thus are "copies" even though their sequences are not identical. In general the amino acid sequences of equivalent antigenic determinants will have a high degree of sequence homology, e.g., amino acid sequence homology of more than 30%, preferably more than 40%, when the two sequences are aligned.

"Homology" refers to the percent similarity between two polynucleotide or two polypeptide moieties. Two DNA, or two polypeptide sequences are "substantially homologous" to each other when the sequences exhibit at least about 50%, preferably at least about 75%, more preferably at least about 80%–85%, preferably at least about 90%, and most preferably at least about 95%–98% sequence similarity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100.

Readily available computer programs can be used to aid in the analysis of homology and identity, such as ALIGN, Dayhoff, M. O. in *Atlas of Protein Sequence and Structure* M. O. Dayhoff ed., 5 Suppl. 3:353–358, National biomedical Research Foundation, Washington, DC, which adapts the local homology algorithm of Smith and Waterman *Advances in Appl. Math.* 2:482–489, 1981 for peptide analysis. Programs for determining nucleotide sequence homology are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent homology of a particular nucleotide sequence to a reference sequence can be determined using the homology algorithm of Smith and Waterman with a default scoring table and a gap penalty of six nucleotide positions.

Another method of establishing percent homology in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence homology." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

A "coding sequence" or a sequence which "encodes" a selected polypeptide, is a nucleic acid molecule which is transcribed (in the case of DNA) and translated (in the case of MRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

"Operably linked" refers to an arrangement of elements wherein the components so described are configured so as to perform their desired function. Thus, a given promoter operably linked to a coding sequence is capable of effecting the expression of the coding sequence when the proper transcription factors, etc., are present. The promoter need not be contiguous with the coding sequence, so long as it functions to direct the expression thereof. Thus, for example, intervening untranslated yet transcribed sequences can be present between the promoter sequence and the coding sequence, as can transcribed introns, and the promoter sequence can still be considered "operably linked" to the coding sequence.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

A "control element" refers to a polynucleotide sequence which aids in the expression of a coding sequence to which it is linked. The term includes promoters, transcription termination sequences, upstream regulatory domains, polyadenylation signals, untranslated regions, including 5'-UTRs and 3'-UTRs and when appropriate, leader sequences and enhancers, which collectively provide for the transcription and translation of a coding sequence in a host cell.

A "promoter" as used herein is a DNA regulatory region capable of binding RNA polymerase in a host cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence is a transcription initiation site, as well as protein binding domains (consensus sequences) responsible for the binding of RNA polymerase. Eucaryotic promoters will often, but not always, contain "TATA" boxes and "CAT" boxes.

A control sequence "directs the transcription" of a coding sequence in a cell when RNA polymerase will bind the promoter sequence and transcribe the coding sequence into mRNA, which is then translated into the polypeptide encoded by the coding sequence.

"Expression cassette" or "expression construct" refers to an assembly which is capable of directing the expression of the sequence(s) or gene(s) of interest. The expression cassette includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

"Transformation," as used herein, refers to the insertion of an exogenous polynucleotide into a host cell, irrespective of the method used for insertion: for example, transformation by direct uptake, transfection, infection, and the like. For particular methods of transfection, see further below. The exogenous polynucleotide may be maintained as a nonintegrated vector, for example, an episome, or alternatively, may be integrated into the host genome.

A "host cell" is a cell which has been transformed, or is capable of transformation, by an exogenous DNA sequence.

As used herein, a "biological sample" refers to a sample of tissue or fluid isolated from a subject, that commonly includes antibodies produced by the subject. Typical samples that include such antibodies are known in the art and include but not limited to, blood, plasma, serum, fecal matter, urine, bone marrow, bile, spinal fluid, lymph fluid, samples of the skin, secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

"Common solid support" intends a single solid matrix to which the HCV polypeptides used in the subject immunoassays are bound covalently or by noncovalent means such as hydrophobic adsorption.

"Immunologically reactive" means that the antigen in question will react specifically with anti-HCV antibodies present in a biological sample from an HCV-infected individual.

"Immune complex" intends the combination formed when an antibody binds to an epitope on an antigen.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens) and the like. The term "fluorescer" refers to a substance or a portion thereof which is capable of exhibiting fluorescence in the detectable range. Particular examples of labels which may be used under the invention include, but are not limited to, horse radish peroxidase (HRP), fluorescein, FITC, rhodamine, dansyl, umbelliferone, dimethyl acridinium ester (DMAE), Texas red, luminol, NADPH and α-β-galactosidase.

II. Modes of Carrying out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

As noted above, the present invention is based on the discovery of novel diagnostic methods for accurately detecting early HCV infection. The methods rely on the identification and use of highly immunogenic HCV antigens which are present during the early stages of HCV seroconversion, thereby increasing detection accuracy and reducing the incidence of false results. In particular, the immunoassays described herein utilize highly immunogenic conformational epitopes derived from the NS3/4a region of the HCV polyprotein, and multiple epitope fusion antigens comprising various HCV polypeptides, either from the same or different HCV genotypes and isolates, such as multiple immunodominant epitopes, for example, major linear epitopes of HCV core, E1, E2, NS3, 5-1-1, c100-3 and NS5 sequences. The methods can be conveniently practiced in a single assay, using any of the several assay formats described below, such as but not limited to, assay formats which utilize a solid support to which the HCV antigens are bound.

The NS3/4a region of the HCV polyprotein has been described and the amino acid sequence and overall structure of the protein are disclosed in, e.g., Yao et al., *Structure* (November 1999) 7:1353–1363; Sali et al., *Biochem.* (1998) 37:3392–3401; and Bartenschlager, R., *J. Viral Hepat.* (1999) 6:165–181. See, also, Dasmahapatra et al., U.S. Pat. No. 5,843,752, incorporated herein by reference in its entirety. The subject immunoassays utilize at least one conformational epitope derived from the NS3/4a region that exists in the conformation as found in the naturally occurring HCV particle or its infective product, as evidenced by the preservation of protease and, optionally, helicase enzymatic activities normally displayed by the NS3/4a gene product and/or immunoreactivity of the antigen with antibodies in a biological sample from an HCV-infected subject, and a loss of the epitope's immunoreactivity upon denaturation of the antigen. For example, the conformational epitope can be disrupted by heating, changing the pH to extremely acid or basic, or by adding known organic denaturants, such as dithiothreitol (DTT) or an appropriate detergent. See, e.g., *Protein Purification Methods, a practical approach* (E. L. V. Harris and S. Angal eds., IRL Press) and the denatured product compared to the product which is not treated as above.

Protease and helicase activity may be determined using standard enzyme assays well known in the art. For example, protease activity may be determined using the procedure described below in the examples, as well as using assays well known in the art. See, e.g., Takeshita et al., *Anal Biochem.* (1997) 247:242–246; Kakiuchi et al., *J. Biochem.* (1997) 122:749–755; Sali et al., *Biochemistry* (1998) 37:3392–3401; Cho et al., *J. Virol. Meth.* (1998) 72:109–115; Cerretani et al., *Anal. Biochem.* (1999) 266: 192–197; Zhang et al., *Anal. Biochem.* (1999) 270:268–275; Kakiuchi et al., *J. Virol. Meth.* (1999) 80:77–84; Fowler et al., *J. Biomol. Screen.* (2000) 5:153–158; and Kim et al., *Anal. Biochem.* (2000) 284:42–48. Similarly, helicase activity assays are well known in the art and helicase activity of an NS3/4a epitope may be determined using, for example, an ELISA assay, as described in, e.g., Hsu et al., *Biochem. Biophys. Res. Commun.* (1998) 253:594–599; a scintillation proximity assay system, as described in Kyono et al., *Anal. Biochem.* (1998) 257:120–126; high throughput screening assays as described in, e.g., Hicham et al., *Antiviral Res.* (2000) 46:181–193 and Kwong et al., *Methods Mol. Med.* (2000) 24:97–116; as well as by other assay methods known in the art. See, e.g., Khu et al., *J. Virol.* (2001) 75:205–214; Utama et al., *Virology* (2000) 273:316–324; Paolini et al., *J. Gen. Virol.* (2000) 81:1335–1345; Preugschat et al., *Bio-*

*chemistry* (2000) 39:5174–5183; Preugschat et al., *Methods Mol. Med*. (1998) 19:353–364; and Hesson et al., *Biochemistry* (2000) 39:2619–2625.

The length of the antigen is sufficient to maintain an immunoreactive conformational epitope. Often, the polypeptide containing the antigen used will be almost full-length, however, the polypeptide may also be truncated to, for example, increase solubility or to improve secretion. Generally, the conformational epitope found in NS3/4a is expressed as a recombinant polypeptide in a cell and this polypeptide provides the epitope in a desired form, as described in detail below.

A representative amino acid sequence for the NS3/4a polypeptide is shown in FIGS. 3A through 3D. The amino acid sequence shown at positions 2–686 of the figure corresponds to amino acid positions 1027–1711 of HCV-1. An initiator codon (ATG) coding for Met, is shown as position 1. Additionally, the Thr normally occurring at position 1428 of HCV-1 (amino acid position 403 of FIG. 3) is mutated to Pro, and the Ser normally occurring at position 1429 of HCV-1 (amino acid position 404 of FIG. 3) is mutated to Ile. However, either the native sequence, with or without an N-terminal Met, the depicted analog, with or without the N-terminal Met, or other analogs and fragments can be used in the subject assays, so long as the epitope is produced using a method that retains or reinstates its native conformation such that protease activity, and optionally, helicase activity is retained. Dasmahapatra et al., U.S. Pat. No. 5,843,752 and Zhang et al., U.S. Pat. No. 5,990,276, both describe analogs of NS3/4a.

The NS3 protease of NS3/4a is found at about positions 1027–1207, numbered relative to HCV-1 (see, Choo et al., *Proc. Natl. Acad. Sci. USA* (1991) 88:2451–2455), positions 2–182 of FIG. 3. The structure of the NS3 protease and active site are known. See, e.g., De Francesco et al., *Antivir. Ther*. (1998) 3:99–109; Koch et al., *Biochemistry* (2001) 40:631–640. Changes to the native sequence that will normally be tolerated will be those outside of the active site of the molecule. Particularly, it is desirable to maintain amino acids 1- or 2–155 of FIG. 3, with little or only conservative substitutions. Amino acids occurring beyond 155 will tolerate greater changes. Additionally, if fragments of the NS3/4a sequence found in FIG. 3 are used, these fragments will generally include at least amino acids 1- or 2–155, preferably amino acids 1- or 2–175, and most preferably amino acids 1- or 2–182, with or without the N-terminal Met. The helicase domain is found at about positions 1193–1657 of HCV-1 (positions 207–632 of FIG. 3). Thus, if helicase activity is desired, this portion of the molecule will be maintained with little or only conservative changes. One of skill in the art can readily determine other regions that will tolerate change based on the known structure of NS3/4a.

The immunoassays described herein also utilize multiple epitope fusion antigens (termed "MEFAs"), as described in International Publication No. WO 97/44469. Such MEFAs include multiple epitopes derived from two or more of the various viral regions of the HCV polyprotein shown in FIG. 1 and Table 1. In particular, as shown in FIG. 1 and Table 1, An HCV polyprotein, upon cleavage, produces at least ten distinct products, in the order of $NH_2$- Core-E1-E2-p7-NS2-NS3-NS4a-NS4b-NS5a- NS5b-COOH. The core polypeptide occurs at positions 1–191, numbered relative to HCV-1 (see, Choo et al. (1991) *Proc. Natl. Acad. Sci. USA* 88:2451–2455, for the HCV-1 genome). This polypeptide is further processed to produce an HCV polypeptide with approximately amino acids 1–173. The envelope polypeptides, E1 and E2, occur at about positions 192–383 and 384–746, respectively. The P7 domain is found at about positions 747–809. NS2 is an integral membrane protein with proteolytic activity and is found at about positions 810–1026 of the polyprotein. NS2, either alone or in combination with NS3 (found at about positions 1027–1657), cleaves the NS2–NS3 sissle bond which in turn generates the NS3 N-terminus and releases a large polyprotein that includes both serine protease and RNA helicase activities. The NS3 protease, found at about positions 1027–1207, serves to process the remaining polyprotein. The helicase activity is found at about positions 1193–1657. Completion of polyprotein maturation is initiated by autocatalytic cleavage at the NS3–NS4a junction, catalyzed by the NS3 serine protease. Subsequent NS3-mediated cleavages of the HCV polyprotein appear to involve recognition of polyprotein cleavage junctions by an NS3 molecule of another polypeptide. In these reactions, NS3 liberates an NS3 cofactor (NS4a, found about positions 1658–1711), two proteins (NS4b found at about positions 1712–1972, and NS5a found at about positions 1973–2420), and an RNA-dependent RNA polymerase (NS5b found at about positions 2421–3011).

TABLE 1

| Domain | Approximate Boundaries* |
|---|---|
| C (core) | 1–191 |
| E1 | 192–383 |
| E2 | 384–746 |
| P7 | 747–809 |
| NS2 | 810–1026 |
| NS3 | 1027–1657 |
| NS4a | 1658–1711 |
| NS4b | 1712–1972 |
| NS5a | 1973–2420 |
| NS5b | 2421–3011 |

*Numbered relative to HCV-1. See, Choo et al. (1991) Proc. Natl. Acad. Sci. USA 88: 2451–2455.

The multiple HCV antigens are part of a single, continuous chain of amino acids, which chain does not occur in nature. Thus, the linear order of the epitopes is different than their linear order in the genome in which they occur. The linear order of the sequences of the MEFAs for use herein is preferably arranged for optimum antigenicity. Preferably, the epitopes are from more than one HCV strain, thus providing the added ability to detect multiple strains of HCV in a single assay. Thus, the MEFAs for use herein may comprise various immunogenic regions derived from the polyprotein described above. Moreover, a protein resulting from a frameshift in the core region of the polyprotein, such as described in International Publication No. WO 99/63941, may be used in the MEFAs. If desired, at least 2, 3, 4, 5, 6, 7, 8, 9, or 10 or more of one or more epitopes derived from the HCV polyprotein may occur in the fusion protein.

For example, epitopes derived from, e.g., the hypervariable region of E2, such as a region spanning amino acids 384–410 or 390–410, can be included in the MEFA antigen. A particularly effective E2 epitope is one which includes a consensus sequence derived from this region, such as the consensus sequence Gly-Ser-Ala-Ala-Arg-Thr-Thr-Ser-Gly-Phe-Val-Ser-Leu-Phe-Ala-Pro-Gly-Ala-Lys-Gln-Asn (SEC ID NO:5), which represents a consensus sequence for amino acids 390–410 of the HCV type 1 genome. A representative E2 epitope present in a MEFA of the invention can comprise a hybrid epitope spanning amino acids 390–444. Such a hybrid E2 epitope can include a consensus sequence representing amino acids 390–410 fused to the native amino acid sequence for amino acids 411–444 of HCV E2.

Additionally, the antigens may be derived from various HCV strains. Multiple viral strains of HCV are known, and epitopes derived from any of these strains can be used in a fusion protein. It is well known that any given species of organism varies from one individual organism to another and further that a given organism such as a virus can have a number of different strains. For example, as explained above, HCV includes at least 6 genotypes. Each of these genotypes includes equivalent antigenic determinants. More specifically, each strain includes a number of antigenic determinants that are present on all strains of the virus but are slightly different from one viral strain to another. For example, HCV includes the antigenic determinant known as 5-1-1 (See, FIG. 1). This particular antigenic determinant appears in three different forms on the three different viral strains of HCV. Accordingly, in a preferred embodiment of the invention all three forms of 5-1-1 appear on the multiple epitope fusion antigen used in the subject immunoassays. Similarly, equivalent antigenic determinants from the core region of different HCV strains may also be present. In general, equivalent antigenic determinants have a high degree of homology in terms of amino acid sequence which degree of homology is generally 30% or more, preferably 40% or more, when aligned. The multiple copy epitope of the present invention can also include multiple copies which are exact copies of the same epitope.

FIGS. 4 and 6A–6C show representative MEFAs for use in the present invention which are derived from HCV. However, it is to be understood that other epitopes derived from the HCV genome will also find use with the present assays.

Figure 4:
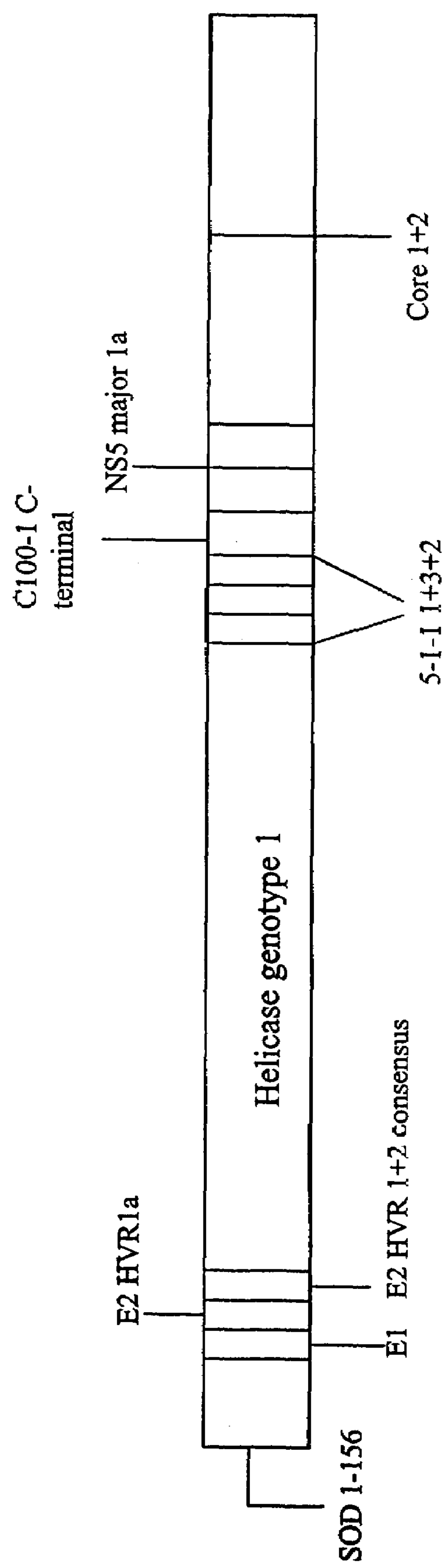
FIG. 4 is a diagrammatic representation of MEFA 7.1.

The DNA sequence and corresponding amino acid sequence of a representative multiple epitope fusion antigen, MEFA 7.1, is shown in FIGS. 5A through 5F. The general structural formula for MEFA 7.1 is shown in FIG. 4 and is as follows: hSOD-E1(type 1)-E2 HVR consensus(type 1a)-E2 HVR consensus(types 1 and 2)-helicase(type 1)-5-1-1 (type 1)-5-1-1(type 3)-5-1-1(type 2)-c100(type 1)-NS5(type 1)-NS5(type 1)-core(types 1+2)-core(types 1+2). This multiple copy epitope includes the following amino acid sequence, numbered relative to HCV-1 (the numbering of the amino acids set forth below follows the numbering designation provided in Choo, et al. (1991) *Proc. Natl. Acad. Sci. USA* 88:2451–2455, in which amino acid #1 is the first methionine encoded by the coding sequence of the core region): amino acids 1–156 of superoxide dismutase (SOD, used to enhance recombinant expression of the protein); amino acids 303 to 320 of the polyprotein from the E1 region; amino acids 390 to 410 of the polyprotein, representing a consensus sequence for the hypervariable region of HCV-1a E2; amino acids 384 to 414 of the polyprotein from region E2, representing a consensus sequence for the E2 hypervariable regions of HCV-1 and HCV-2; amino acids 1193–1658 of the HCV-1 polyprotein which define the helicase; three copies of an epitope from 5-1-1, amino acids 1689–1735, one from HCV-1, one from HCV-3 and one from HCV-2, which copies are equivalent antigenic determinants from the three different viral strains of HCV; HCV polypeptide C100 of HCV-1, amino acids 1901–1936 of the polyprotein; two exact copies of an epitope from the NS5 region of HCV-1, each with amino acids 2278 to 2313 of the HCV polyprotein; and two copies of an epitope from the core region, one from HCV-1 and one from HCV-2, which copies are equivalent antigenic determinants represented by amino acids 9 to 32, 39–42 and 64–88 of HCV-1 and 67–84 of HCV-2.

Table 2 shows the amino acid positions of the various epitopes with reference to FIGS. 5A through 5F herein.

TABLE 2

MEFA 7.1

| mefa aa# | 5' end site | epitope | hcv aa# | strain |
|---|---|---|---|---|
| 1–156 | Nco1 | hSOD | | |
| 159–176 | EcoR1 | E1 | 303–320 | 1 |
| 179–199 | Hind111 | E2 HVR1a consensus | 390–410 | 1 |
| 200–230 | | E2 HLVR1 + 2 consensus | 384–414 | 1 + 2 |
| 231–696 | Sal1 | Helicase | 1193–1658 | 1 |
| 699–745 | Sph1 | 5-1-1 | 1689–1735 | 1 |
| 748–794 | Nru1 | 5-1-1 | 1689–1735 | 3 |
| 797–843 | Cla1 | 5-1-1 | 1689–1735 | 2 |
| 846–881 | Ava1 | C100 | 1901–1936 | 1 |
| 884–919 | Xba1 | NS5 | 2278–2313 | 1 |
| 922–957 | Bgl11 | NS5 | 2278–2313 | 1 |
| 958–1028 | Nco1 | core epitopes | 9–32, 39–42 | 1 |
| | | | 64–88 | 1 |
| | | | 67–84 | 2 |
| 1029–1099 | Bal1 | core epitopes | 9–32, 39–42, | 1 |
| | | | 64–88 | 1 |
| | | | 67–84 | 2 |

Figure 2:
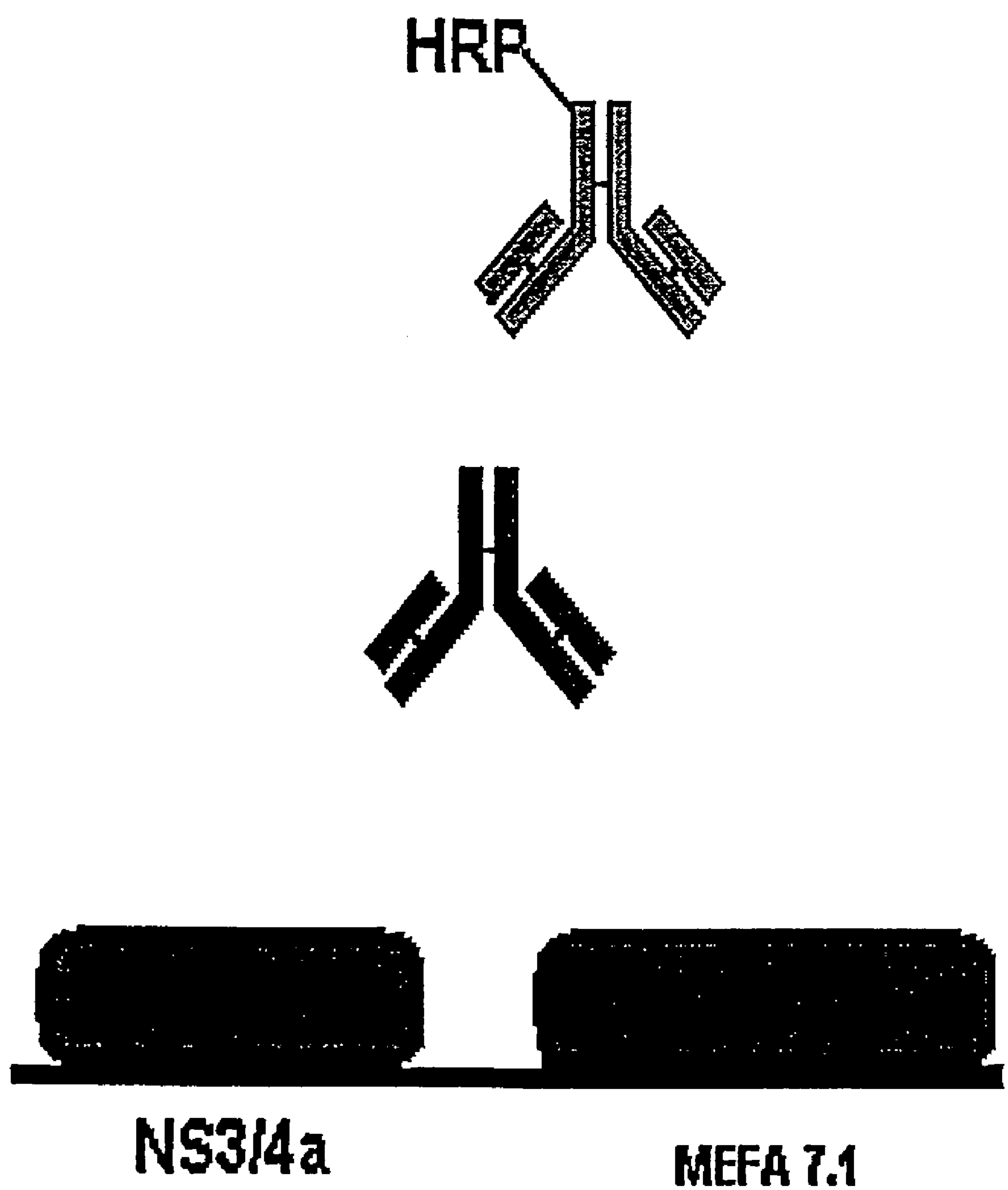
FIG. 2 is a schematic drawing of a representative immunoassay under the invention.

In one embodiment of the invention, depicted in FIG. 2, a rapid capture ligand immunoassay is performed using a conformational epitope from NS3/4a and one or more multiple epitope fusion antigens, such as MEFA 7.1. The sample is combined with the antigens, which may be present on a solid support, as described further below. If the sample is infected with HCV, HCV antibodies to those epitopes present on the solid support will bind to the solid support components. Detection is by the attachment of a detectable marker (such as horse radish peroxidase (HRP) as shown in FIG. 2) to a member of the antigen/antibody complex. Attachment may be by covalent means or by subsequent binding of detectably labeled antibodies, such as in a standard sandwich assay, or by enzyme reaction, the product of which reaction is detectable. The detectable marker may include, but is not limited to, a chromophore, an antibody, an antigen, an enzyme, an enzyme reactive compound whose cleavage product is detectable, rhodamine or rhodamine derivative, biotin, avidin, strepavidin, a fluorescent compound, a chemiluminescent compound, such as dimethyl acridinium ester (DMAE, Ciba Corning Diagnostics Corp.), derivatives and/or combinations of these markers. A detectably labeled anti-human antibody, capable of detecting a human IgG molecule present, can be conveniently used.

In order to further an understanding of the invention, a more detailed discussion is provided below regarding production of polypeptides for use in the immunoassays and methods of conducting the immunoassays.

Production of Antigens for use in the HCV Immunoassays

As explained above, the molecules of the present invention are generally produced recombinantly. Thus, polynucleotides encoding HCV antigens for use with the present invention can be made using standard techniques of molecular biology. For example, polynucleotide sequences coding for the above-described molecules can be obtained using recombinant methods, such as by screening cDNA and genomic libraries from cells expressing the gene, or by deriving the gene from a vector known to include the same. Furthermore, the desired gene can be isolated directly from viral nucleic acid molecules, using techniques described in the art, such as in Houghton et al., U.S. Pat. No. 5,350,671. The gene of interest can also be produced synthetically, rather than cloned. The molecules can be designed with appropriate codons for the particular sequence. The complete sequence is then assembled from overlapping oligonucleotides prepared by standard methods and assembled into a complete coding sequence. See, e.g., Edge (1981) *Nature* 292:756; Nambair et al. (1984) *Science* 223:1299; and Jay et al. (1984) *J. Biol. Chem.* 259:6311.

Thus, particular nucleotide sequences can be obtained from vectors harboring the desired sequences or synthesized completely or in part using various oligonucleotide synthesis techniques known in the art, such as site-directed mutagenesis and polymerase chain reaction (PCR) techniques where appropriate. See, e.g., Sambrook, supra. In particular, one method of obtaining nucleotide sequences encoding the desired sequences is by annealing complementary sets of overlapping synthetic oligonucleotides produced in a conventional, automated polynucleotide synthesizer, followed by ligation with an appropriate DNA ligase and amplification of the ligated nucleotide sequence. via PVR. See, e.g., Jayaraman et al. (1991) *Proc. Natl. Acad. Sci. USA* 88:4084–4088. Additionally, oligonucleotide directed synthesis (Jones et al. (1986) *Nature* 54:75–82), oligonucleotide directed mutagenesis of pre-existing nucleotide regions (Riechmann et al. (1988) *Nature* 332:323–327 and Verhoeyen et al. (1988) *Science* 239:1534–1536), and enzymatic filling-in of gapped oligonucleotides using $T_4$ DNA polymerase (Queen et al. (1989) *Proc. Natl. Acad. Sci. USA* 86:10029–10033) can be used under the invention to provide molecules having altered or enhanced antigen-binding capabilities, and/or reduced immunogenicity.

Once coding sequences have been prepared or isolated, such sequences can be cloned into any suitable vector or replicon. Numerous cloning vectors are known to those of skill in the art, and the selection of an appropriate cloning vector is a matter of choice. Suitable vectors include, but are not limited to, plasmids, phages, transposons, cosmids, chromosomes or viruses which are capable of replication when associated with the proper control elements.

The coding sequence is then placed under the control of suitable control elements, depending on the system to be used for expression. Thus, the coding sequence can be placed under the control of a promoter, ribosome binding site (for bacterial expression) and, optionally, an operator, so that the DNA sequence of interest is transcribed into RNA by a suitable transformant. The coding sequence may or may not contain a signal peptide or leader sequence which can later be removed by the host in post-translational processing. See, e.g., U.S. Pat. Nos. 4,431,739; 4,425,437; 4,338,397.

In addition to control sequences, it may be desirable to add regulatory sequences which allow for regulation of the expression of the sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector. For example, enhancer elements may be used herein to increase expression levels of the constructs. Examples include the SV40 early gene enhancer (Dijkema et al. (1985) *EMBO J.* 4:761), the enhancer/promoter derived from the long terminal repeat (LTR) of the Rous Sarcoma Virus (Gorman et al. (1982) *Proc. Natl. Acad. Sci. USA* 79:6777) and elements derived from human CMV (Boshart et al. (1985) *Cell* 41:521), such as elements included in the CMV intron A sequence (U.S. Pat. No. 5,688,688). The expression cassette may further include an origin of replication for autonomous replication in a suitable host cell, one or more selectable markers, one or more restriction sites, a potential for high copy number and a strong promoter.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the molecule of interest may be desirable to achieve this end. For example, in some cases it may be necessary to modify the sequence so that it can be attached to the control sequences in the appropriate orientation; i.e., to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site.

As explained above, it may also be desirable to produce mutants or analogs of the antigen of interest. This is particularly true with NS3/4a. Methods for doing so are described in, e.g., Dasmahapatra et al., U.S. Pat. No. 5,843,752 and Zhang et al., U.S. Pat. No. 5,990,276. Mutants or analogs of this and other HCV proteins for use in the subject assays may be prepared by the deletion of a portion of the sequence encoding the polypeptide of interest, by insertion of a sequence, and/or by substitution of one or more nucleotides within the sequence. Techniques for modifying nucleotide sequences, such as site-directed mutagenesis, and the like, are well known to those skilled in the art. See, e.g., Sambrook et al., supra; Kunkel, T. A. (1985) *Proc. Natl. Acad. Sci. USA* (1985) 82:448; Geisselsoder et al. (1987) *BioTechniques* 5:786; Zoller and Smith (1983) *Methods Enzymol.* 100:468; Dalbie-McFarland et al. (1982) *Proc. Natl. Acad. Sci USA* 79:6409.

The molecules can be expressed in a wide variety of systems, including insect, mammalian, bacterial, viral and yeast expression systems, all well known in the art.

For example, insect cell expression systems, such as baculovirus systems, are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit). Similarly, bacterial and mammalian cell expression systems are well known in the art and described in, e.g., Sambrook et al., supra. Yeast expression systems are also known in the art and described in, e.g., *Yeast Genetic Engineering* (Barr et al., eds., 1989) Butterworths, London.

A number of appropriate host cells for use with the above systems are also known. For example, mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human embryonic kidney cells, human hepatocellular carcinoma cells (e.g., Hep G2), Madin-Darby bovine kidney ("MDBK") cells, as well as others. Similarly, bacterial hosts such as *E. coli, Bacillus subtili*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni.*

Nucleic acid molecules comprising nucleotide sequences of interest can be stably integrated into a host cell genome or maintained on a stable episomal element in a suitable host cell using various gene delivery techniques well known in the art. See, e.g., U.S. Pat. No. 5,399,346.

Depending on the expression system and host selected, the molecules are produced by growing host cells transformed by an expression vector described above under conditions whereby the protein is expressed. The expressed protein is then isolated from the host cells and purified. If the expression system secretes the protein into growth media, the product can be purified directly from the media. If it is not secreted, it can be isolated from cell lysates. The selection of the appropriate growth conditions and recovery methods are within the skill of the art.

The production of various HCV antigens, including antigens used in the multiple epitope fusion proteins described above, has been described. See, e.g., Houghton et al., U.S. Pat. Nos. 5,350,671 and 5,683,864; Chien et al., *J. Gastroent. Hepatol.* (1993) 8:S33–39; Chien et al., International Publication No. WO 93/00365; Chien, D. Y., International Publication No. WO 94/01778; Chien et al., *Proc. Natl. Acad. Sci. USA* (1992) 89:10011–10015; Chien, D. Y., International Publication No. WO 94/01778; and commonly owned, allowed U.S. patent application Ser. Nos. 08/403,590 and 08/444,818, the disclosures of which are incorporated herein by reference in their entireties.

Immunodiagnostic Assays

Once produced, the HCV antigens may be used in virtually any assay format that employs a known antigen to detect antibodies. A common feature of all of these assays is that the antigen is contacted with the body component suspected of containing HCV antibodies under conditions that permit the antigen to bind to any such antibodies present in the component. Such conditions will typically be physiologic temperature, pH and ionic strength using an excess of antigen. The incubation of the antigen with the specimen is followed by detection of immune complexes comprised of the antigen.

Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules, as discussed in detail above. Assays which amplify the signals from the immune complex are also known; examples of which are assays which utilize biotin and avidin, and enzyme-labeled and mediated immunoassays, such as ELISA assays.

The immunoassay may be, without limitation, a heterogenous or a homogeneous format, and of a standard or competitive type. In a heterogeneous format, the polypeptide is typically bound to a solid matrix or support to facilitate separation of the sample from the polypeptide after incubation. A solid support, for the purposes of this invention, can be any material that is an insoluble matrix and can have a rigid or semi-rigid surface. Exemplary solid supports include, but are not limited to, substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like. Particular supports include plates, pellets, disks, capillaries, hollow fibers, needles, pins, solid fibers, cellulose beads, pore-glass beads, silica gels, polystyrene beads optionally cross-linked with divinylbenzene, grafted co-poly beads, polyacrylamide beads, latex beads, dimethylacrylamide beads optionally crosslinked with N-N'-bis-acryloylethylenediamine, and glass particles coated with a hydrophobic polymer.

If desired, the molecules to be added to the solid support can readily be functionalized to create styrene or acrylate moieties, thus enabling the incorporation of the molecules into polystyrene, polyacrylate or other polymers such as polyimide, polyacrylamide, polyethylene, polyvinyl, polydiacetylene, polyphenylene-vinylene, polypeptide, polysaccharide, polysulfone, polypyrrole, polyimidazole, polythiophene, polyether, epoxies, silica glass, silica gel, siloxane, polyphosphate, hydrogel, agarose, cellulose, and the like.

In one context, a solid support is first reacted with the HCV antigens (collectively called "the solid-phase components" herein), under suitable binding conditions such that the molecules are sufficiently immobilized to the support. Sometimes, immobilization to the support can be enhanced by first coupling the antigen and/or antibody to a protein with better solid phase-binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other reagents that can be used to bind molecules to the support include polysaccharides, polylactic acids, polyglycolic acids, polymeric amino acids, amino acid copolymers, and the like. Such molecules and methods of coupling these molecules to antigens, are well known to those of ordinary skill in the art. See, e.g., Brinkley, M. A. (1992) *Bioconjugate Chem.* 3:2–13; Hashida et al. (1984) *J. Appl. Biochem.* 6:56–63; and Anjaneyulu and Staros (1987) *International J. of Peptide and Protein Res.* 30:117–124.

After reacting the solid support with the solid-phase components, any nonimmobilized solid-phase components are removed from the support by washing, and the support-bound components are then contacted with a biological sample suspected of containing HCV antibodies (collectively called "ligand molecules" herein) under suitable binding conditions. If HCV antibodies are present in the sample, they will form a complex with the HCV antigens. After washing to remove any nonbound ligand molecules, detectably labeled anti-xenogenic (e.g., anti-human) antibodies, which recognize an epitope on anti-HCV antibodies, is added. These antibodies bind due to complex formation.

In a homogeneous format, the test sample is incubated with the combination of antigens in solution. For example, it may be under conditions that will precipitate any antigen-antibody complexes which are formed. Both standard and competitive formats for homogeneous assays are also known in the art.

In a standard format, the amount of HCV antibodies forming the antibody-antigen complex is directly monitored. This may be accomplished by determining whether labeled anti-xenogenic (e.g., anti-human) antibodies which recognize an epitope on anti-HCV antibodies will bind due to complex formation. In a competitive format, the amount of HCV antibodies in the sample is deduced by monitoring the competitive effect on the binding of a known amount of labeled antibody (or other competing ligand) in the complex.

More particularly, complexes formed comprising anti-HCV antibody (or, in the case of competitive assays, the amount of competing antibody) are detected by any of a number of known techniques, depending on the format. For example, unlabeled HCV antibodies in the complex may be detected using a conjugate of antixenogeneic Ig complexed with a label, (e.g., an enzyme label). In an immunoprecipitation or agglutination assay format, the reaction between the HCV antigens and the antibody forms a network that precipitates from the solution or suspension and forms a visible layer or film of precipitate. If no anti-HCV antibody is present in the test specimen, no visible precipitate is formed.

The above-described assay reagents, including the immunoassay solid support with bound antibodies and antigens, as well as antibodies and antigens to be reacted with the captured sample, can be provided in kits, with suitable instructions and other necessary reagents, in order to conduct immunoassays as described above. The kit will normally contain in separate containers the combination of antigens (either already bound to a solid matrix or separate with reagents for binding them to the matrix), control antibody formulations (positive and/or negative), labeled antibody when the assay format requires same and signal generating reagents (e.g., enzyme substrate) if the label does not generate a signal directly. Instructions (e.g., written, tape, VCR, CD-ROM, etc.) for carrying out the assay usually will be included in the kit. The kit can also contain, depending on the particular immunoassay used, other packaged reagents and materials (i.e. wash buffers and the like). Standard immunoassays, such as those described above, can be conducted using these kits.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Construction of MEFA 7 and MEFA 7.1

The following example illustrates the preparation of a polyprotein cassette of multiple HCV epitopes. The polyprotein expressed from the multiple epitope cassette is referred to herein as a Multiple Epitope Fusion Antigen (MEFA). Preferably, where an epitope is repeated, the extra copy or copies are tandemly arrayed in the same orientation. It is understood that the region of a viral coding sequence used as an epitope may be varied slightly and still retain antigenic activity, and that the amino acid numbering designation may vary from strain to strain. Thus, the repeated epitopes may vary one from another in amino acid sequence due to strain sequence variations and/or numbering designation. Preferably, the amino acid sequences of repeated epitopes within a MEFA are at least 30% homologous at the amino acid level, more preferably at least 40% homologous at the amino acid level.

Unique restriction enzyme sites were introduced in order to connect the epitopes in the prescribed order and enhance the usefulness of the invention by facilitating modifications in design of a chimeric antigen. The choice of restriction enzyme sites and cloning procedures are readily determined by one of ordinary skill in the art of recombinant DNA technology. Preferably, the epitope junctions (amino acid sequences created between epitopes due to cloning) do not generate non-specific epitopes. Non-specific epitopes are, for example, non-HCV sequences which do not exist adjacent to the HCV epitopes in nature. Non-specific epitopes may bind antibodies in a test sample causing false positive assay results. Preferably, the multiple epitope fusion protein is tested for false positive results due to such sequences generated at the epitope junctions. To avoid non-specific interactions with the MEFA due to junction sequences, the DNA sequence encoding the junction may, for example, be mutated such that non-specific interactions with the mutant amino acid sequence are reduced, and cloning of the epitope fragments is possible.

The HCV MEFA 7 and 7.1 expression cassettes were constructed by cloning the coding nucleotide sequences containing major epitopes in a tandem array as shown in FIG. 4. A major epitope was chosen based on antibody reaction frequency and reaction intensity (titer) to the epitope (Chein, D. Y. et al. (1994) Viral Hepatitis and Liver Disease, pp. 320–324). The various DNA segments coding for the HCV epitopes were constructed by PCR amplification or by synthetic oligonucleotides. The amino acids in each segment are set forth in Table 2 above and shown in FIGS. 5A–5F. The complete HCV-1 amino acid sequence (3011 amino acids) was determined by Choo, et al. (1991) *Proc. Natl. Acad. Sci. USA* 88:2451–2455, herein incorporated by reference in its entirety. Oligonucleotides capable of binding to HCV are described in U.S. Pat. No. 5,350,671, herein incorporated by reference in its entirety. The numbering of the amino acids in epitopes of the invention follows the numbering designation provided in Choo, et al., supra, in which amino acid number 1 is the first methionine encoded by the coding sequence of the core region, unless otherwise specified. For example, one epitope segment from NS5 is represented by amino acids 2278 to 2313 of the HCV polyprotein. An epitope from the E1 region is represented by amino acids 303 to 320, numbered relative to the HCV-1 polyprotein.

MEFA 7 and 7.1 each contain epitopes from HCV-1, HCV-2 and HCV-3, allowing for detection of multiple types of a virus in a single assay. Methods of determining HCV serotype are found in WO 96/27153, herein incorporated by reference in its entirety. For example, epitopes from the 5-1-1 region have been found to vary between serotypes of HCV. A copy of each of the HCV type-specific 5-1-1 epitopes present in the MEFAs described herein allows binding of any of the HCV types that may be present in the test biological sample.

The MEFA 7 and 7.1 constructs were genetically engineered for expression in Saccharomyces cerevisiae, utilizing the yeast expression vector pBS24.1 which contains 2μ sequences for autonomous replication in yeast and the yeast genes leu2-d and URA3 as selectable markers. The β-lactamase gene and the ColE1 origin of replication, required for plasmid replication in bacteria, were also present in this expression vector. The yeast expression vector for MEFA 7, ps.MEFA7, was constructed first. Subsequently, the plasmid was modified in the coding region for the HCV core epitopes to create the plasmid ps.MEFA7.1, encoding the MEFA 7.1 antigen.

In particular, as shown in FIGS. 7A through 7D, a yeast expression plasmid for MEFA 7 was constructed as follows. First, a BamHI/HindIII fragment of 1896 bp, encoding the ADH2/GAPDH hybrid promoter, hSOD (amino acids 1–156), followed by an E1 epitope (amino acids 303–320, HCV1 strain), was isolated from ps.MEFA6, the expression plasmid encoding MEFA 6, described in International Publication No. WO. 97/44469. Next, a HindIII/SphI synthetic DNA fragment of 269 bp which contains the coding sequence for E2 HVR1a consensus epitope (amino acids 390–410, HCV-1), E2 HVR1+2 consensus epitope (amino acids 384–414, HCV1+2) and the 5' end of the helicase domain (amino acids 1193–1229, HCV-1) was created. An SphI/EclXI fragment of 1264 bp, encoding the remainder of the helicase domain (amino acids 1230–1651, HCV-1), was gel-purified from pTac5/HelI plasmid DNA. The HindIII/SphI synthetic DNA fragment and the SphI/EclXI 1264 bp fragment were ligated into vector pSP72new.HindIII/EclXI vector, to produce pSP72new.HindIII/EclXI/e2.helicase. This vector was derived from pSP72 an *E. coli* vector commercially available from Promega, Madison, Wis. (see, GenBank/EMBL Accession Number X65332). In particular, to facilitate the subcloning of several MEFA 7 epitopes, a new multiple cloning site (MCS) polylinker was introduced, via synthetic oligos, between the SphI and BglII sites of pSP72. This new plasmid, named pSP72new, was digested with HindIII and EclXI (also known as EagI), which have unique sites in the MCS. It was then dephosphorylated and gel-purified.

*E. coli* HB101 competent cells were transformed with the plasmid, and plated on Luria agar plates containing 100 μg/ml ampicillin. Desired clones were identified using mini-prep DNA analysis. After sequence verification, the plasmid pSP72new.HindIII/EclXI/e2.helicase subclone #4 was digested with HindIII and EclXI(EagI) to generate a 1534 bp fragment. The HindIII/EclX1 fragment was gel-purified and ligated with EclXI/SphI oligonucleotides, encoding the last amino acids of the helicase domain (amino acids 1651–1658, HCV-1), into a pGEM7 HindIII/SphI vector. HB101 competent cells were transformed and plated on Luria-ampicillin (100 μg/ml). After identification of the desired clones and sequence confirmation, pGEM7HindIII/SphI subclone #9 was digested with HindIII and SphI to generate a 1560 bp fragment, which was gel purified (see, FIG. 7A).

To assemble the 3' end portion of MEFA 7, the following steps were performed. The 5-1-1 epitopes (amino acids 1689–1735) from HCV-1, HCV-3 and HCV-2 (in this order) were gel-isolated from ps.MEFA6, the expression plasmid encoding MEFA 6, described in International Publication No. WO 97/44469, as an SphI/AvaI fragment of 441 bp. This fragment was ligated with synthetic AvaI/XbaI oligonucleotides encoding the c100 epitope (amino acids 1901–1936) into a pSP72new.SphI/XbaI vector. After HB101 transformation, clone identification, and sequence verification, pSP72newSXi subclone #6 was digested with XbaI and NotI to prepare a pSP72newXbaI/NotI vector. Additionally, an XbaI/NcoI fragment of 221 bp, which encoded a double repeat of an NS5 epitope (amino acids 2278–2313, HCV-1), was isolated from ps.MEFA6. The Xba/NcoI fragment was ligated with NcoI/NotI oligonucleotides, encoding the first amino acids of the HCV-1 core epitope, amino acids 9–17, in which the Lys at position 9 was changed to Arg, and the Asn at position 11 was changed to Thr, into the pSP72newXbaI/NotI vector prepared above. HB101 transformants were analyzed and their plasmid DNA sequenced. A subclone, termed pSP72newSX/XNi #3, was digested with NotI/SalI to prepare a vector for subsequent subdloning (see, FIG. 7B).

To complete the assembly of the 3' end of MEFA 7, a double repeat of the sequence encoding a core epitope with amino acids 9–53 from HCV-1, plus two genotype-specific epitopes of the core region (amino acids 64–88, HCV-1 and amino acids 67–84, HCV-2) were subclone as follows into NotI-SalI digested pSP72newSX/XNi subclone #3. First, a NotI/XmnI fragment of 92 bp encoding amino acids 18–51 of a core epitope was isolated from pd.Core191RT clone #20. Plasmid pd.Core191RT was constructed by ligating into the pBS24.1 BamHI-SalI yeast expression vector, a 1365 bp BamHI-NcoI fragment for the ADH2/GAPDH promoter, and a 615 bp NcoI-SalI fragment encoding the first 191 amino acids of HCV-1 core with amino acid 9 mutated from Lys to Arg and amino acid 11 mutated from Asn to Thr. The 615 bp NcoI-SalI fragment was derived from an *E. coli* expression vector in which the core sequence for amino acids 1–191, with the same two mutations described above, had been cloned.

The 92 bp NotI/XmnI fragment was ligated with a pSP72newNot/Kpn vector and with XmnI/KpnI oligonucleotides which encode the 3' end of the complete core epitope. After sequence verification of the positive clones, pSP72newNKi subclone #4 was digested with NotI and KpnI, and a 224 bp fragment was gel-isolated. This NotI/KpnI fragment was ligated with 284 bp of oligonucleotides (KpnI-SalI ends) encoding a complete repeat of the core epitope described above into the pSP72newSX/XNi NotI/SalI vector described above. After HB101 transformation, clone identification and sequence verification, pSP72newSX/XN/NSi subclone #18 was digested with SphI and SalI and a fragment of 1317 bp was gel-isolated (see, FIG. 7C).

Figure 7A:
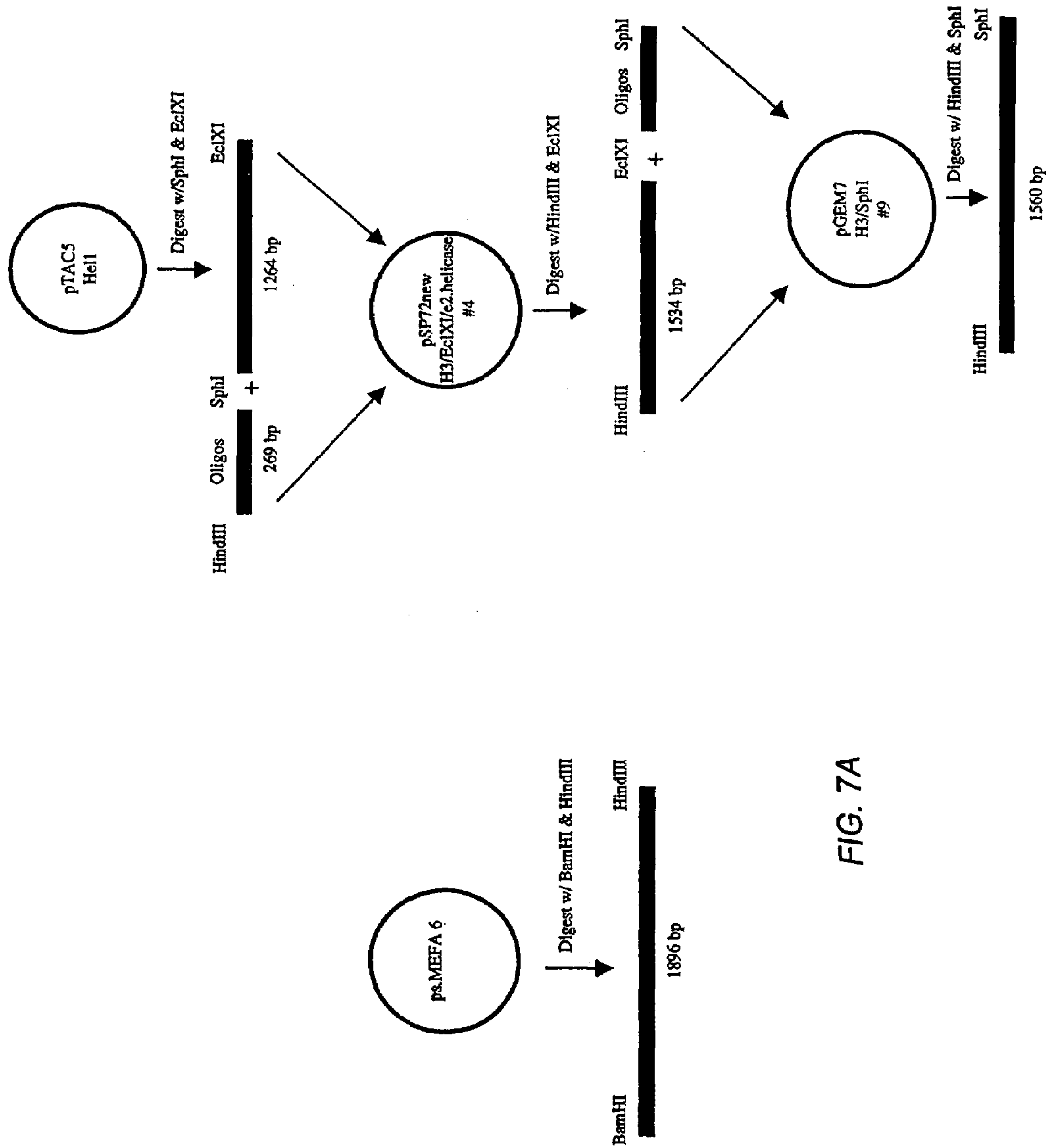
FIGS. 7A–7D are diagrams of the construction of psMEFA7.
Figure 7B:
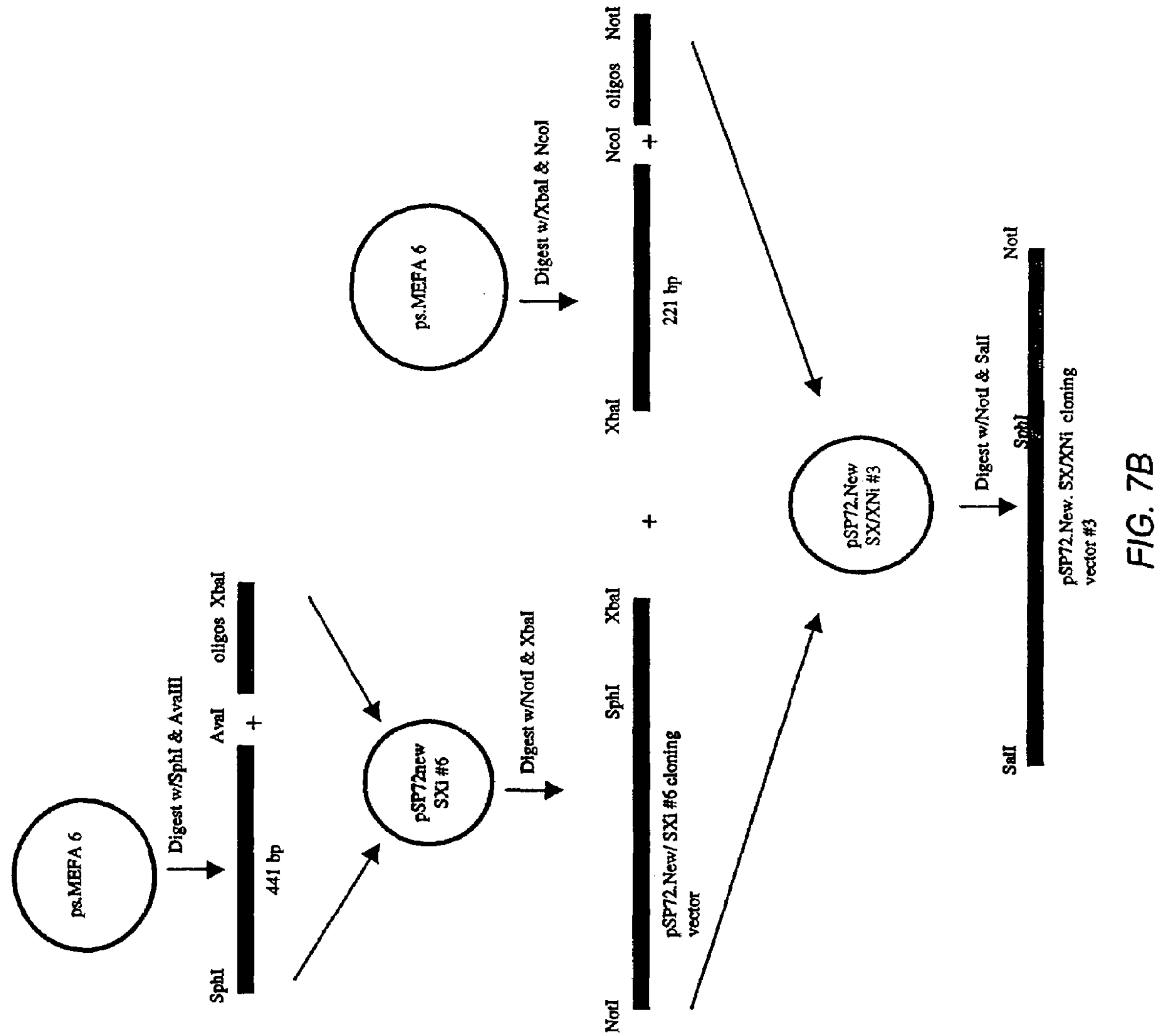
Figure 7C:
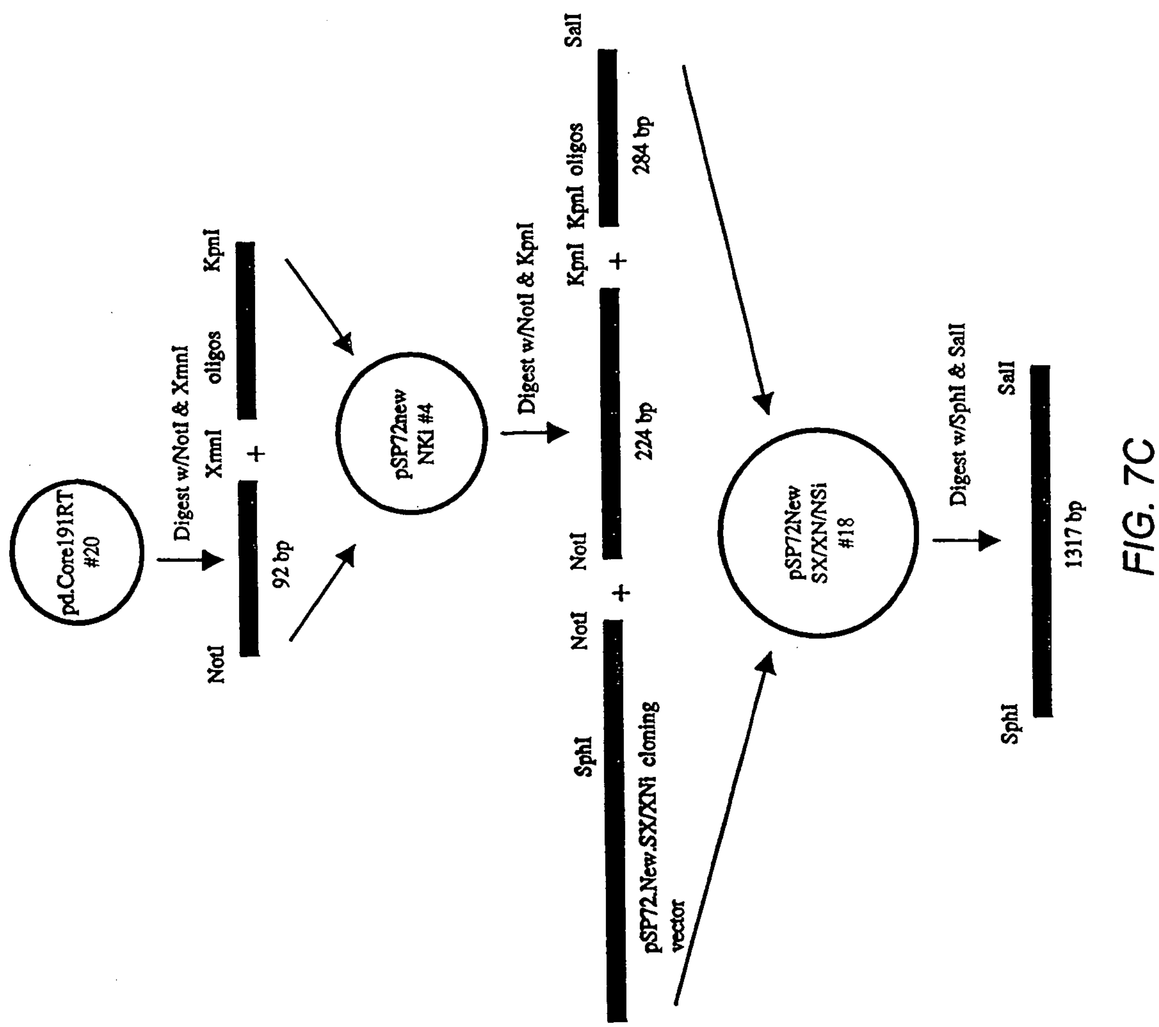
Figure 7D:
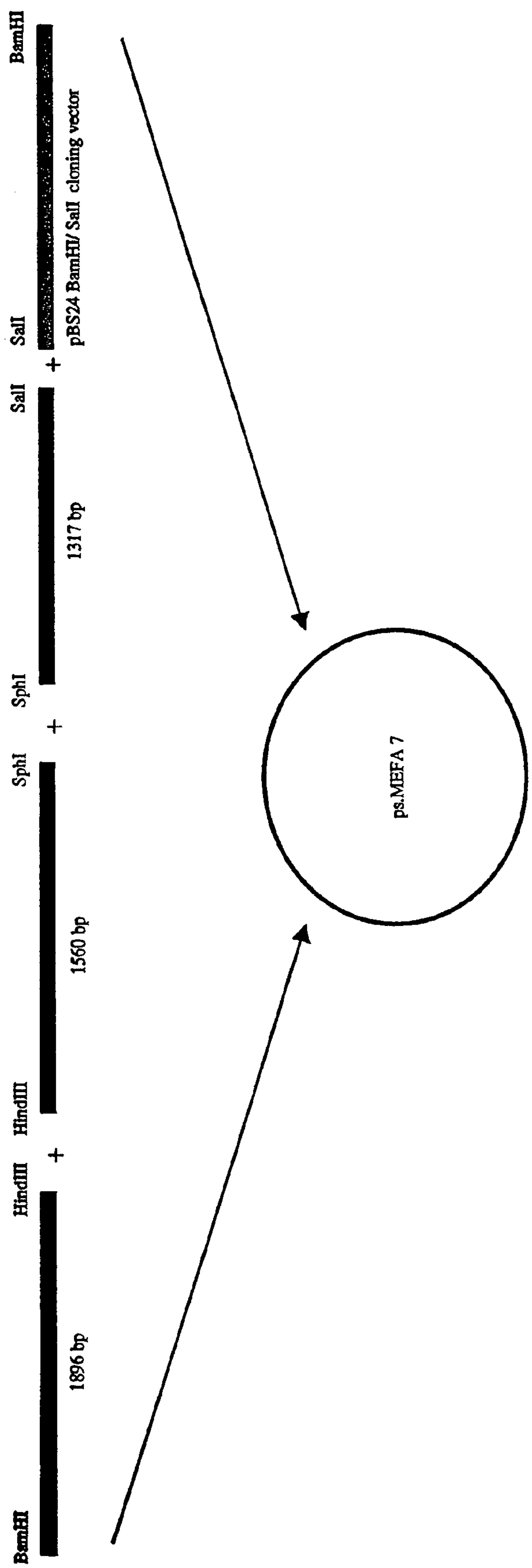

Lastly, the following fragments, described above, were ligated into the pBS24.1 BamHI/SalI yeast expression vector to create ps.MEFA7 (see, FIG. 7D):

the BamHI/HindIII fragment of 1896 bp (FIG. 7A)
the HindIII/SphI fragment of 1560 bp (FIG. 7A)
the SphI/SalI fragment of 1317 bp (FIG. 7C)

*S. cerevisiae* strain AD3 was transformed with ps.MEFA7 and single transformants were checked for expression after depletion of glucose in the medium. The recombinant protein was expressed at high levels in yeast, as detected by Coomassie blue staining. In particular, yeast cells were transformed with the MEFA expression plasmid using a lithium acetate protocol. Ura transformants were streaked for single colonies and patched onto Leu/8% glucose plates to increase plasmid copy number. Leu starter cultures were grown for 24 hours at 30° C. and then diluted 1:20 in YEPD (yeast extract bactopeptone 2% glucose) media. The cells were grown for 48 hours at 30° C. and harvested. To test for expression of the MEFA 7 recombinant antigen, an aliquot of the cells was lysed with glass beads in lysis buffer (10 mM Tris-Cl pH 7.5, 1 mM EDTA, 10 mM DTT). The lysate was centrifuged at high speed. The supernatant and insoluble pellet were analyzed on SDS protein gels. MEFA 7 was highly enriched in the insoluble pellet fraction.

The MEFA 7 antigen was purified as follows. *S. cerevisiae* cells expressing MEFA 7 were harvested as described above. The cells were suspended in lysis buffer (50 mM Tris, 0.15 M NaCl, 1 mM EDTA, 1 mM PMSF, pH 8.0) and lysed in a Dyno-Mill (Wab Willy A. Bachofon, Basel, Switzerland) or equivalent apparatus using glass beads. The lysate was centrifuged at low speed conditions (3,000 to 5,000 rpm, 15 min) and the pellet containing the insoluble protein fraction was washed with increasing concentrations of urea (1 M, 2 M, 3 M) in lysis buffer. Protein was solubilized from the centrifugation pellet with 0.1 N NaOH, 4 M urea in lysis buffer. Cell debris was removed by low speed centrifugation at 3,000 to 5,000 rpm, 15 min. The supernatant was adjusted to pH 8.0 with 6 N HCl to precipitate proteins insoluble under these conditions.

The precipitate was removed by centrifugation and the supernatant was adjusted to 2.3% SDS, 50 mM DTT, pH 8.0 and boiled for 3 min. Proteins in the mixture were fractionated by gel filtration on a Pharmacia Sephacryl S-400 in phosphate buffered saline containing 0.1% SDS, 1 mM EDTA and adjusted to pH 7.4. Column eluate fractions containing MEFA 7 were collected, pooled, and concentrated on an Amicon YM-30 membrane. Gel filtration was repeated on the pooled fractions using the same column and conditions.

During the analysis of MEFA 7 in a trial assay, it was discovered that a monoclonal antibody used as a detection conjugate reacted with a specific sequence of the core epitope (amino acids 33–38). Thus, ps.MEFA7.1 was designed to eliminate amino acids 33–38 from the core epitope region.

A yeast expression vector for MEFA 7.1 was made as follows. First, the double repeat of the core epitope at the 3' end of ps.MEFA7 was modified. To do so, an NcoI/KpnI synthetic fragment of 206 bp, encoding the first core epitope repeat (amino acids 9–32, 39–42 and 64–88 of HCV-1, and amino acids 67–82 of HCV-2), and a KpnI/SalI synthetic fragment of 233 bp encoding amino acids 83 and 84 of HCV-2, followed by the second core epitope repeat (amino acids 9–32, amino acids 39–42 and amino acids 64–88, HCV-1, amino acids 67–84, HCV-2) were subclone respectively into a pSP72new.NcoI/KpnI vector and a pSP72new.KpnI/SalI vector. After HB101 transformation, clone identification and sequence conformation, pSP72newNKi clone #21 was digested with NcoI and KpnI to isolate the NcoI/KpnI fragment of 206 bp and pSP72newKSi clone #32 was digested with KpnI and SalI to isolate the KpnI/SalI fragment of 233 bp.

Figure 8:
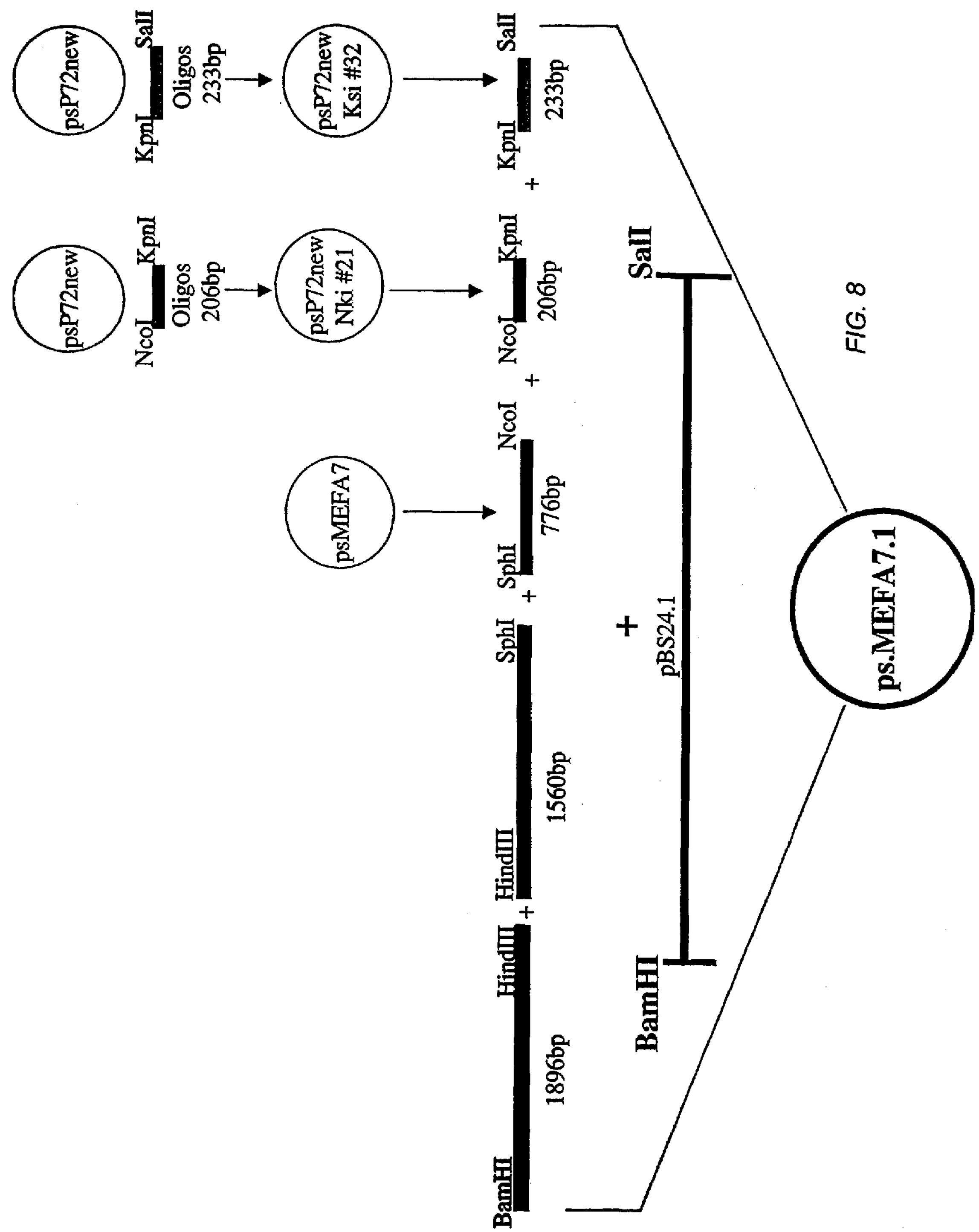
FIG. 8 is a diagram of the construction of psMEFA7.1.

Plasmid ps.MEFA7.1 was assembled by ligating the following fragments into the pBS24.1 BamHI/SalI yeast expression vector (see, FIG. 8):

the BamHI/HindIII fragment of 1896 bp, described above for ps.MEFA7;

the HindIII/SphI fragment of 1560 bp described above for ps.MEFA7;

an SphI/NcoI fragment of 776 bp isolated from ps.MEFA7 encoding the 5-1-1 epitopes, c100 epitope and NS5 epitope;

the NcoI/KpnI fragment of 206 bp;

and KpnI/SalI fragment of 233 bp.

*S. cerevisiae* strain AD3 was transformed with ps.MEFA7.1 and single transformants were checked for expression after depletion of glucose in the medium, as described above. The recombinant protein was expressed at high levels in yeast, as detected by Coomassie blue staining.

The MEFA 7.1 antigen was purified as follows. *S. cerevisiae* cells expressing MEFA 7.1 were harvested as described above. The cells were suspended in lysis buffer (50 mM Tris, 0.15 M NaCl, 1 mM EDTA, pH 8.0) and lysed in a Dyno-Mill (Wab Willy A. Bachofen, Basel, Switzerland) or equivalent apparatus using glass beads. The lysate was centrifuged at 10,000 rpm, 30 min in a JA-10 rotor, and the pellet containing the insoluble protein fraction was washed with increasing concentrations of Urea (1 M, 2 M, 3 M) in lysis buffer. Protein was solubilized from the centrifugation pellet with 0.1 N NaOH, 4 M Urea, 50 mM DTT in lysis buffer. Cell debris was removed by centrifugation at 14,000 rpm, 20 min in a JA-14 rotor. The supernatant was adjusted to pH 8.0 with 6 N HCl to precipitate proteins insoluble under these conditions.

The precipitate was removed by centrifugation at 14,000 rpm, 20 min in a JA-14 rotor. The supernatant was adjusted to 2.3% SDS and heated to 70–75° C. in boiling water then cooled to room temperature. Proteins in the mixture were fractionated by gel filtration on a Pharmacia Sephacryl S-400 HR in PBS containing 0.1% SDS, 1 mM EDTA and adjusted to pH 7.4. Column eluate fractions containing MEFA 7.1 were collected, pooled, and concentrated on an Amicon YM-30 membrane. Pooled gel filtration fractions were adjusted to 2.3% SDS, 50 mM DTT, and heated/cooled as above. This pool was subjected to a second gel filtration step on a Pharmacia Sephacryl S-300 HR column under the same conditions as the first gel filtration step.

EXAMPLE 2

Recombinant Production of an NS3/4a Conformational Epitope

A conformational epitope of NS3/4a was obtained as follows. This epitope has the sequence specified in FIGS. 3A through 3D and differs from the native sequence at positions 403 (amino acid 1428 of the HCV-1 full-length sequence) and 404 (amino acid 1429 of the HCV-1 full-length sequence). Specifically, the Thr normally occurring at position 1428 of the native sequence has been mutated to Pro and Ser which occurs at position 1429 of the native sequence has been mutated to Ile.

In particular, the yeast expression vector used was pBS24.1, described above. Plasmid pd.hcv1a.ns3ns4aPI, which encoded a representative NS3/4a epitope used in the subject immunoassays, was produced as follows. A two step procedure was used. First, the following DNA pieces were ligated together: (a) synthetic oligonucleotides which would provide a 5' HindIII cloning site, followed by the sequence ACAAAACAAA (SEQ ID NO: 6), the initiator ATG, and codons for HCV1a, beginning with amino acid 1027 and continuing to a BglI site at amino acid 1046; (b) a 683 bp BglI-ClaI restriction fragment (encoding amino acids 1046–1274) from pAcHLTns3ns4aPI; and (c) a pSP72 vector (Promega, Madison, Wis., GenBank/EMBL Accession Number X65332) which had been digested with HindIII and ClaI, dephosphorylated, and gel-purified. Plasmid pAcHLTns3ns4aPI was derived from pAcHLT, a baculovirus expression vector commercially available from BD Pharmingen (San Diego, Calif.). In particular, a pAcHLT EcoRI-PstI vector was prepared, as well as the following fragments: EcoRI-AiwnI, 935 bp, corresponding to amino acids 1027–1336 of the HCV-1 genome; AlwnI-SacII, 247 bp, corresponding to amino acids 1336–1419 of the HCV-1 genome; HinfI-BglI, 175 bp, corresponding to amino acids 1449–1509 of the HCV-1 genome; BglI-PstI, 619 bp, corresponding to amino acids 1510–1711 of the HCV-1 genome, plus the transcription termination codon. A SacII-HinfI synthetically generated fragment of 91 bp, corresponding to amino acids 1420–1448 of the HCV-1 genome and containing the PI mutations (Thr-1428 mutated to Pro, Ser-1429 mutated to Ile), was ligated with the 175 bp HinfI-BglI fragment and the 619 bp BglI-PstI fragment described above and subclone into a pGEM-5Zf(+) vector digested with SacII and PstI. pGEM-5Zf(+) is a commercially available *E. coli* vector (Promega, Madison, Wis., GenBank/EMBL Accession Number X65308). After transformation of competent HB101 cells, miniscreen analysis of individual clones and sequence verification, an 885 bp SacII-PstI fragment from pGEM5.PI clone2 was gel-purified. This fragment was ligated with the EcoRI-AlwnI 935 bp fragment, the AlwnI-SacII 247 bp fragment and the pAcHLT EcoRI-PstI vector, described above. The resultant construct was named pAcHLTns3ns4aPI.

The ligation mixture above was transformed into HB101-competent cells and plated on Luria agar plates containing 100 μg/ml ampicillin. Miniprep analyses of individual clones led to the identification of putative positives, two of which were amplified. The plasmid DNA for pSP72 1aHC, clones #1 and #2 were prepared with a Qiagen Maxiprep kit and were sequenced.

Figure 9:
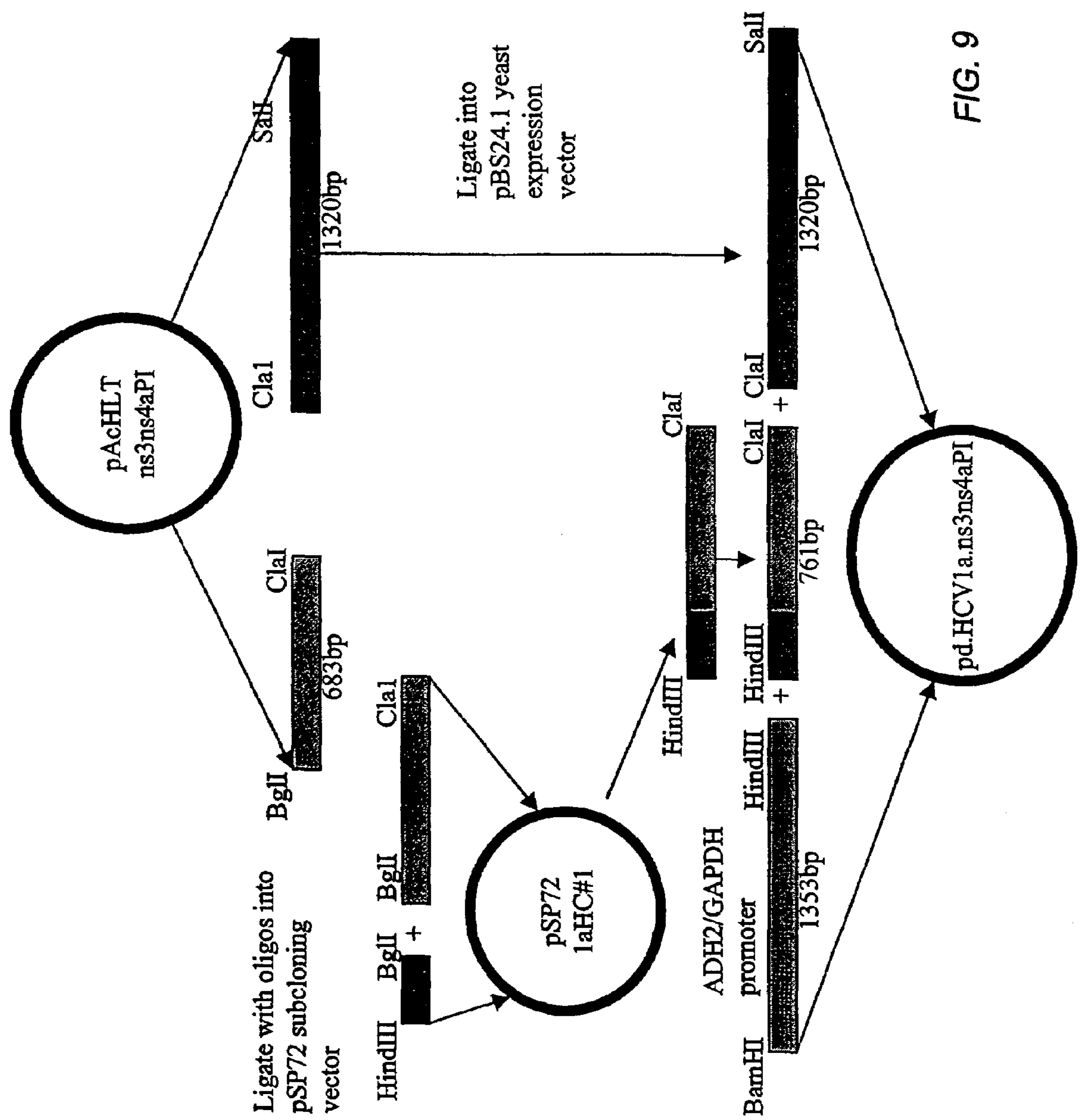
FIG. 9 is a diagram of the construction of pd.HCV1a.ns3ns4aPI.

Next, the following fragments were ligated together: (a) a 761 bp HindIII-ClaI fragment from pSP721aHC #1 (pSP72.1aHC was generated by ligating together the following: pSP72 which had been digested with HindIII and ClaI, synthetic oligonucleotides which would provide a 5' HindIII cloning site, followed by the sequence ACAAAACAAA (SEC ID NO:6), the initiation codon ATG, and codons for HCV1a, beginning with amino acid 1027 and continuing to a BglII site at amino acid 1046, and a 683 bp BglII-ClaI restriction fragment (encoding amino acids 1046–1274) from pAcHLTns3ns4aPI); (b) a 1353 bp BamHI-HindIII fragment for the yeast hybrid promoter ADH2/GAPDH; (c) a 1320 bp ClaI-SalI fragment (encoding HCV1a amino acids 1046–1711 with Thr 1428 mutated to Pro and Ser 1429 mutated to Ile) from pAcHLTns3ns4aPI; and (d) the pBS24.1 yeast expression vector which had been digested with BamHI and SalI, dephosphorylated and gel-purified. The ligation mixture was transformed into competent HB101 and plated on Luria agar plates containing 100 μg/ml ampicillin. Miniprep analyses of individual colonies led to the identification of clones with the expected 3446 bp BamHI-SalI insert which was comprised of the ADH2/GAPDH promoter, the initiator codon ATG and HCV1a NS3/4a from amino acids 1027–1711 (shown as amino acids 1–686 of FIGS. 3A–3D), with Thr 1428 (amino acid position 403 of FIGS. 3A–3D) mutated to Pro and Ser 1429 (amino acid position 404 of FIGS. 3A–3D) mutated to Ile. The construct was named pd.HCV1a.ns3ns4aPI (see, FIG. 9).

*S. cerevisiae* strain AD3 was transformed with pd.HCV1a.ns3ns4aPI and single transformants were checked for expression after depletion of glucose in the medium. The recombinant protein was expressed at high levels in yeast, as detected by Coomassie blue staining and confirmed by immunoblot analysis using a polyclonal antibody to the helicase domain of NS3.

EXAMPLE 3

Purification of NS3/4a Conformational Epitope

The NS3/4a conformational epitope was purified as follows. *S. cerevisiae* cells from above, expressing the NS3/4a epitope were harvested as described above. The cells were suspended in lysis buffer (50 mM Tris pH 8.0, 150 mM NaCl, 1 mM EDTA, 1 mM PMSF, 0.1 μM pepstatin, 1 μM leupeptin) and lysed in a Dyno-Mill (Wab Willy A. Bachofon, Basel, Switzerland) or equivalent apparatus using glass beads, at a ratio of 1:1:1 cells:buffer:0.5 mm glass beads. The lysate was centrifuged at 30100×g for 30 min at 4° C. and the pellet containing the insoluble protein fraction was added to wash buffer (6 ml/g start cell pellet weight) and rocked at room temperature for 15 min. The wash buffer consisted of 50 mM $NaPO_4$ pH 8.0, 0.3 M NaCl, 5 mM β-mercaptoethanol, 10% glycerol, 0.05% octyl glucoside, 1 mM EDTA, 1 mM PMSF, 0.1 μM pepstatin, 1 μM leupeptin. Cell debris was removed by centrifugation at 30100×g for 30 min at 4° C. The supernatant was discarded and the pellet retained.

Protein was extracted from the pellet as follows. 6 ml/g extraction buffer was added and rocked at room temperature for 15 min. The extraction buffer consisted of 50 mM Tris pH 8.0, 1 M NaCl, 5 mM β-mercaptoethanol, 10% glycerol, 1 mM EDTA, 1 mM PMSF, 0.1 μM pepstatin, 1 μM leupeptin. This was centrifuged at 30100×g for 30 min at 4° C. The supernatant was retained and ammonium sulfate added to 17.5% using the following formula: volume of supernatant (ml) multiplied by x % ammonium sulfate/(1−x % ammonium sulfate)=ml of 4.1 M saturated ammonium sulfate to add to the supernatant. The ammonium sulfate was added dropwise while stirring on ice and the solution stirred on ice for 10 min. The solution was centrifuged at 17700×g for 30 min at 4° C. and the pellet retained and stored at 2° C. to 8° C. for up to 48 hrs.

The pellet was resuspended and run on a Poly U column (Poly U Sepharose 4B, Amersham Pharmacia) at 4° C. as follows. Pellet was resuspended in 6 ml Poly U equilibration buffer per gram of pellet weight. The equilibration buffer consisted of 25 mM HEPES pH 8.0, 200 mM NaCl, 5 mM DTT (added fresh), 10% glycerol, 1.2 octyl glucoside. The solution was rocked at 4° C. for 15 min and centrifuged at 31000×g for 30 min at 4° C.

A Poly U column (1 ml resin per gram start pellet weight) was prepared. Linear flow rate was 60 cm/hr and packing flow rate was 133% of 60 cm/hr. The column was equilibrated with equilibration buffer and the supernatant of the resuspended ammonium sulfate pellet was loaded onto the equilibrated column. The column was washed to baseline with the equilibration buffer and protein eluted with a step elution in the following Poly U elution buffer: 25 mM HEPES pH 8.0, 1 M NaCl, 5 mM DTT (added fresh), 10% glycerol, 1.2 octyl glucoside. Column eluate was run on SDS-PAGE (Coomassie stained) and aliquots frozen and stored at −80° C. The presence of the NS3/4a epitope was confirmed by Western blot, using a polyclonal antibody directed against the NS3 protease domain and a monoclonal antibody against the 5-1-1 epitope (HCV 4a).

Additionally, protease enzyme activity was monitored during purification as follows. An NS4A peptide (KKGSVVIVGRIVLSGKPAIIPKK) (SEQ ID NO:7), and the sample containing the NS3/4a conformational epitope, were diluted in 90 μl of reaction buffer (25 mM Tris, pH 7.5, 0.15M NaCl, 0.5 mM EDTA, 10% glycerol, 0.05 n-Dodecyl B-D-Maltoside, 5 mM DTT) and allowed to mix for 30 minutes at room temperature. 90 μl of the mixture were added to a microtiter plate (Costar, Inc., Corning, N.Y.) and 10 μl of HCV substrate (AnaSpec, Inc., San Jose Calif.) was added. The plate was mixed and read on a Fluostar plate reader. Results were expressed as relative fluorescence units (RFU) per minute.

Using these methods, the product of the 1 M NaCl extraction contained 3.7 RFU/min activity, the ammonium sulfate precipitate had an activity of 7.5 RFU/min and the product of the Poly U purification had an activity of 18.5 RFU/min.

EXAMPLE 4

Coating Solid Support with the HCV Antigens

The HCV NS3/4a conformational epitope and MEFA 7.1 antigen were coated onto plates as follows. HCV coating buffer (50 mM NaPO4 pH 7.0, 2 mM EDTA and 0.1% Chloroacetamide) was filtered through a 0.22μ filter unit. The following reagents were then added sequentially to the HCV coating buffer and stirred after each addition: 2 μg/ml BSA-Sulfhydryl Modified, from a 10 mg/ml solution (Bayer Corp. Pentex, Kankakee, Ill.); 5 mM DTT from a 1 M solution (Sigma, St. Louis, Mo.); 0.45 μg/ml NS3/4a (protein concentration of 0.3 mg/ml); 0.375 μg/ml MEFA 7.1 (protein concentration of 1 mg/ml). The final solution was stirred for 15 minutes at room temperature.

200 μl of the above solution was added to each well of a Costar high binding, flat bottom plate (Coming Inc., Coming, N.Y.) and the plates were incubated overnight in a moisture chamber. The plates were then washed with wash buffer (1×PBS, 0.1% TWEEN-20), Tapped dry and 285 μl Ortho Post-Coat Buffer (1×PBS, pH 7.4, 1% BSA, 3% sucrose) added. The plates were incubated for at least 1 hour, tapped and dried overnight at 2–8° C. The plates were pouched with desiccants for future use.

EXAMPLE 5

Early Seroconversion Studies

The performance of the NS3/4a and MEFA 7.1 antigens in a combination assay (HCV 4.0) was compared to other HCV assays to test the seroconversion detection limits and to compare these limits to those obtained in other commercially available assays. Panels of commercially available human blood samples were used which were HCV-infected. The PHV panels shown in the tables below were purchased from Boston Biomedica, Inc., West Bridgewater, Mass. (BBI). The 6212 panels were purchased from Bioclinical Partners, Franklin, Mass. (BCP). The SC panels were purchased from North American Biologics, Inc., BocoRatan, Fla. (NABI). The day on which the blood samples was obtained is indicated in the tables.

The HCV 4.0 assay was conducted as follows. 200 μl of specimen diluent buffer (1 g/l casein, 100 mg/l recombinant human SOD, 1 g/l chloracetamide, 10 g/l BSA, 500 mg/l yeast extract, 0.366 g/l EDTA, 1.162 g/l $KPO_4$, 5 ml/i Tween-20, 29.22 g/l NaCl, 1.627 g/l $NaPO_4$, 1% SDS) was added to the coated plates. 20 μl of sample was then added. This was incubated at 37° C. for one hour. The plates were washed with wash buffer (1×PBS, pH 7.4, 0.1% Tween-20). 200 μl conjugate solution (a mouse anti-human IgG-HRP, such as mouse anti-human IgG-HRP diluted 1:22,000 in ORTHO HCV 3.0 ELISA Test System with Enhanced SAVe bulk conjugate diluent (Ortho-Clinical Diagnostics, Raritan, N.J.) was added and incubated for 60 minutes at 37° C. This was washed as above, and 200 μl substrate solution (1 OPD tablet/10 ml) was added. The OPD tablet contains o-phenylenediamine dihydrochloride and hydrogen peroxide for horse radish peroxidase reaction color development. This was incubated for 30 minutes at room temperature in the dark. The reaction was stopped by addition of 50 μl 4N $H_2SO_4$ and the plates were read at 492 nm, relative to absorbance at 690 nm as control.

The other assays used in the study were as follows:

The Abbott PRISM assay (Abbott Laboratories, Abbott Park, Ill.), is commercially available and is an antibody-based detection assay. The assay was performed using the manufacturer's instructions.

The ORTHO HCV Version 3.0 ELISA Test System (HCV 3.0) (Ortho Clinical Diagnostics, Raritan, N.J.) is an antibody-based detection assay. The assay was conducted using the manufacturer's instructions.

The Pasteur MONOLISA anti-HCV Plus Version 2 assay (Sanofi Diagnostics Pasteur, Marnes-la-Coquette, France) is an antibody-based detection assay. The assay was performed using the manufacturer's instructions.

The performance of the HCV 4.0 assay was compared to the HCV 3.0, PRISM and Pasteur assays (see, Tables 3 and 4). HCV antibodies present in the blood panels (anti-c33c or anti-c22) are set forth in Table 4. In particular, 17 seroconversion panels from the three commercial sources set forth above were assayed using the techniques above. As can be seen, for the c33c panels, HCV 4.0 showed earlier detection (by 1–3 bleeds) than HCV 3.0 in 9 out of 9 c33c panels, and earlier detection than PRISM in 6 out of 9 panels and equivalent detection as compared with PRISM in 3 of the 9 panels. For the c22 panels, HCV 4.0 showed earlier detection than HCV 3.0 in 3 of 8 panels and equivalent detection in the other 5 panels. HCV 4.0 also showed earlier detection than PRISM in 2 of 8 panels and equivalent detection in 6 of 8 panels. The range of improvement seen was 2–14 days over both the HCV 3.0 and PRISM assays.

TABLE 3

| ID | Bleed Day | s | HCV 4.0 s/co | Ortho HCV 3.0 s/co | Abbott Prism s/co |
|---|---|---|---|---|---|
| PHV 904-1 | 0 | 0.031 | 0.05 | 0.01 | 0.12 |
| PHV 904-2 | 2 | 0.024 | 0.04 | 0.01 | 0.08 |
| PHV 904-3 | 7 | 1.391 | 2.11 | 0.33 | 0.51 |
| PHV 904-4 | 9 | 2.813 | 4.28 | 1.10 | 1.56 |
| PHV 904-5 | 14 | 3.197 | 4.86 | 3.27 | 3.54 |
| PHV 904-6 | 21 | 3.176 | 4.83 | 3.92 | 4.45 |
| PHV 904-7 | 23 | 3.554 | 5.40 | 4.26 | 4.69 |
| PHV 905-1 | 0 | 0.015 | 0.02 | 0.02 | 0.06 |
| PHV 905-2 | 4 | 0.019 | 0.03 | 0.01 | 0.07 |
| PHV 905-3 | 7 | 0.079 | 0.12 | 0.02 | 0.14 |
| PHV 905-4 | 11 | 0.950 | 1.44 | 0.42 | 0.70 |
| PHV 905-5 | 14 | 1.586 | 2.41 | 0.80- | 1.21 |
| PHV 905-6 | 18 | 2.529 | 3.84 | 1.32 | 2.00 |
| PHV 905-7 | 21 | 3.177 | 4.83 | 2.54 | 3.44 |
| PHV 905-8 | 25 | 3.419 | 5.20 | 4.45 | 4.74 |
| PHV 905-9 | 28 | 3.408 | 5.18 | 4.85 | 5.04 |
| PHV 907-1 | 0 | 0.030 | 0.05 | 0.01 | 0.09 |
| PHV 907-2 | 4 | 0.023 | 0.03 | 0.01 | 0.09 |
| PHV 907-3 | 7 | 0.021 | 0.03 | 0.01 | 0.11 |
| PHV 907-4 | 13 | 0.148 | 0.22 | 0.13 | 0.35 |
| PHV 907-5 | 18 | 1.726 | 2.62 | 0.83- | 1.68 |
| PHV 907-6 | 21 | 2.785 | 4.23 | 1.59 | 3.12 |
| PHV 907-7 | 164 | 3.279 | 4.98 | 4.85 | 5.16 |
| PHV 908-1 | 0 | 0.029 | 0.04 | 0.01 | 0.07 |
| PHV 908-2 | 3 | 0.079 | 0.12 | 0.01 | 0.08 |
| PHV 908-3 | 5 | 0.399 | 0.61 | 0.01 | 0.13 |
| PHV 908-4 | 11 | 1.780 | 2.71 | 0.50 | 1.27 |
| PHV 908-5 | 13 | 2.068 | 3.14 | 0.67 | 1.61 |
| PHV 908-6 | 19 | 2.793 | 4.24 | 1.16 | 3.11 |
| PHV 908-7 | 25 | 3.390 | 5.15 | 3.11 | 4.29 |
| PHV 908-8 | 27 | 3.299 | 5.01 | 3.78 | 4.44 |
| PHV 908-9 | 32 | 3.474 | 5.28 | 4.85 | 4.54 |
| PHV 908-10 | 35 | 3.707 | 5.63 | 4.85 | 4.92 |
| PHV 908-11 | 41 | 3.363 | 5.11 | 4.85 | 6.09 |
| PHV 908-12 | 45 | 3.372 | 5.12 | 3.80 | 5.79 |
| PHV 908-13 | 48 | 3.278 | 4.98 | 4.85 | 5.56 |

TABLE 3-continued

| ID | Bleed Day | s | HCV 4.0 s/co | Ortho HCV 3.0 s/co | Abbott Prism s/co |
|---|---|---|---|---|---|
| PHV 913-1 | 0 | 0.060 | 0.09 | 0.01 | 0.08 |
| PHV 913-2 | 2 | 0.242 | 0.37 | 0.02 | 0.10 |
| PHV 913-3 | 7 | 0.893 | 1.36 | 0.43- | 0.5- |
| PHV 913-4 | 9 | 1.141 | 1.73 | 0.54- | 0.59- |
| PHV 914-1 | 0 | 0.033 | 0.05 | 0.00 | 0.06 |
| PHV 914-2 | 5 | 0.024 | 0.04 | 0.01 | 0.06 |
| PHV 914-3 | 9 | 0.135 | 0.21 | 0.01 | 0.06 |
| PHV 914-4 | 12 | 2.653 | 4.03 | 0.04 | 0.09 |
| PHV 914-5 | 16 | 3.020 | 4.59 | 0.33- | 0.47- |
| PHV 914-6 | 19 | 2.302 | 3.50 | 0.82- | 0.9- |
| PHV 914-7 | 24 | 2.697 | 4.10 | 3.10 | 2.41 |
| PHV 914-8 | 30 | 2.744 | 4.17 | 4.85 | 4.09 |
| PHV 914-9 | 33 | 2.991 | 4.55 | 4.85 | 4.52 |
| 6212-1 | Nov. 16, 1995 | 0.723 | 1.10 | 0.01 | 0.08 |
| 6212-2 | Nov. 28, 1995 | 2.716 | 4.13 | 0.85 | 1.26 |
| 6212-3 | Nov. 30, 1995 | 3.117 | 4.74 | 1.15 | 1.11 |
| 6212-4 | Dec. 09, 1995 | 3.278 | 4.98 | 4.08 | 2.65 |
| 6212-5 | Dec. 12, 1995 | 3.527 | 5.36 | 5.04 | 3.13 |
| 6212-6 | Dec. 18, 1995 | 3.292 | 5.00 | 5.51 | 3.07 |
| 6212-7 | Dec. 23, 1995 | 3.096 | 4.71 | 5.43 | 2.80 |
| 6212-8 | Jan. 08, 1996 | 3.241 | 4.93 | 13.4 | 3.48 |
| 6212-9 | Jan. 10, 1996 | 3.306 | 5.02 | 13.4 | 4.04 |
| 6213-1 | Jan. 16, 1996 | 0.035 | 0.05 | 0.01 | 0.09 |
| 6213-2 | Jan. 18, 1996 | 0.028 | 0.04 | 0.00 | 0.07 |
| 6213-3 | Jan. 24, 1996 | 0.037 | 0.06 | 0.01 | 0.08 |
| 6213-4 | Jan. 27, 1996 | 0.047 | 0.07 | 0.01 | 0.09 |
| 6213-5 | Jan. 31, 1996 | 0.034 | 0.05 | 0.01 | 0.07 |
| 6213-6 | Feb. 03, 1996 | 0.037 | 0.06 | 0.01 | 0.07 |
| 6213-7 | Feb. 13, 1996 | 0.056 | 0.09 | 0.01 | 0.07 |
| 6213-8 | Feb. 15, 1996 | 0.027 | 0.04 | 0.01 | 0.06 |
| 6213-9 | Feb. 20, 1996 | 0.098 | 0.15 | 0.01 | 0.11 |
| 6213-10 | Feb. 22, 1996 | 1.572 | 2.39 | 0.46- | 1.26 |
| 6213-11 | Feb. 28, 1996 | 3.410 | 5.18 | 4.18 | 4.75 |
| 6213-12 | Mar. 02, 1996 | 3.224 | 4.90 | 4.67 | 4.68 |

TABLE 3-continued

| ID | Bleed Day | s | HCV 4.0 s/co | Ortho HCV 3.0 s/co | Abbott Prism s/co |
|---|---|---|---|---|---|
| 6214-1 | Jan. 13, 1996 | 0.042 | 0.06 | 0.01 | 0.09 |
| 6214-2 | Jan. 15, 1996 | 0.016 | 0.02 | 0.00 | 0.07 |
| 6214-3 | Jan. 21, 1996 | 0.035 | 0.05 | 0.00 | 0.07 |
| 6214-4 | Jan. 23, 1996 | 0.028 | 0.04 | 0.00 | 0.07 |
| 6214-5 | Jan. 29, 1996 | 0.031 | 0.05 | 0.00 | 0.08 |
| 6214-6 | Jan. 31, 1996 | 0.028 | 0.04 | 0.00 | 0.09 |
| 6214-7 | Feb. 05, 1996 | 0.364 | 0.55 | 0.01 | 0.59 |
| 6214-8 | Feb. 07, 1996 | 0.916 | 1.39 | 0.02- | 1.36 |
| 6214-9 | Feb. 12, 1996 | 2.290 | 3.48 | 0.94- | 2.31 |
| 6214-10 | Feb. 14, 1996 | 3.669 | 5.58 | 2.29 | 3.05 |
| 6214-11 | Mar. 02, 1996 | 3.523 | 5.35 | 3.15 | 5.32 |
| 6214-12 | Mar. 06, 1996 | 3.125 | 4.75 | 4.75 | 5.38 |
| 6214-13 | Mar. 09, 1996 | 3.246 | 4.93 | 4.89 | 5.17 |
| 6222-1 | Aug. 18, 1996 | 0.023 | 0.03 | 0.01 | 0.08 |
| 6222-2 | Aug. 20, 1996 | 0.151 | 0.23 | 0.00 | 0.06 |
| 6222-3 | Sep. 04, 1996 | 0.053 | 0.08 | 0.00 | 0.06 |
| 6222-4 | Sep. 06, 1996 | 0.016 | 0.02 | 0.00 | 0.06 |
| 6222-5 | Sep. 11, 1996 | 0.015 | 0.02 | 0.00 | 0.07 |
| 6222-6 | Sep. 13, 1996 | 0.009 | 0.01 | 0.00 | 0.06 |
| 6222-7 | Sep. 23, 1996 | 0.817 | 1.24 | 0.04 | 0.36 |
| 6222-8 | Sep. 27, 1996 | 2.862 | 4.35 | 1.10 | 3.74 |

| ID | Bleed Day | s | HCV 4.0 s/co | Ortho HCV 3.0 s/co | Abbott Prism s/co |
|---|---|---|---|---|---|
| SC-0030-A | 1 | 0.024 | 0.04 | 0.01 | 0.05 |
| SC-0030-B | 40 | 1.658 | 2.52 | 0.94- | 0.54- |
| SC-0030-C | 45 | 2.372 | 3.60 | 3.07 | 3.15 |
| SC-0040-A | 1 | 0.773 | 1.17 | 0.02 | 0.09 |
| SC-0040-B | 3 | 1.491 | 2.27 | 0.12 | 0.54 |
| SC-0040-C | 8 | 2.400 | 3.65 | 0.77- | 2.66 |
| SC-0040-D | 10 | 2.639 | 4.01 | 1.37 | 3.23 |
| SC-0040-E | 15 | 3.423 | 5.20 | 3.46 | 3.46 |

TABLE 4

| | | | Bleed days earlier detection | | | |
|---|---|---|---|---|---|---|
| | | Panel | HCV 3.0 | Abbott Prism | early c33c panels | early c22 panels |
| #1 | c33c | PHV 904 | 2 | 2 | PHV 904 | PHV 907 |
| #2 | c33c | PHV 905 | 7 | 3 | PHV 905 | PHV 909 |
| #3 | c22 | PHV 907 | 3 | 0 | PHV 908 | PHV 910 |
| #4 | c33c | PHV 908 | 8 | 0 | PHV 914 | PHV 911 |
| #5 | c22 | PHV 909 | 0 | 0 | 6212 | PHV 912 |
| #6 | c22 | PHV 910 | 0 | 0 | 6213 | PHV 913 |
| #7 | c22 | PHV 911 | 0 | 0 | 6214 | SC-0010 |
| #8 | c22 | PHV 912 | 0 | 0 | 6222 | SC-0030 |
| #9 | c22 | PHV 913 | 2 | 2 | SC-0040 | |
| #10 | c33c | PHV 914 | 12 | 12 | | |
| #11 | c33c | 6212 | 14 | 12 | | |
| #12 | c33c | 6213 | 6 | 0 | | |

TABLE 4-continued

| | | | Bleed days earlier detection | | | |
|---|---|---|---|---|---|---|
| | | Panel | HCV 3.0 | Abbott Prism | early c33c panels | early c22 panels |
| #13 | c33c | 6214 | 7 | 0 | | |
| #14 | c33c | 6222 | 4 | 4 | | |
| #15 | c22 | SC-0010 | 0 | 0 | | |
| #16 | c22 | SC-0030 | 5 | 5 | | |
| #17 | c33c | SC-0040 | 9 | 7 | | |
| Range of improvement | | | 2–14 days | 2–12 days | | |

EXAMPLE 6

HCV 4.0 Genotype Sensitivity

The genotype sensitivity of the HCV 4.0 assay was compared to the HCV 3.0 and Pasteur assays, described above. In particular, samples from 10 different HCV genotypes, specified in Table 5, were diluted as indicated in the table (2-fold or 10-fold depending on initial sample titering) and used in the three assays, using the procedures described above. All three tests were run simultaneously. The data is shown as signal or raw O.D. The data suggests that the HCV 4.0 prototype is more sensitive in detecting diluted genotype samples.

TABLE 5

HCV 4.0 and Genotype Dilutional Sensitivity

| dilution | genotype | HCV 4.0 prototype s | HCV 3.0 Ortho s | Monolisa Ver. 2 Pasteur s |
|---|---|---|---|---|
| 1:2500 | 1b | 2.866 | 1.007 | 0.694 |
| 1:5000 | | 2.074 | 0.393 | 0.218 |
| 1:10000 | | 1.099 | 0.159 | 0.084 |
| 1:20000 | | 0.403 | 0.045 | 0.028 |
| 1:2500 | 2b | 1.430 | 0.295 | 0.658 |
| 1:5000 | | 0.551 | 0.108 | 0.207 |
| 1:10000 | | 0.225 | 0.032 | 0.061 |
| 1:20000 | | 0.074 | 0.010 | 0.019 |
| 1:2500 | 2a/c | 1.952 | 0.467 | 1.653 |
| 1:5000 | | 0.917 | 0.136 | 0.782 |
| 1:10000 | | 0.395 | 0.049 | 0.286 |
| 1:20000 | | 0.108 | 0.011 | 0.105 |
| 1:2500 | 3a | 2.580 | 0.514 | 0.941 |
| 1:5000 | | 1.622 | 0.218 | 0.353 |
| 1:10000 | | 0.873 | 0.067 | 0.164 |
| 1:20000 | | 0.398 | 0.023 | 0.050 |
| 1:2500 | 3e | 1.207 | 0.158 | 0.291 |
| 1:5000 | | 0.461 | 0.039 | 0.114 |
| 1:10000 | | 0.155 | 0.011 | 0.053 |
| 1:20000 | | 0.054 | 0.003 | 0.024 |
| | 4b/c | 2.478 | 0.701 | 0.551 |
| | | 1.125 | 0.256 | 0.195 |
| | | 0.609 | 0.087 | 0.076 |
| | | 0.216 | 0.035 | 0.033 |
| | 4a | 2.831 | 0.632 | 0.462 |
| | | 1.752 | 0.193 | 0.181 |
| | | 0.717 | 0.069 | 0.076 |
| | | 0.248 | 0.015 | 0.025 |
| | 4c | 1.751 | 0.457 | 1.147 |
| | | 0.856 | 0.169 | 0.474 |
| | | 0.384 | 0.055 | 0.178 |
| | | 0.141 | 0.018 | 0.058 |
| | 5a | 2.682 | 1.496 | 2.271 |
| | | 2.744 | 0.827 | 0.988 |
| | | 1.587 | 0.316 | 0.395 |
| | | 0.726 | 0.097 | 0.120 |
| 1:10 | 6 | 3.516 | 3.247 | ND |

TABLE 5-continued

HCV 4.0 and Genotype Dilutional Sensitivity

| dilution | genotype | HCV 4.0 prototype s | HCV 3.0 Ortho s | Monolisa Ver. 2 Pasteur s |
|---|---|---|---|---|
| 1:100 | | 3.602 | 3.594 | ND |
| 1:1000 | | 3.224 | 2.863 | ND |
| 1:10000 | | 1.192 | 0.380 | ND |

EXAMPLE 7

Competition Studies

The following competition study was conducted in order to assess whether the NS3/4a conformational epitope detected different antibodies than other HCV antigens. In particular, the NS3/4a antigen was compared with the c200 antigen as follows.

0.5 µg and 1.0 µg of NS3/4a, produced as described above, or c200 (*Hepatology* (1992) 15:19–25, available in the ORTHO HCV Version 3.0 ELISA Test System, Ortho-Clinical Diagnostics, Raritan, N.J.), were mixed with 20 µl of sample PHV914-5 (an early seroconversion bleed obtained from blood of an infected individual) in a total volume of 220 µl (1×PBS). The mixture was incubated for 1 hour in microwells at 37° C. The mixture was then transferred to NS3/4a-coated plates and incubated for 1 hour at 37° C. Plates were washed and assayed as follows.

1 µg of c200 antigen was added to 10 µl of sample PHV914-5 in a total volume of about 220 µl. The mixture was incubated for 1 hour in a micro well at 37° C. and 200 µl transferred to an NS3/4a-coated plate (100 ng/assay) and incubated for 1 hour at 37° C. Plates were washed five times with 1×PBS, 0.1% Tween-20. 200 µl of conjugate solution (described above) were added, and the plates incubated and assayed as described in Example 4 for the HCV 4.0 assay. Controls which consisted of PHV914-5 and 1×PBS (without antigen) were also treated as above.

Results are shown in Table 6. Percent inhibition results shown in column 4 are calculated as column 3 minus (column 2 divided by column 3 times 100). As can be seen, the data show that NS34a is neutralized by early seroconversion antibodies and c200 is not. A strong signal was achieved when antibodies in PHV914-5 c33c early seroconversion panel member reacted with the NS34a coated on the plate. The c200 antigen was not neutralized by these antibodies. This is shown in the top panel of Table 6. When NS34a was mixed with the PHV914-5 sample, it was neutralized and therefore no antibodies were present in the sample to react with NS34a that was coated on the microplate. The data indicate that NS34a may be detecting a different class of antibodies than is detected by c200.

Competition Studies to Show NS34a Antigen Detects Different Antibodies in Early c33c Seroconversion Panel Compared to c200 Antigen

TABLE 6

| 1 | 2 s | 3 *Control 1xPBS s | 4 % Inhibition |
|---|---|---|---|
| | c200 + PHV914-5 | | |
| 1 ug | 1.450 | 1.645 | 12 |
| 1 ug | 1.545 | 1.687 | 8 |
| 0.5 ug | 1.557 | 1.913 | 19 |
| 0.5 ug | 1.719 | 1.804 | 5 |
| | NS3/4a + PHV914-5 | | |
| 1 ug | 0.054 | 1.599 | 97 |
| 1 ug | 0.037 | 1.677 | 98 |
| 0.5 ug | 0.066 | 1.672 | 96 |
| 0.5 ug | NA | 1.524 | NA |

EXAMPLE 8

Stability Studies of NS3/4a Conformational Epitope

To assess the role of stability of the NS3/4a epitope to assay performance, the following study was done to determine NS3/4a immunoreactivity versus time at room temperature. Small aliquots of stock NS3/4a were allowed to sit at room temperature and then frozen at intervals as shown in Table 7. All vials were coated simultaneously and tested against two early NS3 seroconversion panels. Assays were conducted as described above in Example 5 for HCV 4.0.

As can be seen in Table 7, the NS3/4a stock is not stable and immunoreactivity decreases with time. In addition, maintaining NS3/4a conformation is necessary for immunoreactivity.

Further stability studies were conducted as follows. Two conformational monoclonal antibodies made against NS3/4a using standard procedures were substituted for anti-HCV early seroconversion panels. Stock NS3/4a vials were stored at room temperature at time intervals 3, 6 and 24 hours. The NS3/4a from the frozen vials was coated at 90 ng/ml and assayed using the procedure described above. Results suggested that the two monoclonals were indeed conformational and their reactivity was sensitive to the handling of stock NS3/4a antigen at room temperature. The reactivity of a positive control monoclonal antibody did not change.

TABLE 7

| Time (hrs) | 0 | 6 | 21.4 | 29 | 35.5 | 46 | 52 | control |
|---|---|---|---|---|---|---|---|---|
| | A | D | G | H | I | K | N | Reference |
| | s/co | s/co | s/co | s/co | s/co | s/co | s/co | s/co |
| PHV 904-1 | 0.0 | 0.0 | 0.0 | 0.0 | 0.0 | 0.0 | 0.0 | 0.0 |
| PHV 904-2 | 0.0 | 0.0 | 0.0 | 0.0 | 0.0 | 0.0 | 0.0 | 0.0 |
| PHV 904-3 | 1.5 | 0.3 | 0.1 | 0.0 | 0.0 | 0.0 | 0.0 | 1.8 |
| PHV 904-4 | 3.7 | 1.0 | 0.2 | 0.1 | 0.1 | 0.1 | 0.1 | 4.4 |
| PHV 904-5 | 4.8 | 2.0 | 0.7 | 0.6 | 0.3 | 0.2 | 0.3 | 5.5 |
| PHV 904-6 | 5.4 | 2.8 | 1.1 | 1.0 | 0.6 | 0.5 | 0.6 | 5.8 |
| PHV 904-7 | 5.1 | 3.4 | 1.5 | 1.0 | 1.1 | 0.5 | 0.7 | 5.4 |

TABLE 7-continued

| | | | | | | | | |
|---|---|---|---|---|---|---|---|---|
| PHV 914-1 | 0.0 | 0.0 | 0.0 | 0.0 | 0.0 | 0.0 | 0.0 | 0.0 |
| PHV 914-2 | 0.0 | 0.0 | 0.0 | 0.0 | 0.0 | 0.0 | 0.0 | 0.0 |
| PHV 914-3 | 0.0 | 0.0 | 0.0 | 0.0 | 0.0 | 0.0 | 0.0 | 0.0 |
| PHV 914-4 | 0.5 | 0.1 | 0.0 | 0.0 | 0.0 | 0.0 | 0.0 | 0.7 |
| PHV 914-5 | 2.1 | 0.4 | 0.0 | 0.0 | 0.0 | 0.0 | 0.0 | 3.0 |
| PHV 914-6 | 2.3 | 0.4 | 0.0 | 0.0 | 0.0 | 0.0 | 0.0 | 3.4 |
| PHV 914-7 | 2.8 | 0.5 | 0.1 | 0.1 | 0.0 | 0.0 | 0.0 | 4.9 |
| PHV 914-8 | 2.9 | 0.7 | 0.1 | 0.1 | 0.1 | 0.1 | 0.1 | 4.9 |
| | | | | | | | | |
| Enzyme | | | | | | | | |
| RFU/min | 8.75 | 4.14 | 3.08 | 1.88 | 1.75 | 1.75 | 0.75 | |

EXAMPLE 9

Immunoreactivity of NS3/4a Conformational Epitope Verus Denatured NS3/4a

The immunoreactivity of the NS3/4a conformational epitope, produced as described above, was compared to NS3/4a which had been denatured by adding SDS to the NS3/4a conformational epitope preparation to a final concentration of 2%. The denatured NS3/4a and conformational NS3/4a were coated onto microtiter plates as described above. The c200 antigen (*Hepatology* (1992) 15:19–25, available in the ORTHO HCV Version 3.0 ELISA Test System, Ortho-Clinical Diagnostics, Raritan, N.J.) was also coated onto microtiter plates. The c200 antigen was used as a comparison it is presumed to be non-conformational due to the presence of reducing agent (DTT) and detergent (SDS) in its formulation.

The immunoreactivity was tested against two early HCV seroconversion panels, PHV 904 and PHV 914 (commercially available human blood samples from Boston Biomedica, Inc., West Bridgewater, Mass.), using the ELISA assay procedure described above. The results are shown in Table 8. The data suggests that the denatured or linearized form of NS3/4a (as well as c200) does not detect early seroconversion panels as early as the NS3/4a conformational epitope.

TABLE 8

| | NS3/4a vs. denatured NS3/4a | | | | | | | |
|---|---|---|---|---|---|---|---|---|
| | *Spiked 2% SDS to stock NS3/4a | | | | | | | |
| | | NS3/4a | dNS3/4a* | c200 | | NS3/4a | dNS3/4a* | c200 |
| | | OD | OD | OD | | s/co | s/co | s/co |
| HCV | PHV 904-1 | 0.012 | 0.012 | 0.009 | | 0.02 | 0.02 | 0.01 |
| Serocon-versions | PHV 904-2 | 0.011 | 0.009 | 0.008 | | 0.02 | 0.01 | 0.01 |
| | PHV 904-3 | 1.124 | 0.071 | 0.045 | | 1.80 | 0.11 | 0.07 |
| | PHV 904-4 | 2.401 | 0.273 | 0.129 | | 3.85 | 0.44 | 0.21 |
| | PHV 904-5 | 3.022 | 0.793 | 0.347 | | 4.85 | 1.28 | 0.57 |
| | PHV 904-6 | 2.711 | 1.472 | 0.774 | | 4.35 | 2.37 | 1.28 |
| | PHV 904-7 | 3.294 | 1.860 | 0.943 | | 5.28 | 2.99 | 1.55 |
| | PHV 914-1 | 0.006 | 0.004 | 0.001 | | 0.01 | 0.01 | 0.00 |
| | PHV 914-2 | 0.005 | 0.004 | 0.002 | | 0.01 | 0.01 | 0.00 |
| | PHV 914-3 | 0.098 | 0.003 | 0.001 | | 0.16 | 0.00 | 0.00 |
| | PHV 914-4 | 1.118 | 0.006 | 0.004 | | 1.79 | 0.01 | 0.01 |
| | PHV 914-5 | 2.035 | 0.044 | 0.022 | | 3.26 | 0.07 | 0.04 |
| | PHV 914-6 | 2.092 | 0.074 | 0.025 | | 3.35 | 0.12 | 0.04 |
| | PHV 914-7 | 2.519 | 0.281 | 0.132 | | 4.04 | 0.45 | 0.22 |
| | PHV 914-8 | 2.746 | 0.907 | 0.500 | | 4.40 | 1.46 | 0.82 |
| | PHV 914-9 | 3.084 | 1.730 | 0.931 | | 4.94 | 2.78 | 1.53 |
| HCV 3.0 | Neg. Cont. | 0.023 | 0.024 | 0.008 | | | | |
| Controls | Neg. Cont. | 0.027 | 0.024 | 0.007 | | | | |
| | Neg. Cont. | 0.021 | 0.017 | 0.005 | | | | |
| | average | 0.024 | 0.022 | 0.007 | | | | |
| | cutoff | 0.624 | 0.622 | 0.607 | | | | |
| | | | | | | | | |
| | | | | | | | | |
| | Pos. Cont. | 1.239 | 0.903 | 0.575 | | 1.99 | 1.45 | 0.95 |
| | Pos. Cont. | 1.445 | 0.916 | 0.614 | | 2.32 | 1.47 | 1.01 |

Immunoreactivity of the conformational epitope was also tested using monoclonal antibodies to NS3/4a, made using standard procedures. These monoclonal antibodies were then tested in the ELISA format described above against NS3/4a and denatured NS3/4a and c200 antigen. The data show that anti-NS3/4a monoclonals react to the NS3/4a and denatured NS3/4a in a similar manner to the seroconversion panels shown in Table 9. This result also provides further evidence that the NS3/4a is conformational in nature as monoclonal antibodies can be made which are similar in reactivity to the early c33c seroconversion panels.

TABLE 9

| | | Plate | | |
|---|---|---|---|---|
| Monoclonal | | NS3/4a OD | dNS3/4a OD | c200 OD |
| 4B9/E3 | 1:100 | 1.820 | 0.616 | 0.369 |
| | 1:1000 | 1.397 | 0.380 | 0.246 |
| | 1:10000 | 0.864 | 0.173 | 0.070 |
| | 1:20000 | 0.607 | 0.116 | 0.085 |
| 5B7/D7 | 1:100 | 2.885 | 0.898 | 0.436 |
| | 1:1000 | 2.866 | 0.541 | 0.267 |

TABLE 9-continued

| | | Plate | | |
|---|---|---|---|---|
| Monoclonal | | NS3/4a OD | dNS3/4a OD | c200 OD |
| | 1:10000 | 1.672 | 0.215 | 0.086 |
| | 1:20000 | 1.053 | 0.124 | 0.059 |
| 1A8/H2 | 1:100 | 1.020 | 0.169 | 0.080 |
| | 1:1000 | 0.921 | 0.101 | 0.043 |
| | 1:10000 | 0.653 | 0.037 | 0.013 |
| | 1:20000 | 0.337 | 0.027 | 0.011 |

Accordingly, novel HCV detection assays have been disclosed. From the foregoing, it will be appreciated that, although specific embodiments of the invention have been described herein for purposes of illustration, various modifications may be made without deviating from the spirit and scope thereof.

The invention claimed is:

1. A polynucleotide comprising a coding sequence for a multiple epitope fusion antigen, wherein said multiple epitope fusion antigen the amino acid sequence of SEQ ID NO: 4, or an amino acid sequence with at least 80% sequence identity thereto which binds specifically with anti-HCV antibodies present in a biological sample from an HCV-infected individual, wherein said antibodies specifically bind with SEQ ID NO: 4.

2. The polynucleotide of claim 1, wherein said polynucleotide comprises a coding sequence for a multiple epitope fusion antigen that comprises an amino acid sequence with at least 90% sequence identity to the amino acid sequence of SEQ ID NO: 4 which binds specifically with anti-HCV antibodies present in a biological sample from an HCV-infected individual, wherein said antibodies specifically bind with SEQ ID NO: 4.

3. The polynucleotide of claim 1, wherein said polynucleotide comprises a coding sequence for a multiple epitope fusion antigen that comprises an amino acid sequence with at least 98% sequence identity to the amino acid sequence of SEQ ID NO: 4, which binds specifically with anti-HCV antibodies present in a biological sample from an HCV-infected individual, wherein said antibodies specifically bind with SEQ ID NO: 4.

4. The polynucleotide of claim 1, wherein said polynucleotide comprises a coding sequence for a multiple epitope fusion antigen that consists of the amino acid sequence of SEQ ID NO: 4.

5. The polynucleotide of claim 1, wherein said polynucleotide comprises the nucleic acid sequence of SEQ ID NO: 3, or a nucleic acid sequence with at least 80% sequence identity thereto which encodes a polypeptide that binds specifically with anti-HCV antibodies present in a biological sample from an HCV-infected individual.

6. The polynucleotide of claim 1, wherein said polynucleotide comprises the nucleic acid sequence of SEQ ID NO: 3, or a nucleic acid sequence with at least 90% sequence identity thereto which encodes a polypeptide that binds specifically with anti-HCV antibodies present in a biological sample from an HCV-infected individual.

7. The polynucleotide of claim 1, wherein said polynucleotide comprises the nucleic acid sequence of SEQ ID NO: 3, or a nucleic acid sequence with at least 98% sequence identity thereto which encodes a polypeptide that binds specifically with anti-HCV antibodies present in a biological sample from an HCV-infected individual.

8. A recombinant vector comprising:

(a) a polynucleotide according to claim 1;

(b) and control elements operably linked to said polynucleotide whereby the coding sequence can be transcribed and translated in a host cell.

9. A recombinant vector comprising:

(a) a polynucleotide according to claim 4;

(b) and control elements operably linked to said polynucleotide whereby the coding sequence can be transcribed and translated in a host cell.

10. A recombinant vector comprising:

(a) a polynucleotide according to claim 5;

(b) and control elements operably linked to said polynucleotide whereby the coding sequence can be transcribed and translated in a host cell.

11. A recombinant vector comprising:

(a) a polynucleotide according to claim 7;

(b) and control elements operably linked to said polynucleotide whereby the coding sequence can be transcribed and translated in a host cell.

12. A host cell transformed with the recombinant vector of claim 8.

13. A host cell transformed with the recombinant vector of claim 9.

14. A host cell transformed with the recombinant vector of claim 10.

15. A host cell transformed with the recombinant vector of claim 11.

16. A method of producing a recombinant multiple epitope fusion antigen comprising:

(a) providing a population of host cells according to claim 12; and (b) culturing said population of cells under conditions whereby the multiple epitope fusion antigen encoded by the coding sequence present in said recombinant vector is expressed.

17. A method of producing a recombinant multiple epitope fusion antigen comprising:

(a) providing a population of host cells according to claim 13; and (b) culturing said population of cells under conditions whereby the multiple epitope fusion antigen encoded by the coding sequence present in said recombinant vector is expressed.

18. A method of producing a recombinant multiple epitope fusion antigen comprising:

(a) providing a population of host cells according to claim 14; and (b) culturing said population of cells under conditions whereby the multiple epitope fusion antigen encoded by the coding sequence present in said recombinant vector is expressed.

19. A method of producing a recombinant multiple epitope fusion antigen comprising:

(a) providing a population of host cells according to claim 15; and (b) culturing said population of cells under conditions whereby the multiple epitope fusion antigen encoded by the coding sequence present in said recombinant vector is expressed.

* * * * *